US012789436B2

(12) United States Patent
Abbas et al.

(10) Patent No.: US 12,789,436 B2
(45) Date of Patent: Nov. 10, 2026

(54) METHOD OF PRODUCING A BIOACTIVE POLYMER FILAMENT, THE BIOACTIVE POLYMER FILAMENT AND PRINTING METHODS USING THE SAME

(71) Applicant: Agency for Science, Technology and Research, Singapore (SG)

(72) Inventors: Mohammad Asyraf Bin Abbas, Singapore (SG); Peili Teo, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 64 days.

(21) Appl. No.: 18/687,881

(22) PCT Filed: Aug. 30, 2022

(86) PCT No.: PCT/SG2022/050620
§ 371 (c)(1),
(2) Date: Feb. 29, 2024

(87) PCT Pub. No.: WO2023/033730
PCT Pub. Date: Mar. 9, 2023

(65) Prior Publication Data

US 2024/0351263 A1 Oct. 24, 2024

(30) Foreign Application Priority Data

Aug. 31, 2021 (SG) .......................... 10202109525R

(51) Int. Cl.

| | |
|---|---|
| ***B29C 48/05*** | (2019.01) |
| ***A61L 27/26*** | (2006.01) |
| ***A61L 27/54*** | (2006.01) |
| ***A61L 27/58*** | (2006.01) |
| ***B29C 48/00*** | (2019.01) |
| ***B29C 48/92*** | (2019.01) |
| ***B29C 64/118*** | (2017.01) |
| ***B29K 67/00*** | (2006.01) |
| ***B33Y 80/00*** | (2015.01) |

(Continued)

(52) U.S. Cl.
CPC .............. *B29C 48/05* (2019.02); *A61L 27/26* (2013.01); *A61L 27/54* (2013.01); *A61L 27/58* (2013.01); *B29C 48/022* (2019.02); *B29C 48/92* (2019.02); *B29C 64/118* (2017.08); *B33Y 80/00* (2014.12); *C08F 6/00* (2013.01); *C08G 61/08* (2013.01); *C08G 63/08* (2013.01); *C08L 65/00* (2013.01); *A61L 2300/25* (2013.01); *A61L 2430/02* (2013.01); *B29K 2065/00* (2013.01); *B29K 2067/043* (2013.01); *B29K 2067/046* (2013.01); *C08G 2261/1424* (2013.01); *C08G 2261/1426* (2013.01); *C08G 2261/143* (2013.01); *C08G 2261/1432* (2013.01); *C08G 2261/3324* (2013.01); *C08G 2261/344* (2013.01); *C08G 2261/418* (2013.01)

(58) Field of Classification Search
CPC ....... B29C 48/05; B29C 48/022; B29C 48/92; B29C 64/118; A61L 27/26; A61L 27/54; A61L 27/58; A61L 2300/25; A61L 2430/02; B33Y 80/00; C08F 6/00; C08G 61/08; C08G 63/08; C08G 2261/1424; C08G 2261/1426; C08G 2261/143; C08G 2261/1432; C08G 2261/3324; C08G 2261/344; C08G 2261/418; C08L 65/00; B29K 2065/00; B29K 2067/043; B29K 2067/046
See application file for complete search history.

(56) References Cited

U.S. PATENT DOCUMENTS 6,454,811 B1 * 9/2002 Sherwood ............... A61L 27/56 623/23.72
8,128,954 B2 * 3/2012 Davis .................. A61K 9/0092 424/426

(Continued)

FOREIGN PATENT DOCUMENTS

CN 109777059 A 5/2019
JP 2021-514874 A 6/2021

(Continued)

OTHER PUBLICATIONS

Synthesis and RGD peptide modification of poly{(lactic acid)-co-[glycolic acid)-alt-(L-lysine)]}, Yan et al., Feb. 2008, e-polymers 2008, No. 028, pp. 1-12 (Year: 2008).*

(Continued)

*Primary Examiner* — Jeffrey M Wollschlager
(74) *Attorney, Agent, or Firm* — Sterne, Kessler, Goldstein & Fox P.L.L.C.

(57) ABSTRACT

There is provided a method of producing a bioactive polymer filament, the method comprising: providing a base polymer powder and a bioactive copolymer; mixing the base polymer powder with the bioactive copolymer to obtain a mixture; and extruding a bioactive polymer filament from the mixture at an extrusion temperature profile that is based on a predetermined melt/softening temperature and a predetermined onset degradation temperature of the bioactive polymer; and performing a post-extrusion thermal analysis on the extended bioactive polymer filament to assess onset degradation of the bioactive copolymer in the filament. There is also provided a bioactive polymer filament obtained from said method and a fused filament fabrication (FFF) or fused deposition modelling (FDM) based three-dimensional printing method.

14 Claims, 57 Drawing Sheets

(51) Int. Cl.

| | |
|---|---|
| ***C08F 6/00*** | (2006.01) |
| ***C08G 61/08*** | (2006.01) |
| ***C08G 63/08*** | (2006.01) |
| ***C08L 65/00*** | (2006.01) |

(56) References Cited

U.S. PATENT DOCUMENTS

2008/0319114 A1* 12/2008 Li .......................... A61L 27/18 524/415
2016/0009058 A1* 1/2016 Maziers .................. B29C 41/04 525/190
2016/0177026 A1* 6/2016 Gray, Jr. ................ C08G 63/64 428/221
2018/0042843 A1* 2/2018 Blum ................... A61K 9/1075
2019/0388336 A1* 12/2019 Barrett ................... A61K 47/34
2020/0095374 A1* 3/2020 Skalla ................ C08G 64/0208
2021/0069378 A1 3/2021 Nelson et al.
2022/0072763 A1* 3/2022 Cordero ............... C08G 61/124
2022/0176619 A1* 6/2022 Taylor ................ C08G 64/0208

FOREIGN PATENT DOCUMENTS

TW 201912189 A 4/2019
WO WO-2016023036 A1 2/2016
WO WO2018106738 * 6/2018
WO WO-2019046808 A1 3/2019
WO WO-2022093106 A1 5/2022

OTHER PUBLICATIONS

Pitjamit, S., et al., "The Possibility of Interlocking Nail Fabrication from Fff 3D Printing PLA/PCL/HA Composites Coated by Local Silk Fibroin for Canine Bone Fracture Treatment," Materials (Basel) 13(7):1564, MDPI, Switzerland (Mar. 2020).
Fekete, I., et al., "Toughening of various PLA grades with natural rubber for 3D printing applications," Dec. 2020, Retrieved from the Internet: URL: https://www.researchgate.net/publication/351373823_Toughening_of_various_PLA_grades_with_natural_rubber-for_3D_printing_applications.
International Search Report and Written Opinion for International Application No. PCT/SG2022/050620, Intellectual Property Office of Singapore, Singapore, mailed on Mar. 9, 2023, 12 pages.
Kumar, S., et al., "3D Bioprinting of Nature-Inspired Hydrogel Inks Based on Synthetic Polymers," ACS Apply Polym Mater 3:3685-3701, American Chemical Society, United States (Jul. 2021).
Patel, B.B., et al., "Tunable structural color of bottlebrush block copolymers through direct-write 3D printing from solution," Sci Adv 6(24):eaaz7202, American Association for the Advancement of Science, United States (Jun. 2020).

* cited by examiner

IHC – CD3

Control

IHC – CD3

PA12

IHC – CD3

PA12-(PA6-GPHP)

H&E
Control

H&E
PA12

H&E

PA12-(PA6-GPHP)

IHC – CD3

Control

IHC – CD3

PCL

IHC – CD3

PCL-RGD

IHC – CD3

PCL-GPHP

H&E
Control

H&E
PCL

H&E

PCL-RGD

H&E

PCL-GPHP

IHC – CD3

Control

IHC – CD3

PLA

IHC – CD3

PLA-HA

IHC – CD3

PLA-RGD

IHC – CD3
PLA-GPHP

H&E
Control

H&E
PLA

H&E

PLA-HA

H&E
PLA-RGD

H&E
PLA-GPHP

IHC – CD3

Control

IHC – CD3

PLGA

IHC – CD3

PLGA-RGD10%

IHC – CD3

PLGA-RGD20%

H&E
Control

H&E

PLGA

H&E

PLGA-RGD10%

H&E

PLGA-RGD20%

METHOD OF PRODUCING A BIOACTIVE POLYMER FILAMENT, THE BIOACTIVE POLYMER FILAMENT AND PRINTING METHODS USING THE SAME

TECHNICAL FIELD

The present disclosure relates broadly to a method of producing a bioactive polymer filament. The present disclosure also relates to the bioactive polymer filament and printing methods using said bioactive polymer filament.

BACKGROUND

The adoption of three-dimensional (3D) printing technologies in medicine has the potential of enabling creation of biomedical devices tailored specifically for each patient with an accelerated time to market that hastens the recovery period. 3D printing technologies also allow doctors and patients to better understand the medical case by studying a real-life printed model, using scans taken by computed tomography (CT) and magnetic resonance imaging (MRI).

An extrusion-based 3D printing method known as bioprinting creates parts using bioink in liquid or powder form at low operating temperatures. Bioink typically consists of hydrogels encapsulating live cells and/or biochemical molecules such as extracellular matrix (ECM) components. This promotes cell proliferation which supports tissue growth and organ development. Despite this, printed parts made of bioink have less mechanical advantage as compared to parts made of thermoplastic polymers using other manufacturing methods. Bioink is also volumetrically inconsistent as chemically crosslinked hydrogels which are prepared by covalent bonding undergo great volume change due to material expansion known as Barus effect. Although high polymer concentration hydrogels would provide high shape conformity required, this will limit nutrient & waste transportation and prevent network remodeling & construct integration which renders it biologically incompetent. Furthermore, obtaining the suitable properties by tuning chemical, physical and/or enzymatic mechanisms remain as a challenge for hydrogels as it requires an intricate balance in both physical and biological competence.

Other 3D printing technologies such as stereolithography (SLA), selective laser sintering (SLS) and multi jet fusion (MJF) have drawbacks too significant for successful translation to medical applications. For instance, SLA only accepts photopolymeric resin (liquid), which is typically a thermoset polymer that requires curing by UV light and which is chemically significantly different from the medically approved bioactive polymers that have been developed. Furthermore, parts which are made by SLA method pose cytotoxicity risk if there are any residual photoinitiator and/or uncured resin present when these parts are introduced inside a patient.

For SLS, it is a costly printing technology which likewise also uses powdered materials. Parts printed by this method produces powdery surface finish which signifies presence of loose material. Again, this poses a health risk which may cause complications for the patient if any of the loose material gets into the bloodstream directly, which in turn may cause inflammation.

Lastly, MJF is based on binder technology which also uses powdered material and binding agent to agglutinate the powdered material together. Parts printed by MJF are severely compromised mechanically as the bulk of the mechanical strength comes from the binding agent instead of the powdered material. Presence of high porosity in the printed part further compromises its mechanical properties.

In view of the above, there is a need to address or at least ameliorate the above-mentioned problems. In particular, there is a need to provide a bioactive material/feedstock suitable for use in 3D printing methods to obtain structures with desirable biocompatibility, bioactivity and mechanical properties that address or at least ameliorate the above-mentioned problems. There is also a need to provide a method of producing such a bioactive material/feedstock.

SUMMARY

In one aspect, there is provided a method of producing a bioactive polymer filament, the method comprising:

- providing a base polymer powder and a bioactive copolymer;
- mixing the base polymer powder with the bioactive copolymer to obtain a mixture; and
- extruding a bioactive polymer filament from the mixture at an extrusion temperature profile that is based on a predetermined melt/softening temperature and a predetermined onset degradation temperature of the bioactive polymer; and
- performing a post-extrusion thermal analysis on the extruded bioactive polymer filament to assess onset degradation of the bioactive polymer in the filament.

In one embodiment, the bioactive copolymer is acellular.

In one embodiment, the bioactive copolymer is obtained by ring-opening metathesis polymerisation (ROMP).

In one embodiment, the bioactive copolymer is a bioactive synthetic copolymer with a poly(norbornene) backbone comprising one or more repeating units represented by general formula (I) and one or more repeating units represented by general formula (II):

(I)

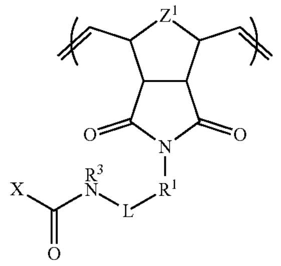

(II)

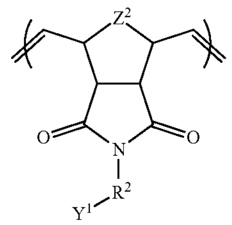

wherein $R^1$ is optionally substituted alkyl;

$R^2$ is selected from a single bond, optionally substituted alkyl, optionally substituted alkenyl, optionally substituted alkynyl, optionally substituted alkoxyalkyl, optionally substituted alkylcarbonyl or optionally substituted alkylcarbonylalkyl;

$R^3$ is selected from H, optionally substituted alkyl, optionally substituted alkenyl or optionally substituted alkynyl;

L is heteroalkylene;

X comprises a bioactive moiety selected from the group consisting of proteins, peptides, carbohydrates, collagen, hyaluronic acid, therapeutic/drug molecules and derivatives thereof;

$Y^1$ comprises a synthetic polymer or parts thereof; and $Z^1$ and $Z^2$ are each independently selected from $CR^aR^b$, O, $NR^c$, $SiR^aR^b$, $PR^a$ or S, wherein $R^a$, $R^b$ and $R^c$ are each independently selected from the group consisting of H, optionally substituted alkyl, optionally substituted alkenyl and optionally substituted alkynyl.

In one embodiment, $Y^1$ is represented by general formula (III):

(III)

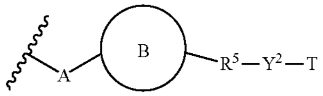

wherein

A is selected from a single bond, oxy, carbonyl, oxycarbonyl, carboxyl, optionally substituted alkoxy, optionally substituted alkoxyalkyl, optionally substituted alkylcarbonyl, optionally substituted alkylcarbonylalkyl, optionally substituted carboxyalkyl, optionally substituted oxycarbonylalkyl, optionally substituted alkylcarboxylalkyl, optionally substituted alkoxycarbonylalkyl, N or $NR^c$ wherein $R^c$ is independently selected from H, optionally substituted alkyl, optionally substituted alkenyl or optionally substituted alkynyl;

B is optionally present as a ring selected from 1,2,3-triazole or succinimide;

$R^5$ is selected from a single bond, optionally substituted alkyl, optionally substituted alkenyl, optionally substituted alkynyl, optionally substituted alkoxyalkyl, optionally substituted alkylcarbonyl or optionally substituted alkylcarbonylalkyl;

$Y^2$ is selected from the group consisting of polypropylene (PP), polyesters, poly(lactic acid) (PLA), poly(lactic-co-glycolic acid) (PLGA), poly(caprolactone) (PCL), polystyrene (PS), polyacrylates, poly(meth)acrylates, polyamides (PA), polyurethane (PU), and parts thereof; and T is a terminal group selected from the group consisting of hydrogen, halogen, hydroxyl, amino, acyl, thiol, optionally substituted alkyl, optionally substituted alkenyl, optionally substituted alkynyl, optionally substituted alkoxy, optionally substituted alkoxyalkyl, optionally substituted alkylcarbonyl, optionally substituted alkylcarbonylalkyl, optionally substituted carboxyalkyl, optionally substituted oxycarbonylalkyl, optionally substituted alkylcarboxylalkyl or optionally substituted alkoxycarbonylalkyl.

In one embodiment, $Y^1$ is selected from the following general formulae (IIIa), (IIIb), (IIIc), (IIId), (IIIe), (IIIf), or (IIIg):

(IIIa)

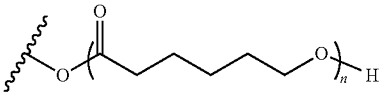

(IIIb)

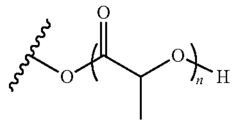

(IIIc)

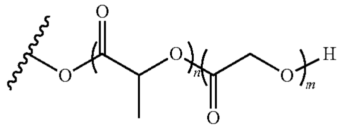

(IIId)

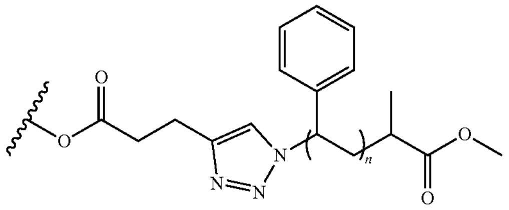

(IIIe)

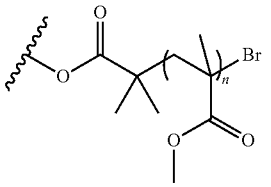

(IIIf)

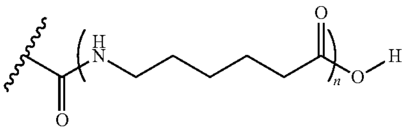

(IIIg)

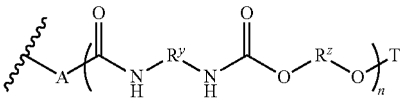

wherein $R^y$ is selected from an alkyl, aryl or biaryl;

$R^z$ is alkyl;

A is 0 or $NR^c$ wherein $R^c$ is independently selected from H, optionally substituted alkyl, optionally substituted alkenyl or optionally substituted alkynyl;

T is a terminal group selected from the group consisting of hydrogen and methyl;

$n \geq 1$; and $m \geq 1$.

In one embodiment, the base polymer powder is obtained from cryogenic milling of base polymer pellets.

In one embodiment, the base polymer powder has an average particle size of no more than 1 mm.

In one embodiment, the post-extrusion thermal analysis comprises application of thermogravimetric analysis (TGA) and differential scanning calorimetry (DSC).

In one embodiment, the extruding is performed using an extruder having one or more rotating screws.

In one embodiment, the extruded bioactive polymer filament has a filament diameter falling in the range of from 1.5 mm to 4.0 mm.

In one embodiment, the method further comprising performing a pre-extrusion thermal analysis on the base polymer and/or bioactive copolymer to determine the melt temperature and the onset degradation temperature of the bioactive polymer.

In one embodiment, the base polymer and bioactive copolymer have been vacuum dried prior to mixing.

In one embodiment, the mixture of base polymer and bioactive copolymer comprises 60.0 wt % to 99.9 wt % of the base polymer and 0.1 wt % to 40.0 wt % of the bioactive copolymer.

In one embodiment, the base polymer is selected from the group consisting of polypropylene (PP), polyesters, poly(lactic acid) (PLA), poly(lactic-co-glycolic acid) (PLGA), poly(caprolactone) (PCL), polystyrene (PS), polyacrylates, poly(meth)acrylates, polyamides (PA), polyurethane (PU) and combinations thereof.

In one aspect, there is provided a bioactive polymer filament obtained from the method disclosed herein.

In one aspect, there is provided a fused filament fabrication (FFF) or fused deposition modelling (FDM) based three-dimensional printing method, the method comprising:

feeding a bioactive polymer filament disclosed herein into a FFF or FDM based three-dimensional printing apparatus;

applying heat to bioactive polymer filament to obtain a molten form of the bioactive polymer; and depositing the molten bioactive polymer on a print bed to form a printed three-dimensional part or structure.

In one embodiment, the method further comprising performing one or more of post-printing analysis of the printed three-dimensional part or structure, the post-printing analysis selected from the group consisting of:

i. a mechanical analysis of the printed three-dimensional part or structure to assess its mechanical properties;
ii. a biocompatibility analysis of the printed three-dimensional part or structure to assess its biocompatibility with living cells;
iii. a thermal analysis on the printed three-dimensional part or structure to assess onset degradation of the bioactive polymer in the printed three-dimensional part or structure; and
iv. a spectrometric analysis of the printed three-dimensional part or structure to assess the presence of bioactive copolymer in the printed three-dimensional part or structure.

In one embodiment, the step of applying heat is at a temperature that is based on a predetermined melt/softening temperature and a predetermined onset degradation temperature of the bioactive polymer.

In one embodiment, the FFF or FDM based three-dimensional printing apparatus is configured for filament feedstock having filament diameters falling in the range of from 1.5 mm to 4.0 mm.

Definitions

The term "bioactive" or the like as used herein broadly refers to the ability of having an effect or interaction, or response, preferably desirable or positive, on or from a living cell or tissue. These effects may include but are not limited to these effects tissue uptake, metabolism, or physiological response. Bioactivity can be assessed from methodologies in vivo (animal or human studies), or ex vivo/in vitro (e.g. cell or tissue cultures in laboratory conditions. In various embodiments of the bioactive copolymers or bioactive polymer filament disclosed herein, the biological effects are typically positive and desirable, such as improving cellular growth etc.

The term "biocompatible" as used herein broadly refers to a property of being compatible with biological systems or parts of the biological systems without substantially or significantly eliciting an adverse physiological response such as a toxic reaction, an immune reaction, an injury or the like. Such biological systems or parts include blood, cells, tissues, organs or the like.

The term "polymer" as used herein refers to a chemical compound comprising repeating units and is created through a process of polymerization. The units composing the polymer are typically derived from monomers and/or macromonomers. A polymer typically comprises repetition of a number of constitutional units.

The terms "monomer" or "macromonomer" as used herein refer to a chemical entity that may be covalently linked to one or more of such entities to form a polymer.

The term "bond" refers to a linkage between atoms in a compound or molecule. The bond may be a single bond, a double bond, or a triple bond.

In the definitions of a number of substituents below, it is stated that "the group may be a terminal group or a bridging group". This is intended to signify that the use of the term is intended to encompass the situation where the group is a terminal group/moiety as well as the situation where the group is a linker between two other portions of the molecule. Using the term "alkyl" having 1 carbon atom as an example, it will be appreciated that when existing as a terminal group, the term "alkyl" having 1 carbon atom may mean $—CH_3$ and when existing as a bridging group, the term "alkyl" having 1 carbon atom may mean $—CH_2—$ or the like.

The term "alkyl" as a group or part of a group refers to a straight or branched aliphatic hydrocarbon group having 1 to 20 carbon atoms, 1 to 10 carbon atoms, 1 to 6 carbon atoms, or 1, 2, 3, 4, 5, 6, 7, 8, 9, 10, 11, 12, 13, 14, 15, 16, 17, 18, 19 or 20 carbon atoms. Examples of suitable straight and branched alkyl substituents include methyl, ethyl, n-propyl, 2-propyl, isopropyl, n-butyl, isobutyl, sec-butyl, t-butyl, hexyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl and the like. The group may be a terminal group or a bridging group.

The term "alkenyl" as a group or part of a group denotes an aliphatic hydrocarbon group containing at least one carbon-carbon double bond and which may be straight or branched having 2 to 20 carbon atoms, 2 to 10 carbon atoms, 2 to 6 carbon atoms, or 2, 3, 4, 5, 6, 7, 8, 9, 10, 11, 12, 13, 14, 15, 16, 17, 18, 19 or 20 carbon atoms in the chain. The group may contain a plurality of double bonds and the orientation about each double bond is independently E or Z. Exemplary alkenyl groups include, but are not limited to, ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. The group may be a terminal group or a bridging group.

The term "alkynyl" as a group or part of a group denotes an aliphatic hydrocarbon group containing at least one carbon-carbon triple bond and which may be straight or branched having 2 to 20 carbon atoms, 2 to 10 carbon atoms, 2 to 6 carbon atoms, or 2, 3, 4, 5, 6, 7, 8, 9, 10, 11, 12, 13, 14, 15, 16, 17, 18, 19 or 20 carbon atoms in the chain. The group may contain a plurality of triple bonds. Exemplary alkynyl groups include, but are not limited to, acetylenyl, propynyl, 1-butynyl, 2-butynyl, 3-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like. The group may be a terminal group or a bridging group.

The term "alkylene" as used herein is intended to broadly refer to an aliphatic hydrocarbon group (e.g., alkyl, alkenyl or alkynyl as defined herein) that is divalent. The alkylene groups may be linear, branched, saturated, unsaturated, cyclic, acyclic, substituted and/or unsubstituted. Examples of alkylene include methylene (i.e. $—CH_2—$ or "alkylene" having 1 carbon atom), ethylene (i.e. $—CH_2CH_2—$ or "alkylene" having 2 carbon atoms), propylene (i.e. "alkylene" having 3 carbon atoms) and the like.

The term "heteroalkylene" as used herein refers to alkylene having one or more $—CH_2—$ replaced with a heteroatom selected from 0, NR, Si, P or S, where R is hydrogen or alkyl as defined herein. The term "heteroalkylene" can be linear, branched or cyclic and containing up to 500 carbon atoms.

The term "aryl" as a group or part of a group as used herein refers to (i) an optionally substituted monocyclic, or fused polycyclic, aromatic carbocycle (ring structure having ring atoms that are all carbon) preferably having from 5 to 12, or 5, 6, 7, 8, 9, 10, 11, or 12 carbon atoms per ring; (ii) an optionally substituted partially saturated bicyclic aromatic carbocyclic moiety in which a phenyl and a $—C_{5-7}$-cycloakyl or $—C_{5-7}$-cycloalkenyl groups are fused together to form a cyclic structure, such as tetrahydronaphthyl, indenyl or indanyl. The group may be a terminal group or a bridging group. Examples of aryl groups include $C_6$-$C_{18}$ aryl group such as phenyl, naphthyl, and the like. The term "biaryl" as used herein refers to a bicyclic "aryl" as defined herein.

The term "alkoxy" as used herein refers to straight chain or branched alkyloxy groups. Examples include methoxy, ethoxy, n-propoxy, isopropoxy, tert-butoxy, and the like.

The term "alkoxyalkyl" as used herein is intended to broadly refer to a group containing —R—O—R', where R and R' are alkyl as defined herein. The group may be a terminal group or a bridging group.

The term "alkylcarbonyl" as used herein is intended to broadly refer to a group containing —R—C(═O)—, where R is alkyl as defined herein. The group may be a terminal group or a bridging group.

The term "alkylcarbonylalkyl" as used herein is intended to broadly refer to a group containing —R—C(═O)—R', where R and R' are alkyl as defined herein. The group may be a terminal group or a bridging group.

The term "carboxylalkyl" as used herein is intended to broadly refer to a group containing —C(═O)—O—R, where R is alkyl as defined herein. The group may be a terminal group or a bridging group.

The term "oxycarbonylalkyl" as used herein is intended to broadly refer to a group containing —O—C(═O)—R, where R is alkyl as defined herein. The group may be a terminal group or a bridging group.

The term "alkylcarboxylalkyl" as used herein is intended to broadly refer to a group containing —R—C(═O)—O—R', where R and R' are alkyl as defined herein. The group may be a terminal group or a bridging group.

The term "alkoxycarbonylalkyl" as used herein is intended to broadly refer to a group containing —R—O—C(═O)—R', where R and R' are alkyl as defined herein. The group may be a terminal group or a bridging group.

The term "oxy" as used herein is intended to broadly refer to a group containing —O—.

The term "carbonyl" as used herein is intended to broadly refer to a group containing —C(═O)—.

The term "oxycarbonyl" as used herein is intended to broadly refer to a group containing —O—C(═O)—.

The term "carboxyl" as used herein is intended to broadly refer to a group containing —C(═O)—O—R, where R is hydrogen or an organic group.

The term "halogen" represents chlorine, fluorine, bromine or iodine. The term "halo" represents chloro, fluoro, bromo or iodo.

The term "amine group" or the like is intended to broadly refer to a group containing $—NR_2$, where R is independently a hydrogen or an organic group. The group may be a terminal group or a bridging group.

The term "amide group" or the like is intended to broadly refer to a group containing $—C(═O)NR_2$, where R is independently a hydrogen or an organic group. The group may be a terminal group or a bridging group.

The term "heterocyclic" as used herein broadly refers to a structure where two or more different kinds of atoms are connected to form at least one ring. For example, a heterocyclic ring may be formed by carbon atoms and at least another atom (i.e. heteroatom) selected from oxygen (O), nitrogen (N) or (NR) and sulfur (S), where R is independently a hydrogen or an organic group. The term also includes, but is not limited to, saturated and unsaturated 5-membered, and saturated and unsaturated 6-membered rings. Examples of groups having a heterocyclic structure include, but are not limited to furan, thiophene, 1H-pyrrole, 2H-pyrrole, 1-pyrroline, 2-pyrroline, 3-pyrroline, 1-pyrazoline, 2-pyrazoline, 3-pyrazoline, 2-imidazoline, 3-imidazoline, 4-imidazoline, pyrazole, imidazole, oxazole, isoxazole, thiazole, isothiazole, 1,2,3-triazole, 1,2,4-triazole, 1,2,3-oxadiazole, disubstituted 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, tetrahydrofuran, tetrahydrothiophene, pyrrolidine, 1,3-dioxolane, 1,2-oxathiolane, 1,3-oxathiolane, pyrazolidine, imidazolidine, pyridine, pyridazine, pyrimidine, pyrazine, 1,2-oxazine, 1,3-oxazine, 1,4-oxazine, thiazine, 1,2,3-triazine, 1,2,4-triazine, 1,3,5-triazine, 2H-pyran, 4H-pyran, 2-pyrone, 4-pyrone, 1,4-dioxin, 2H-thiopyran, 4H-thiopyran, tetrahydropyran, thiane, piperidine, 1,4-dioxane, 1,2-dithiane, 1,3-dithiane, 1,4-dithiane, 1,3,5-trithiane, piperazine, morpholine, thiomorpholine and the like.

The term "poly(alkylene glycol)" as used herein is intended to broadly refer to a polymer containing an ether group (i.e. —O—R—, where R is alkylene as defined herein) in a repeating unit. In various embodiments, the terms poly(alkylene glycol) may be used interchangeably with the terms "polyglycol", "polyether" or "poly(alkylene oxide)". Examples of poly(alkylene glycol) include poly (ethylene glycol) (PEG) (or polyethylene oxide), poly(propylene glycol) (PPG) (or polypropylene oxide), poly(butylene glycol) (or polybutylene oxide) and the like.

The term "substituted," when used to describe a chemical structure or moiety, refers to the chemical structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl-or-alkylNHC(O)alkyl), amine (such as alkylamino, arylamino, arylalkylamino), aryl, aryloxy, azo, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., $—CCl_3$, $—CF_3$, $—C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

The term "micro" as used herein is to be interpreted broadly to include dimensions from about 1 micron to about 1000 microns.

The term "nano" as used herein is to be interpreted broadly to include dimensions less than about 1000 nm, less than about 500 nm, less than about 100 nm or less than about 50 nm.

The terms "coupled" or "connected" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed there-between.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. It is to be appreciated that the individual numerical values within the range also include integers, fractions and decimals. Furthermore, whenever a range has been described, it is also intended that the range covers and teaches values of up to 2 additional decimal places or significant figures (where appropriate) from the shown numerical end points. For example, a description of a range of 1% to 5% is intended to have specifically disclosed the ranges 1.00% to 5.00% and also 1.0% to 5.0% and all their intermediate values (such as 1.01%, 1.02% . . . 4.98%, 4.99%, 5.00% and 1.1%, 1.2% . . . 4.8%, 4.9%, 5.0% etc.,) spanning the ranges. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DESCRIPTION OF EMBODIMENTS

Exemplary, non-limiting embodiments of a method of producing a bioactive polymer filament, said bioactive polymer filament and a method of using the bioactive polymer filament for three-dimensional printing are disclosed hereinafter.

Method of Producing a Bioactive Polymer Filament

In various embodiments, there is provided a method of producing a bioactive polymer filament, the method comprising providing a base polymer powder and a bioactive copolymer; mixing/blending the base polymer powder with the bioactive copolymer to obtain a formulation/mixture; and extruding a bioactive polymer filament from the formulation/mixture at an extrusion temperature profile that is based on a predetermined melt/softening temperature and a predetermined onset degradation temperature of the bioactive polymer. In various embodiments, the extrusion temperature profile is based on a predetermined melt/softening temperature of the base polymer or the bioactive polymer, whichever is higher. For example, if the melt temperature of the base polymer is higher than the melt temperature of the bioactive polymer, then the extrusion temperature profile is based on the predetermined melt/softening temperature of the base polymer, and vice versa.

In various embodiments, the bioactive copolymer is present in powdered form. Accordingly, it will be appreciated that no additional/further step may be required/necessary to convert the bioactive copolymer into powdered form.

In various embodiments, the bioactive polymer filament is suitable for use as a feedstock for fused filament fabrication (FFF) or fused deposition modelling (FDM) based 3D printing. FFF is an extrusion-based 3D printing technology which generally utilizes polymer filament feedstock. It deposits the molten polymer in 2-dimensional plane according to the deposition path set by the machine over several layers until the part is fully printed in 3-dimensional space. FFF technology typically uses filaments made of thermoplastic polymers where heat transfer characteristics and rheology are important properties required for good quality printed parts. FFF is preferred over other 3D printing technology as it enables good control over printing parameters which can influence the mechanical properties. However, due to high temperature utilized in FFF technology, living cells or other temperature-sensitive biological molecules cannot be incorporated in its filament as it would denature the proteins, degrade polysaccharides or oligopeptides and kill the cells. Advantageously, various embodiments of the bioactive polymer filament disclosed herein provide desirable mechanical as well as biological characteristics that makes its suitable for use in printing medical-related structures using FFF 3D printing technologies.

In various embodiments, the bioactive polymer filament and/or bioactive copolymer is acellular or is substantially devoid of cells. Advantageously, in various embodiments, the bioactive polymer filament and/or bioactive copolymer do not rely on highly temperature sensitive biological moieties like stem cells or growth factors to impart bioactivity since these biological moieties are highly susceptible to cell death during the extrusion process to form the filament feedstock. Even more advantageously, embodiments of the bioactive polymer filament and/or bioactive copolymer are still able to stimulate host cells to proliferate which promotes tissue growth.

In various embodiments, the bioactive copolymer comprises biological molecules or biomolecules that are bonded/linked (e.g., chemically bonded/linked) to/on the bioactive copolymer. It will be appreciated that in various embodiments, the bioactive polymer filament and/or bioactive copolymer is substantially devoid of free (or unbound/unbonded/unlinked) biomolecules such as free (or unbound/unbonded/unlinked) oligopeptides or oligosaccharides.

In various embodiments, the method additionally comprises performing a post-extrusion thermal analysis on the extruded bioactive polymer filament to assess onset degradation of the bioactive polymer/copolymer in the filament. It will be appreciated that extrusion is a thermomechanical process which involves high heat and high shearing which can degrade polymers, which in turn may lead a change in thermal behaviour. A change in thermal behaviour may be related to a change in molecular weight which directly affects mechanical properties and melt flow behaviour of the material subsequently. For example, the synthetic polymer side chain in the bioadditive/bioactive copolymer may be of a lower molecular weight relative to the base polymer in various embodiments and this may result in it being susceptible to degradation due to extrusion process. Thus, performing a post-extrusion thermal analysis on the extruded bioactive polymer filament to ensure non-degradation of bioadditive/bioactive copolymer after filament extrusion process advantageously ensures the quality of filament before 3D printing.

In various embodiments, the bioactive copolymer is obtained by ring-opening metathesis polymerisation (ROMP). For example, the bioactive copolymer is a copolymer of biological molecules and synthetic polymer prepared by the ROMP method. The synthetic polymer may or may not be similar to that of the base polymer used. Biological molecules such as collagen, peptides (e.g., oligopeptides), sugar molecules (e.g., oligosaccharides) and hyaluronic acid may be preferred in some embodiments. Further examples of the bioactive copolymer are provided below.

In various embodiments, the term "bioactive copolymer" is used interchangeably with the term "bioadditive" and are intended to cover a copolymer of biological molecules and synthetic polymer prepared by the ROMP method.

In various embodiments, the base polymer powder is obtained from physical processes to reduce the size of base polymer pellets. Such physical processes may comprise grinding, pulverizing, milling, cryogenic milling/cryomilling or combinations thereof to obtain the powdered base polymer. Accordingly, in various embodiments, the method may further comprise performing one or more of grinding, pulverizing, milling, cryogenic milling/cryomilling of base polymer pellets to obtain base polymer powder. In one example, the base polymer powder is obtained from cryogenic milling/cryomilling of the base polymer pellets. The cryomiling/cryogenic milling may be performed in the presence of a cryogenic liquid selected from the group consisting of argon, helium, hydrogen, nitrogen and oxygen. Advantageously, using cryomilling/cryogenic milling/grinding in embodiments of the method disclosed herein aids in embrittlement process and/or prevents degradation of the polymer. It will be appreciated that the cryogen/cryogenic liquid used (e.g., liquid nitrogen) can lower the temperature significantly (<−196 °C) which in turn may induce embrittlement on the polymer/material, and subsequently easing the milling process. It will also be appreciated that the cryogen/cryogenic liquid used can prevent any thermal degradation of the polymer/material from occurring during the high-energy milling process.

In various embodiments, the base polymer powder has an average particle size of no more than about 1 mm, from about 0.50 mm to about 1 mm, from about 0.55 mm to about 0.95 mm, from about 0.50 mm to about 0.90 mm, from about 0.50 mm to about 0.85 mm, from about 0.50 mm to about 0.80 mm, from about 0.60 mm to about 1 mm, from about 0.65 mm to about 1 mm, or from about 0.70 mm to about 0.95 mm. In various embodiments, the base polymer powder has an average particle size of from about 0.10 mm to about 1.00 mm, from about 0.11 mm to about 0.99 mm, from about 0.12 mm to about 0.98 mm, from about 0.13 mm to about 0.97 mm, from about 0.14 mm to about 0.96 mm, from about 0.15 mm to about 0.95 mm, from about 0.20 mm to about 0.90 mm, from about 0.25 mm to about 0.85 mm, from about 0.30 mm to about 0.80 mm, from about 0.35 mm to about 0.75 mm, from about 0.40 mm to about 0.70 mm, from about 0.45 mm to about 0.65 mm, from about 0.50 mm to about 0.60 mm, from about 0.51 mm to about 0.59 mm, from about 0.52 mm to about 0.58 mm, from about 0.53 mm to about 0.57 mm, from about 0.54 mm to about 0.56 mm, or about 0.55 mm.

In various embodiments, the base polymer and/or bioactive copolymer have been dried (e.g. vacuum dried) prior to mixing. Accordingly, in various embodiments, the method further comprises drying (e.g. vacuum drying) the base polymer and/or bioactive copolymer prior to mixing them. For example, after cryomiling/cryogenic milling is carried out on base polymer pellets to obtain base polymer powder, the base polymer powder is dried (e.g. vacuum dried) prior to mixing with the bioactive copolymer. Advantageously, vacuum drying provides an inert environment whereby moisture may be reduced significantly allowing for more effective drying. Additionally, since airflow is absent in vacuum drying, materials in powder form are not blown around which would otherwise result in material loss. The drying step may be performed at an ambient or room temperature or at temperature of from about 35 °C to about 100 °C, from about 40 °C to about 95 °C, from about 45 °C to about 90 °C, from about 40 °C to about 85 °C or from about 45 °C to about 80 °C. The drying step may be performed over a time period of about 4 hours, about 5 hours, about 6 hours, about 7 hours, about 8 hours, about 9 hours, about 10 hours, about 11 hours, about 12 hours, from about 4 hours to about 12 hours, about 24 hours, about 36 hours, or about 48 hours. In various embodiments, the drying step comprises vacuum drying at a drying pressure of from about −50 mmHg to about −10 mmHg, from about −40 mmHg to about −20 mmHg, or about −40 mmHg.

In various embodiments, the method further comprises performing a pre-extrusion thermal analysis on the bioactive copolymer and/or base polymer to determine the melt temperature and the onset degradation temperature of the bioactive polymer/copolymer and/or base polymer.

The method may further comprise performing thermal analysis on base polymer pellets prior to reducing their sizes (e.g. cryogenic milling/cryomilling) to obtain powdered forms and optionally performing thermal analysis on base polymer pellets after the powdered forms are obtained (e.g. cryogenic milling/cryomilling). Advantageously, the thermal analysis may be useful to determine the thermal properties of the base polymer prior to size reduction (e.g. cryogenic milling/cryomilling) and/or after size reduction and/or prior to filament extrusion so that a benchmark may be obtained and an assessment may be made on whether there is a detraction in the physical and/or thermal properties of the subsequently obtained filament feedstock or printed structure from that expected (e.g. based on the original mechanical properties of the base polymer). The thermal analysis may also provide useful information on the melting temperature (if any) and/or degradation temperature of the base polymer (e.g. pellet form or powdered form) so that the extrusion temperature profile may be customised for the particular base polymer e.g. based on the melt temperature and the onset degradation temperature of the base polymer that were determined. For instance, the extrusion temperature profile may be customised such that the extrusion temperature is between the melting/softening temperature and degradation temperature of the base polymer. It will also be appreciated that in some embodiments, the determination of the melting/softening temperature and degradation temperature of the base polymer may have already been completed previously or such information are already readily available for known/established polymers. Thus, in such embodiments, it may be optional for the presently disclosed method to have such active determination steps.

Similarly, the method may further comprise performing thermal analysis on bioactive copolymer prior to mixing with the base polymer and/or prior to filament extrusion. Advantageously, the thermal analysis may be useful to determine the thermal properties of the bioactive copolymer prior to mixing with the base polymer and/or prior to filament extrusion so that a benchmark may be obtained and an assessment may be made on whether there is a detraction in the physical and/or thermal properties of the subsequently obtained filament feedstock or printed structure that expected (e.g. based on the properties of the bioactive copolymer prior to extrusion). The thermal analysis may also provide useful information on the melting temperature and/or degradation temperature of the bioactive polymer/copolymer so that the extrusion temperature profile may be customised for the particular bioactive copolymer e.g. based on the melt temperature and the onset degradation temperature of the base polymer that were determined. For instance, the extrusion temperature profile may be customised such that the extrusion temperature is between the melting/softening temperature and degradation temperature of the bioactive polymer/copolymer. In various embodiments, such active determination steps are present in the method disclosed herein. Advantageously, adopting/employing such active determination steps in the method disclosed herein prevents degradation of the bioactive polymer/copolymer during filament extrusion and preserves bioactivity of the bioactive copolymer/bioadditive in the filament. As biomolecules linked/bonded to/on the polymer may be lost/melted/degraded during heat treatment, it may therefore be important to determine the temperature(s) at which such situation(s) may occur. It will also be appreciated that in some embodiments, the determination of the melting/softening temperature and degradation temperature of the bioactive polymer/copolymer may have already been completed previously or such information are already readily available for such polymers. Thus, in such embodiments, it may be optional for the presently disclosed method to have such active determination steps.

In various embodiments, the extrusion temperature profile is based on predetermined melt/softening temperatures and predetermined onset degradation temperatures of both the base polymer and the bioactive polymer. Accordingly, the extrusion temperature profile may be customised such that the extrusion temperature is between the melting/softening temperature and onset degradation temperature of the bioactive copolymer and also between the melting/softening temperature and onset degradation temperature of the base polymer (e.g. base polymer powder).

In various embodiments, the thermal analysis disclosed herein comprises one or more of thermogravimetric analysis (TGA) and differential scanning calorimetry (DSC). In various embodiments, the thermal analysis comprises application of TGA and DSC. The application of TGA and DSC may be non-simultaneous or simultaneous. For example, the thermal analysis comprising TGA and DSC may be performed either non-simultaneously (e.g., TGA-DSC) or simultaneously (e.g., STA). In various embodiments, the thermal analysis comprises simultaneous thermal analysis (STA) through the simultaneous application of TGA and DSC. For example, the post-extrusion thermal analysis may comprise STA.

In various embodiments, the extruding is performed using an extruder having one or more rotating screws. The extruder may have one or more, or two or more rotating screws. For example, the extruder may be a single screw extruder. Advantageously, as opposed to a single screw extruder, an extruder with two or more rotating screws may achieve good and uniform mixing/blending of the base polymer and bioactive copolymer. In one example, the extruder is a twin screw extruder (TSE). In another example, the extruder is a multi-screw extruder. The twin screw and/or multi-screw extruder may be intermeshing or non-intermeshing and co-rotating or counter-rotating. Each screw may be made of multiple screw elements to support either feeding, mixing or discharging. In various embodiments, the mixing elements along each screw offers a unique advantage as it kneads the molten blended materials to achieve homogeneity. For example, in various embodiments, these elements form at three different segments along each screw, granting a thorough mixing process.

In various embodiments, the extruder comprises a melt pump for building pressure and for ensuring constant output. The nozzle size of the extruder or melt pump of the extruder may have a diameter that allows for a filament diameter falling in the range of from about 1.5 mm to about 4.0 mm, from about 1.6 mm to about 3.9 mm, from about 1.7 mm to about 3.5 mm, from about 1.71 mm to about 3.4 mm, from about 1.72 mm to about 3.3 mm, from about 1.73 mm to about 3.2 mm, from about 1.74 mm to about 3.1 mm, from about 1.75 mm to about 3.0 mm, from about 1.76 mm to about 2.95 mm, from about 1.77 mm to about 2.90 mm, from about 1.78 mm to about 2.88 mm, from about 1.79 mm to about 2.86 mm, or from about 1.80 mm to about 2.85 mm to be produced. The extruder or melt pump of the extruder may have a nozzle diameter that falls in the range of from about 1 mm to about 4 mm, about 1 mm, about 1.5 mm, about 2 mm, about 2.5 mm, about 3 mm, about 3.5 mm or about 4 mm. The extruder or melt pump of the extruder may have a nozzle diameter that falls in the range of from about 1.00 mm to about 4.00 mm, from about 1.05 mm to about 3.95 mm, from about 1.10 mm to about 3.90 mm, from about 1.15 mm to about 3.85 mm, from about 1.20 mm to about 3.80 mm, from about 1.25 mm to about 3.75 mm, from about 1.30 mm to about 3.70 mm, from about 1.35 mm to about 3.65 mm, from about 1.40 mm to about 3.60 mm, from about 1.45 mm to about 3.55 mm, from about 1.50 mm to about 3.50 mm, from about 1.55 mm to about 3.45 mm, from about 1.60 mm to about 3.40 mm, from about 1.65 mm to about 3.35 mm, from about 1.70 mm to about 3.30 mm, from about 1.75 mm to about 3.25 mm, from about 1.80 mm to about 3.20 mm, from about 1.85 mm to about 3.15 mm, from about 1.90 mm to about 3.10 mm, from about 1.95 mm to about 3.05 mm, from about 2.00 mm to about 3.00 mm, from about 2.05 mm to about 2.95 mm, from about 2.10 mm to about 2.90 mm, from about 2.15 mm to about 2.85 mm, from about 2.20 mm to about 2.80 mm, from about 2.25 mm to about 2.75 mm, from about 2.30 mm to about 2.70 mm, from about 2.35 mm to about 2.65 mm, from about 2.40 mm to about 2.60 mm, from about 2.45 mm to about 2.55 mm, or about 2.50 mm.

In various embodiments, the extruded bioactive polymer filament has a filament diameter falling in the range of from about 1.5 mm to about 4.0 mm, from about 1.6 mm to about 3.9 mm, from about 1.7 mm to about 3.5 mm, from about 1.71 mm to about 3.4 mm, from about 1.72 mm to about 3.3 mm, from about 1.73 mm to about 3.2 mm, from about 1.74 mm to about 3.1 mm, from about 1.75 mm to about 3.0 mm, from about 1.76 mm to about 2.95 mm, from about 1.77 mm to about 2.90 mm, from about 1.78 mm to about 2.88 mm, from about 1.79 mm to about 2.86 mm, or from about 1.80 mm to about 2.85 mm.

The extruder may further comprise a water bath and/or haul unit.

In various embodiments, the formulation/mixture of base polymer and bioactive copolymer comprises from about 60.0 wt % to about 99.9 wt %, from about 61.0 wt % to about 99.8 wt %, from about 62.0 wt % to about 99.7 wt %, from about 63.0 wt % to about 99.6 wt %, from about 64.0 wt % to about 99.5 wt %, from about 65.0 wt % to about 99.0 wt %, from about 66.0 wt % to about 98.5 wt %, from about 67.0 wt % to about 98.0 wt %, from about 68.0 wt % to about 97.0 wt %, from about 69.0 wt % to about 96.0 wt %, from about 70.0 wt % to about 95.0 wt %, from about 71.0 wt % to about 94.0 wt %, from about 72.0 wt % to about 93.0 wt %, from about 73.0 wt % to about 92.0 wt %, from about 74.0 wt % to about 91.0 wt %, from about 75.0 wt % to about 90.0 wt %, from about 76.0 wt % to about 89.0 wt %, from about 77.0 wt % to about 88.0 wt %, from about 78.0 wt % to about 87.0 wt %, from about 79.0 wt % to about 86.0 wt %, from about 80.0 wt % to about 85.0 wt %, from about 81.0 wt % to about 84.0 wt %, or from about 82.0 wt % to about 83.0 wt % of the base polymer.

In various embodiments, the formulation/mixture of base polymer and bioactive copolymer comprises from about 0.1 wt % to about 40.0 wt %, from about 0.1 wt % to about 39.0 wt %, from about 0.2 wt % to about 38.0 wt %, from about 0.3 wt % to about 37.0 wt %, from about 0.4 wt % to about 36.0 wt %, from about 0.5 wt % to about 35.0 wt %, from about 1.0 wt % to about 34.0 wt %, from about 1.5 wt % to about 33.0 wt %, from about 2.0 wt % to about 32.0 wt %, from about 3.0 wt % to about 31.0 wt %, from about 4.0 wt % to about 30.0 wt %, from about 5.0 wt % to about 29.0 wt %, from about 6.0 wt % to about 28.0 wt %, from about 7.0 wt % to about 27.0 wt %, from about 8.0 wt % to about 26.0 wt %, from about 9.0 wt % to about 25.0 wt %, from about 10.0 wt % to about 24.0 wt %, from about 11.0 wt % to about 23.0 wt %, from about 12.0 wt % to about 22.0 wt %, from about 13.0 wt % to about 21.0 wt %, from about 14.0 wt % to about 20.0 wt %, from about 15.0 wt % to about 19.0 wt %, from about 16.0 wt % to about 18.0 wt %, or about 17.0 wt % of the bioactive copolymer.

In various embodiments, the base polymer is a synthetic polymer. In various embodiments, the base polymer is a thermoplastic polymer. The base polymer may be a medical grade polymer. The base polymer may be selected from the group consisting of polypropylene (PP), polyesters, poly (lactic acid) (PLA), poly(lactic-co-glycolic acid) (PLGA), poly(caprolactone) (PCL), polystyrene (PS), polyacrylates, poly(meth)acrylates, polyamides (PA), polyurethane (PU) and combinations thereof.

Bioactive Copolymer

In various embodiments, the bioactive copolymer is a bioactive synthetic copolymer with a poly(norbornene) backbone comprising/consisting essentially of/consisting of one or more repeating units represented by general formula (I) and one or more repeating units represented by general formula (II):

(I)

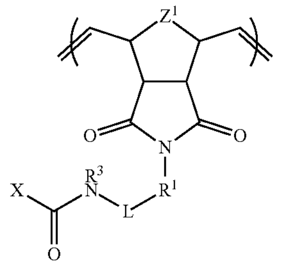

-continued (II)

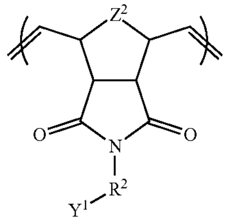

wherein $R^1$ is optionally substituted alkyl;

$R^2$ is selected from a single bond, optionally substituted alkyl, optionally substituted alkenyl, optionally substituted alkynyl, optionally substituted alkoxyalkyl, optionally substituted alkylcarbonyl or optionally substituted alkylcarbonylalkyl;

$R^3$ is selected from H, optionally substituted alkyl, optionally substituted alkenyl or optionally substituted alkynyl;

L is heteroalkylene;

X comprises a bioactive moiety selected from the group consisting of proteins, peptides, oligopeptides, carbohydrates, oligosaccharides, sugar, collagen, hyaluronic acid, therapeutic/drug molecules and derivatives thereof;

$Y^1$ comprises a synthetic polymer or parts thereof; and $Z^1$ and $Z^2$ are each independently selected from $CR^aR^b$, O, $NR^c$, $SiR^aR^b$, $PR^a$ or S, wherein $R^a$, $R^b$ and $R^c$ are each independently selected from the group consisting of H, optionally substituted alkyl, optionally substituted alkenyl and optionally substituted alkynyl.

In various embodiments, the repeating unit(s) represented by general formula (I) and/or moiety X possess bioactivity, biocompatibility and/or biodegradability. In various embodiments, the repeating unit(s) represented by general formula (II) and/or moiety $Y^1$ possess good mechanical strength/hardness. In various embodiments, the repeating unit represented by general formula (II) and/or moiety $Y^1$ has a higher mechanical strength than the repeating unit represented by general formula (I) and/or moiety X.

Advantageously, the presence of repeating units represented by general formulae (I) and (II) in the bioactive synthetic copolymer imparts both bioactivity and mechanical strength to the copolymer, leading to a mechanically strong bioactive copolymer. In various embodiments, the copolymer may also be biocompatible and/or biodegradable. Accordingly, in various embodiments, the copolymer is capable of being classified as a biomaterial. Advantageously, due to the presence of synthetic and bioactive side chains, the bioactive synthetic copolymer may also have a higher thermal stability than conventional biomolecules such as peptides, proteins, carbohydrates or glycosaminoglycans. Even more advantageously, the thermal stability of the bioactive synthetic copolymer allows for embodiments of the copolymer to be suitable for processing at high temperatures or even harsh material processing such as melt extrusion >200 °C, making the copolymer ideal/attractive for use in applications such as biomedical devices. In various embodiments, the synthetic polymer is substantially or completely non-bioactive, or at least less bioactive than the bioactive moiety.

In various embodiments, L is a polymeric linker that links the bioactive moiety X to the poly(norbornene) backbone. Advantageously, L is designed to be adjustable and/or customizable based on the size of the bioactive moiety X and the size of the synthetic polymer present in $Y^1$. The molecular weight and/or length of the polymeric linker L may be customized to suit the molecular weight and/or length of the bioactive moiety X and synthetic polymer chosen for $Y^1$, depending on the application the copolymer is to be used for. For example, in skin scaffolds, shorter synthetic polymeric (e.g., PCL or PLA) side chains are preferred for fast degradation whereas in bone scaffolds, longer synthetic polymeric (e.g., PCL or PLA) side chains are selected for slower degradation in body. Without being bound by theory, it is believed that bone tissues are expected to grow slower than skin tissues, hence the bone scaffold needs to stay intact in the body for a longer period of time for bone tissues to regenerate and cannot degrade too quickly. For example, for applications in dressings, or particularly non-biodegradable non-woven fibers which require thermal stability and/or mechanical strength properties, low molecular weight is preferred for synthetic polymers due to their poor solubility in common solvents. In various embodiments, synthetic polymers having low molecular weight comprises synthetic polymers having molecular weight of no more than about 5,000, for example when the synthetic polymers are highly insoluble, e.g. polyamide (PA). In other embodiments, synthetic polymers having a molecular weight of no more than about 10,000 may be used/acceptable, for example, when the synthetic polymers are less insoluble.

In various embodiments, the molecular weight and/or length of the polymeric linker L is selected such that the overall molecular size of the repeating unit represented by general formula (I) is similar/comparable to the molecular size of the repeating unit represented by general formula (II). For example, if PCL having a molecular weight of 4,000 is selected as the choice of synthetic polymer for $Y^1$ and peptide having a molecular weight of from about 400 to about 500 is selected as the choice of bioactive moiety X, then L may be designed to comprise a molecular weight of about 3,400. It will be appreciated that in various embodiments, it is the length of L that gets adjusted to match the molecular weight of general formula (I) to molecular weight of general formula (II).

In various embodiments, the molecular weight of general formula (I) is comparable/substantially similar with/to the molecular weight of general formula (II). In various embodiments, the molecular weight of general formula (I) does not differ from the molecular weight of general formula (II) by more than 30% of the molecular weight of general formula (II) or vice versa. For example, the molecular weight of general formula (I) may be at most about 30% more or at most 30% less than the molecular weight of general formula (II) or vice versa. The molecular weight of general formula (I) may not differ from the molecular weight of general formula (II) by more than about 30%, more than about 25%, more than about 20%, more than about 15%, more about 10%, more than about 5%, more than about 4%, more than about 3%, more than about 2%, or more than about 1% of the molecular weight of general formula (II) or vice versa. In various embodiments, the molecular weight of general formula (I) does not differ from the molecular weight of general formula (II) by more than about 20% of the molecular weight of general formula (II) or vice versa. For example, the molecular weight of general formula (I) may be at most about 20% more or at most 20% less than the molecular weight of general formula (II) or vice versa. Advantageously, as the bioactive moiety bearing repeating unit has a molecular size/weight/length that is similar to that of the synthetic polymer bearing repeating unit, the length of the bioactive moiety X is extended, thereby allowing X to be “visible”, available for binding to cells or accessible to its targeted physiological site for desired bioactivity, i.e. not buried in a sea/matrix of synthetic polymers.

In various embodiments, the molecular weight of general formula (I) is about 15,000, about 14,000, about 13,000 or at least about 12,000. In various embodiments, the molecular weight of general formula (I) is from about 100 to about 15,000, from about 200 to about 14,000, from about 300 to about 13,000, from about 400 to about 12,000, from about 500 to about 11,000, from about 1,000 to about 10,000, from about 1,500 to about 9,500, from about 2,000 to about 9,000, from about 2,500 to about 8,500, from about 3,000 to about 8,000, from about 3,500 to about 7,500, from about 4,000 to about 7,000, from about 4,500 to about 6,500, from about 5,000 to about 6,000 or about 5,500. In various embodiments, when X comprises longer peptides that contain more than 10 amino acids and the molecular weight of L is about 6,000, then the molecular weight of general formula (I) is greater than about 7,000.

In various embodiments, the molecular weight of general formula (II) is from about 100 to about 15,000, from about 200 to about 14,000, from about 300 to about 13,000, from about 400 to about 12,000, from about 500 to about 11,000, from about 1,000 to about 10,000, from about 1,500 to about 9,500, from about 2,000 to about 9,000, from about 2,500 to about 8,500, from about 3,000 to about 8,000, from about 3,500 to about 7,500, from about 4,000 to about 7,000, from about 4,500 to about 6,500, from about 5,000 to about 6,000 or about 5,500.

In various embodiments, the total molecular weight of general formula (I) and general formula (II) is kept to about 300,000, no more than about 300,000, no more than about 200,000, no more than about 100,000, no more than about 90,000, no more than about 80,000, no more than about 70,000, no more than about 60,000, no more than about 50,000, no more than about 45,000, no more than about 40,000, no more than about 35,000, no more than about 30,000, no more than about 25,000, no more than about 20,000, or no more than about 15,000 to facilitate copolymerisation.

In various embodiments, L is hydrophilic. As L is adjustable, the hydrophilicity of the repeating unit represented by general formula (I) and also the overall hydrophilicity of the bioactive synthetic copolymer may be adjusted as desired. Advantageously, the presence of L increases the hydrophilicity of the repeating unit represented by general formula (I) and also the overall hydrophilicity of the bioactive synthetic copolymer. Even more advantageously, the presence of L increases the hydrophilicity of the bioactive synthetic copolymer, therefore softening the synthetic polymeric chains which are hydrophobic, making the copolymer less stiff after processing. It will be appreciated by a person skilled in the art that, bioactive moieties and synthetic polymers are typically mutually incompatible as the individual bioactive moiety is generally hydrophilic while synthetic polymer is generally hydrophobic. Advantageously, L in repeating unit represented by general formula (I) is also used to extend the chain length of the bioactive moiety X attached at the end of L.

In various embodiments, L is amorphous. Advantageously, the presence of L increases the amorphousness and/or decreases the crystallinity of the bioactive synthetic copolymer, making the copolymer useful for crafting softer or less stiff plastics such as polystyrene-based material.

In various embodiments, L is a heteroalkylene having at least 20 carbon atoms, at least 30 carbon atoms, at least 40 carbon atoms, at least 50 carbon atoms, at least 60 carbon atoms, at least 70 carbon atoms, at least 80 carbon atoms, at least 90 carbon atoms, at least 100 carbon atoms, at least 150 carbon atoms, at least 200 carbon atoms, at least 250 carbon atoms or at least 300 carbon atoms. In various embodiments, L is $C_{20}$-$C_{300}$ heteroalkylene or a heteroalkylene having from 20 carbon atoms to 300 carbon atoms.

In various embodiments, L has a number average molecular weight of between about 500 and about 7,000. L may have a number average molecular weight of about 600, about 700, about 800, about 900, about 1,000, about 1,500, about 2,000, about 2,500, about 3,000, about 3,500, about 4,000, about 4,500, about 5,000, about 5,500, about 6,000, about 6,500 or about 7,000. In various embodiments, when X comprises a small bioactive moiety, the molecular weight of L may be adjusted to about 7,000 so that the total molecular weight of general formula (I) and general formula (II) is kept to no more than about 10,000. In various embodiments, the number average molecular weight of L is from about 1,000 to about 6,000.

In various embodiments, the heteroatom in L is O. In various embodiments, L is polyalkylene glycol. In various embodiments, L is poly($C_2$-$C_4$ alkylene glycol). L may be selected from the group consisting of polyethylene glycol (PEG), polypropylene glycol (PPG), polytetramethylene glycol (PTMG), polybutylene glycol (PBG) and the like. Advantageously, the use of a polyalkylene glycol such as PEG can increase hydrophilicity of the macromonomer and the resultant copolymer. In various embodiments, the polyalkylene glycol such as PEG are used as spacers, linkers or linking groups in the overall polymers, instead of as terminal groups.

In various embodiments, L is polyalkylene glycol having at least about 10 repeating units, at least about 15 repeating units, at least about 20 repeating units, at least about 21 repeating units, at least about 22 repeating units, at least about 23 repeating units, at least about 24 repeating units, at least about 25 repeating units, at least about 30 repeating units, at least about 40 repeating units, at least about 50 repeating units, at least about 60 repeating units, at least about 70 repeating units, at least about 80 repeating units, at least about 90 repeating units, at least about 100 repeating units, at least about 150 repeating units, at least about 200 repeating units, or at least about 250 repeating units. In various embodiments, L comprises from about 10 monomers/repeating units to about 250 monomers/repeating units. Unlike conventional polymers which uses a short PEG chain, embodiments of the bioactive synthetic copolymer disclosed herein incorporate a long polyalkylene glycol chain of at least 21 repeating units at L.

In various embodiments, L is selected from the group consisting of $PEG_{500}$, $PEG_{600}$, $PEG_{700}$, $PEG_{800}$, $PEG_{500}$, $PEG_{1000}$, $PEG_{1100}$, $PEG_{1200}$, $PEG_{1300}$, $PEG_{1400}$, $PEG_{1500}$, $PEG_{2000}$, $PEG_{2500}$, $PEG_{3000}$, $PEG_{3500}$, $PEG_{4000}$, $PEG_{4500}$, $PEG_{5000}$, $PEG_{5500}$, $PEG_{6000}$, $PEG_{6600}$ and mixtures thereof.

In various embodiments, X is coupled to the poly(norbornene dicarboximide) backbone through a carboxylic acid functionality in the following arrangement: —$R^1$-L-$NR^3$—C(=O)—X. Advantageously, by linking X through a carboxylic acid functionality, amine terminal group(s) in X is/are free up for delivering its bioactivity, therefore ensuring the bioavailability of X. It will be appreciated that as amine group(s) confer bioactivity, exhausting up amine groups in bioactive moieties for polymer binding may be undesirable.

In various embodiments, X is coupled to the poly(norbornene dicarboximide) backbone via peptide/amide linkage, i.e. —$NR^3$—C(═O)—. Advantageously, the bioactive synthetic copolymer disclosed herein is considerably stronger and/or stable than conventional polymers that contain ester linkages. Without being bound by theory, it is believed that amide linkages are stronger than ester linkages because ester linkages are more prone to hydrolysis, which may release bioactive moieties into the bloodstream, leading to a premature metabolism of bioactive moieties.

In various embodiments, one or more of H atoms in alkyl, alkenyl, alkynyl, alkoxyalkyl, alkylcarbonyl and alkylcarbonylalkyl is/are optionally replaced by hydroxy, hydroxyalkyl, halogen, haloalkyl, cyano, cyanoalkyl and nitro.

In various embodiments, $R^1$ is selected from $C_1$-$C_{20}$ alkyl. The $C_1$-$C_{20}$ alkyl substituents may be straight or branched substituents selected from methyl, ethyl, n-propyl, 2-propyl, isopropyl, n-butyl, isobutyl, sec-butyl, t-butyl, hexyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trim ethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl or the like. $R^1$ may be straight or branched $C_1$-$C_4$ alkyl substituents. In various embodiments, the length of $R^1$ is the same as the length of a repeating unit in L. For example, if L is poly(butylene glycol), then $R^1$ is butyl. In another example, if L is poly(ethylene glycol), then $R^1$ is ethyl. It will be appreciated that in various embodiments, $R^1$ is carefully designed to match L.

In various embodiments, $R^3$ is selected from H, $C_1$-$C_{20}$ alkyl, $C_2$-$C_{20}$ alkenyl or $C_2$-$C_{20}$ alkynyl.

In various embodiments, $Z^1$ and $Z^2$ are each independently selected from CH, O, NH, $SiR^aR^b$, $PR^a$ or S, wherein $R^a$, $R^b$, and $R^c$ are each independently selected from the group consisting of H, optionally substituted alkyl, optionally substituted alkenyl and optionally substituted alkynyl. The poly(norbornene) backbone may be selected from the group consisting of poly(norbornene-imide), poly(norbornene-dicarboximide), poly(norbornene) backbone is poly (5-norbornene-2,3-dicarboximide), poly(7-oxanorbornene), poly(oxanorbornene-imide), poly(oxanorbornene-dicarboximide) and the like. In various embodiments, $Z^1$ and $Z^2$ are each independently selected from $CR^aR^b$, O, $NR^c$, $SiR^aR^b$, $PR^a$ or S, wherein $R^a$, $R^b$, and $R^c$ are each independently selected from the group consisting of H, $C_1$-$C_{20}$ alkyl, $C_1$-$C_{20}$ alkenyl and $C_1$-$C_{20}$ alkynyl. In various embodiments, $Z^1$ is $CH_2$. In various embodiments, $Z^2$ is $CH_2$.

In various embodiments, X comprises a bioactive moiety selected from proteins, peptides, carbohydrates, therapeutic/drug molecules and derivatives thereof. In various embodiments, proteins, peptides, carbohydrates or therapeutic/drug molecules derivatives thereof include proteins, peptides, carbohydrates or therapeutic/drug molecules that are or have been optionally modified to contain one carboxylic acid terminal group. In some embodiments, the bioactive moiety contains only one carboxylic acid terminal group.

In some embodiments, the bioactive moiety comprises a monocarboxylic acid. Advantageously, in some embodiments, the use of a bioactive moiety having a monocarboxylic acid terminal group may reduce/avoid the possibility of an undesirable crosslinking as compared to the case of using more than one carboxylic acid. In some embodiments therefore, the bioactive moiety X is substantially devoid of more than one carboxylic acid terminal group, for e.g., a dicarboxylic acid or tricarboxylic acid.

In various embodiments, X comprises protein or peptide. X may be a peptide sequence, laminin-derived peptide, integrin binding peptide, cell-penetrating peptide, collagen mimics or collagen fragments. In various embodiments, X comprises from 2 to 50 amino acid residues, from 2 to 40 amino acid residues or from 2 to 20 amino acid residues in any sequence. In various embodiments, X comprises 50 amino acid residues, 40 amino acid residues, 30 amino acid residues, 25 amino acid residues, 20 amino acid residues, 15 amino acid residues, 10 amino acid residues, 9 amino acid residues, 8 amino acid residues, 7 amino acid residues, 6 amino acid residues, 5 amino acid residues, 4 amino acid residues or 3 amino acid residues in any sequence. The amino acid residues may be selected from the group consisting of glycine, alanine, valine, leucine, isoleucine, methionine, proline, phenylalanine, tryptophan, asparagine, glutamine, glycine, serine, threonine, serine, asparagine, glutamine, tyrosine, cysteine, lysine, arginine, histidine, aspartic acid and glutamic acid. In various embodiments, X is a peptide sequence comprising 3 to 20 natural amino acids. X may be integrin binding peptide selected from the group consisting of arginine-glycine-aspartic acid (RGD), SRGDS and RGDS; laminin-derived peptide A5G81 (AGQWHRVSVRWGC); osteopontin derived peptides SVVYGLR; and cell-penetrating/antimicrobial peptide selected from $(IRIK)_2$ or $(IKKI)_3$. In various embodiments, X is a collagen sequence comprising 3 to 20 units of glycine (G), proline (P) and hydroxyproline (Hyp) in any sequence or permutation. X may be collagen fragment having a $(PHypG)_n$ type sequence, $(PGHyp)_n$ type sequence, $(HypGP)_n$ type sequence, $(HypPG)_n$ type sequence, $(GHypP)_n$ type sequence, $(GPHyp)_n$ type sequence or collagen mimic DGEA.

In various embodiments, X comprises carbohydrate or sugar. In various embodiments, X comprises monosaccharide, disaccharide, oligosaccharide or polysaccharide. In various embodiments, X comprises from 2 to 50 saccharide units, from 2 to 40 saccharide units, from 2 to 20 saccharide units or from 10 to 14 saccharide units. In various embodiments, X comprises 50 saccharide units, 40 saccharide units, 30 saccharide units, 25 saccharide units, 20 saccharide units, 15 saccharide units, 14 saccharide units, 13 saccharide units, 12 saccharide units, 11 saccharide units, 10 saccharide units, 9 saccharide units, 8 saccharide units, 7 saccharide units, 6 saccharide units, 5 saccharide units, 4 saccharide units or 3 saccharide units or 2 saccharide units. X may be heparin sulfate (HS) or glycosaminoglycans (GAGs). In various embodiments, X is heparin sulfate/oligosaccharide selected from the group consisting of DP8, DP10, DP12, DP14 and DP16. In various embodiments, X is hyaluronic acid which is the simplest form of glycosaminoglycan (GAG).

In various embodiments, X is chemically coupled to the rest of general formula (I) via its hydroxy group. For example, when X is carbohydrate/saccharide, oxidation and/or reductive amination reactions may be performed on the carbohydrate's hydroxy for linking X to general formula (I). —$CH_2OH$ on the saccharide may be oxidised to —C(═O)H, which subsequently undergoes reductive amination using the —$NH_2$ terminal on L to create a peptide linkage.

In various embodiments, X comprises a carbohydrate/saccharide that contained or has been modified to contain one carboxylic acid terminal group. Modification by one or more chemical reaction(s) such as oxidation may be performed on the carbohydrate/saccharide to create a carboxylic acid group. In various embodiments, modification is performed on a hydroxyl group that is originally present in the carbohydrate/saccharide. In various embodiments, —$CH_2OH$ on the carbohydrate/saccharide is oxidized completely to —C(═O)OH, which subsequently reacts with a —$NH_2$ terminal on L to create a peptide linkage that links the carbohydrate/saccharide to the rest of general formula (I): X—C(═O)—NH-L-. It will be appreciated, however, that no modification to the carbohydrate/saccharide may be required/necessary if a carboxylic acid is naturally present in the carbohydrate/saccharide.

In various embodiments, X comprises therapeutic/drug molecule. In various embodiments, X comprises antibiotic, antimicrobial, antibacterial, blood thinning agents or anti-inflammatory agents. X may be penicillin, amoxicillin, amphotericin, ciprofloxacin (CIF), atorvastatin, aspirin or aminoglycoside-based molecules selected from streptomycin, ribostamycin or gentamycin. It will be appreciated that X may be any therapeutic or drug molecule that contains a carboxylic acid group.

In various embodiments, X is chemically coupled to the rest of general formula (I) via one of its chemical moiety selected from the group consisting of —COOH, —$CH_2OH$, —$CH_2NH_2$ and ═$CHNH_2$. For example, —$CH_2NH_2$ or ═$CHNH_2$ on the drug molecule may be coupled to a small dicarboxylic acid before reacting with a —$NH_2$ terminal on L to create a peptide linkage that links the drug molecule to the rest of general formula (I): X—C(═O)—NH-L-.

In various embodiments, X comprises a therapeutic/drug molecule that contained or has been modified to contain one carboxylic acid terminal group. Modification by one or more chemical reaction(s) such as oxidation may be performed on the therapeutic/drug molecule to create a carboxylic acid group. In various embodiments, modification is performed on a hydroxyl group that is originally present in the therapeutic/drug molecule. For example, in various embodiments when X is ribostamycin or gentamycin, —$CH_2OH$ on the drug molecule is oxidized completely to —C(═O)OH, which subsequently reacts with a —$NH_2$ terminal on L to create a peptide linkage that links the drug molecule to the rest of general formula (I): X—C(═O)—NH-L-. It will be appreciated, however, that no modification to the therapeutic/drug molecule may be required/necessary if a carboxylic acid is already present in the therapeutic/drug molecule.

In various embodiments, the bioactive moiety is or has been modified to contain one carboxylic acid terminal group. For example, if a carboxylic acid terminal group is absent in a carbohydrate or therapeutic/drug molecule, the carbohydrate or therapeutic/drug molecule may be modified to add a carboxylic acid at one of the carbohydrate or therapeutic/drug molecule terminals. The modification may comprise oxidation reaction(s) to convert a hydroxy group in the carbohydrate to carboxylic acid.

In various embodiments, the repeating unit represented by general formula (I) is in an amount of from about 1 molar % to about 100 molar %, from about 2 molar % to about 99 molar %, from about 3 molar % to about 98 molar %, from about 4 molar % to about 97 molar %, from about 5 molar % to about 96 molar %, from about 10 molar % to about 95 molar %, from about 15 molar % to about 90 molar %, from about 20 molar % to about 85 molar %, from about 25 molar % to about 80 molar %, from about 30 molar % to about 75 molar %, from about 35 molar % to about 70 molar %, from about 40 molar % to about 65 molar %, from about 45 molar % to about 60 molar %, or from about 50 molar % to about 55 molar % relative to the copolymer. In various embodiments, the repeating unit represented by general formula (I) is in an amount of from about 1 molar % to about 10 molar % relative to the copolymer. In various embodiments, the bioactive moiety is about 2 molar %, about 3 molar %, about 4 molar %, about 5 molar %, about 6 molar %, about 7 molar %, about 8 molar %, about 9 molar % or about 10 molar % of the bioactive synthetic copolymer.

In various embodiments, $R^2$ is selected from $C_1$-$C_{20}$ alkyl, $C_2$-$C_{20}$ alkenyl, $C_2$-$C_{20}$ alkynyl, $C_1$-$C_{20}$ alkoxyalkyl, $C_2$-$C_{20}$ alkylcarbonyl or $C_3$-$C_{20}$ alkylcarbonylalkyl. The $C_1$-$C_{20}$ alkyl substituents may be straight or branched substituents selected from methyl, ethyl, n-propyl, 2-propyl, isopropyl, n-butyl, isobutyl, sec-butyl, t-butyl, hexyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trim ethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl or the like.

In various embodiments, $Y^1$ is represented by general formula (III):

(III)

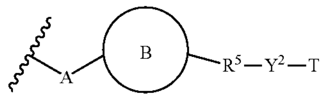

wherein

A is selected from a single bond, oxy, carbonyl, oxycarbonyl, carboxyl, optionally substituted alkoxy, optionally substituted alkoxyalkyl, optionally substituted alkylcarbonyl, optionally substituted alkylcarbonylalkyl, optionally substituted carboxyalkyl, optionally substituted oxycarbonylalkyl, optionally substituted alkylcarboxylalkyl, optionally substituted alkoxycarbonylalkyl, N or $NR^c$ wherein $R^c$ is independently selected from H, optionally substituted alkyl, optionally substituted alkenyl or optionally substituted alkynyl;

B is optionally present as a ring selected from 1,2,3-triazole or succinimide;

$R^5$ is selected from a single bond, optionally substituted alkyl, optionally substituted alkenyl, optionally substituted alkynyl, optionally substituted alkoxyalkyl, optionally substituted alkylcarbonyl or optionally substituted alkylcarbonylalkyl;

$Y^2$ is selected from the group consisting of polypropylene (PP), polyesters, poly(lactic acid) (PLA), poly(lactic-co-glycolic acid) (PLGA), poly(caprolactone) (PCL), polystyrene (PS), polyacrylates, poly(meth)acrylates, polyamides (PA), polyurethane (PU) and parts thereof; and T is a terminal group selected from the group consisting of hydrogen, halogen, hydroxyl, amino, acyl, thiol, optionally substituted alkyl, optionally substituted alkenyl, optionally substituted alkynyl, optionally substituted alkoxy, optionally substituted alkoxyalkyl, optionally substituted alkylcarbonyl, optionally substituted alkylcarbonylalkyl, optionally substituted carboxyalkyl, optionally substituted oxycarbonylalkyl, optionally substituted alkylcarboxylalkyl or optionally substituted alkoxycarbonylalkyl.

In various embodiments, $Y^2$ is a polyacrylate comprising one or more monomers selected from the group consisting of methyl acrylate, ethyl acrylate, n-propyl acrylate, isopropyl acrylate, n-butyl acrylate, isobutyl acrylate, tert-butyl acrylate, hexyl acrylate, cyclohexyl acrylate, 2-ethylhexyl acrylate, benzyl acrylate and phenyl acrylate. $Y^2$ may be poly (methyl acrylate), poly(ethyl acrylate), poly(butyl acrylate) or poly (2-ethylhexyl acrylate). In various embodiments, $Y^2$ is a poly(meth)acrylate comprising one or more monomers selected from the group consisting of methyl methacrylate, ethyl methacrylate, n-propyl methacrylate, isopropyl methacrylate, n-butyl methacrylate, isobutyl methacrylate, tert-butyl methacrylate, hexyl methacrylate, cyclohexyl methacrylate, 2-ethylhexyl methacrylate, benzyl methacrylate and phenyl methacrylate. $Y^2$ may be poly(methyl methacrylate) (PMMA), poly(ethyl methacrylate) and poly(butyl methacrylate) or poly (2-ethylhexyl acrylate).

In various embodiments, $Y^2$ is a polyurethane. In such embodiments, the one or more repeating units represented by general formula (II) has the following structure:

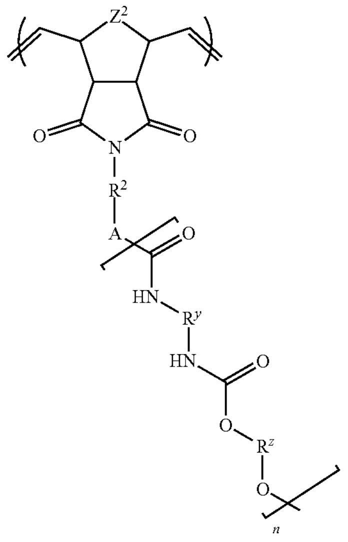

wherein $R^2$ is alkyl;

A is 0 or $NR^c$ wherein $R^c$ is independently selected from H, optionally substituted alkyl, optionally substituted alkenyl or optionally substituted alkynyl;

$R^y$ is selected from an alkyl, aryl or biaryl; and $R^z$ is alkyl.

In various embodiments, A is selected from a single bond, oxy, carbonyl oxycarbonylalkyl, N or $NR^c$ wherein $R^c$ is independently selected from H, optionally substituted alkyl, optionally substituted alkenyl or optionally substituted alkynyl. A may be a single bond, O, C(=O) and O—C(=O)—R, wherein R is optionally substituted alkyl, optionally substituted alkenyl or optionally substituted alkynyl. In various embodiments, R is straight or branched alkyl substituents selected from methyl, ethyl, n-propyl, 2-propyl, isopropyl, n-butyl, isobutyl, sec-butyl, t-butyl, hexyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl or the like. In various embodiments, A is selected from a single bond, O, C(=O) or O—C(=O)—$C_1$-$C_6$ alkyl.

In various embodiments, B is absent. In various embodiments, B is present as a ring selected from 1,2,3-triazole or succinimide. Advantageously, 1,2,3-triazole is suitable for connectivity with the present system because of the chemistry used. For example, azide-alkyne click chemistry forms 1,2,3-triazole, which links the norbornene dicarboximide to synthetic polymer $Y^2$. Advantageously, succinimide is suitable for connectivity with the present system because of the chemistry used.

In various embodiments, $R^5$ is selected from a single bond, optionally substituted alkyl, optionally substituted alkenyl or optionally substituted alkynyl. $R^5$ may be a single bond or straight or branched alkenyl substituents selected from ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 2-octenyl, 3-octenyl, 1-nonenyl, 2-nonenyl, 3-nonenyl, 1-decenyl, 2-decenyl, 3-decenyl or the like. In various embodiments, $R^5$ is selected from a single bond or $C_2$-$C_6$ alkenyl.

In various embodiments, $Y^2$ comprises one or more of the following properties: bioresorbable; inert; long shelf life; mechanical strength; impact resistant; thermal stability; elasticity; elastic recovery; smoothness; biodegradable; lightweight; and low or non-toxicity.

In various embodiments, $Y^2$ is substantially devoid of polyalkylene glycol such as polyethylene glycol.

In various embodiments, T is a terminal group selected from the group consisting of hydrogen, halogen, hydroxyl, optionally substituted alkyl, optionally substituted alkenyl, optionally substituted alkynyl, optionally substituted alkylcarboxylalkyl and optionally substituted alkoxycarbonylalkyl. T may be H, OH, halogen selected from $C_1$, F, Br, I, $C_1$-$C_6$ alkyl, $C_1$-$C_6$ alkyl-C(=O)—O—$C_1$-$C_6$ alkyl or $C_1$-$C_6$ alkyl-O— C(=O)—$C_1$-$C_6$ alkyl.

In various embodiments, $Y^1$ is selected from the following general formulae (IIIa), (IIIb), (IIIc), (IIId), (IIIe), (IIIf), or (IIIg):

(IIIa)

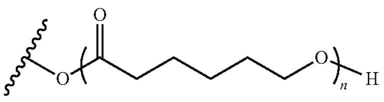

(IIIb)

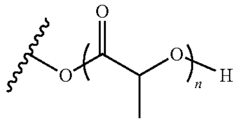

(IIIc)

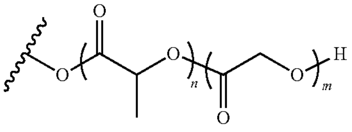

-continued (IIId)

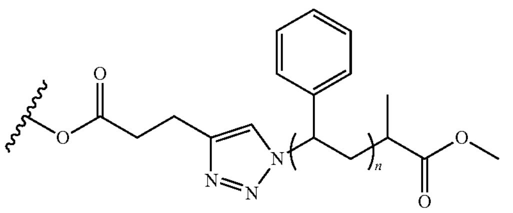

(IIIe)

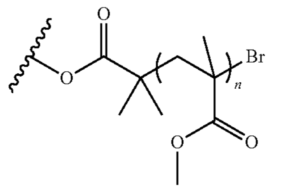

(IIIf)

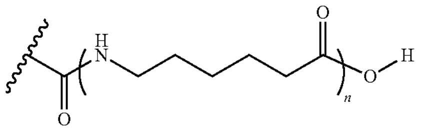

(IIIg)

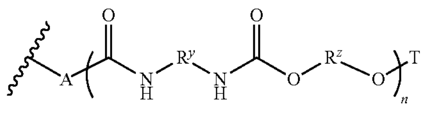

wherein $R^y$ is selected from an alkyl, aryl or biaryl;

$R^z$ is alkyl;

A is 0 or $NR^c$ wherein $R^c$ is independently selected from H, optionally substituted alkyl, optionally substituted alkenyl or optionally substituted alkynyl;

T is a terminal group selected from the group consisting of hydrogen and methyl;

n≥1; and m≥1.

In various embodiments, the total molecular weight of general formula (II) is kept to no more than about 15,000 or no more than about 10,000. It will be appreciated that copolymerisation may become inefficient when the total molecular weight of general formula (I) and (II) is too high. In various embodiments, when the bioactive synthetic copolymer is used for applications which require fast biodegradation, the molecular weight of general formula (II) is kept low by adjusting the value of n and/or m.

In various embodiments, the ratio of the number of repeating units represented by general formula (I) to the number of repeating units represented by general formula (II) in the bioactive synthetic copolymer is from about 1:1 to about 1:100, from about 1:2 to about 1:99, from about 1:3 to about 1:98, from about 1:4 to about 1:97, from about 1:5 to about 1:96, from about 1:6 to about 1:95, from about 1:7 to about 1:90, from about 1:8 to about 1:85, from about 1:9 to about 1:80, from about 1:10 to about 1:75, from about 1:15 to about 1:70, from about 1:20 to about 1:65, from about 1:25 to about 1:60, from about 1:30 to about 1:55, from about 1:35 to about 1:50, or from about 1:40 to about 1:45. In various embodiments, the ratio of the number of repeating units represented by general formula (I) to the number of repeating units represented by general formula (II) in the bioactive synthetic copolymer is about 1:10, about 1:15, about 1:20, about 1:25, about 1:30, about 1:35, about 1:40, about 1:45 or about 1:50.

In various embodiments, the number of repeating units represented by general formula (I) in the copolymer is from about 10 to about 1,000. In various embodiments, the number of repeating units represented by general formula (II) in the copolymer is from about 10 to about 1,000. In various embodiments, for bone scaffold construction, PLA side chains comprise from about 50 to about 60 lactide units.

In various embodiments, the bioactive synthetic copolymer has a number average molecular weight ($M_n$) of from about 1,000 to about 300,000, 2,000 to about 250,000, from about 3,000 to about 200,000, from about 4,000 to about 150,000, from about 5,000 to about 100,000, from about 10,000 to about 90,000, from about 20,000 to about 80,000, from about 30,000 to about 70,000, from about 40,000 to about 60,000, or about 50,000.

In various embodiments, the bioactive synthetic copolymer has a polydispersity index (PDI) of from about 1.0 to about 10.0. In various embodiments, PDI of the bioactive synthetic copolymer is about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5 or about 10.0. In various embodiments, the bioactive synthetic copolymer has a polydispersity index (PDI) of from about 1.0 to about 3.0, from about 1.05 to about 2.95, from about 1.1 to about 2.9, from about 1.2 to about 2.8, from about 1.4 to about 2.6, from about 1.6 to about 2.4, from about 1.8 to about 2.2 or about 2.0. In various embodiments, the PDI of the bioactive synthetic copolymer is no more than 1.50.

In various embodiments, the one or more repeating units represented by general formula (I) and the one or more repeating units represented by general formula (II) are designed to link to the poly(norbornene) backbone via at least covalent interactions. In various embodiments, each repeating unit represented by general formula (I) is covalently bonded to the poly(norbornene) backbone and/or each repeating unit represented by general formula (II) is covalently bonded to the poly(norbornene) backbone. Advantageously, as bioactive moieties (in general formula (I)) are covalently bonded to the bioactive synthetic polymer, bioactivity is localized. In various embodiments, the bioactive moieties such as biomolecules do not leach out from the polymer, therefore preventing undesirable/unwanted side effects caused by biomolecules entering the circulatory system and/or reaching unintended parts of the body system. Embodiments of the bioactive synthetic copolymer therefore overcome problems faced by conventional biomolecules that are administered as drugs which may metabolized prematurely before therapeutic effects are achieved. In various embodiments, the bioactive moieties such as drug molecules do not leach out into media which can escape into the environment in the event that disposal is improperly managed.

It will be appreciated that other interactions such as Van der Waals interactions may also be present within the copolymer.

In various embodiments, the bioactive synthetic copolymer comprises a brush, bottlebrush, block, comb or graft-copolymer structure. In various embodiments, the repeating units may be randomly distributed/arranged within the polymer.

In various embodiments, the one or more repeating units represented by general formula (I) comprises two or more different types of bioactive moiety X. In various embodiments, the one or more repeating units represented by general formula (I) comprises 2, 3, 4, 5, 6, 7 or 8 different types of bioactive moiety X. For example, within a bioactive synthetic copolymer, there may be repeating units represented by general formula (I) comprising peptide as X and repeating units represented by general formula (I) comprising carbohydrate as X. Advantageously, in various embodiments, the bioactive synthetic copolymer imparts two or more different types of bioactivities.

In various embodiments, the one or more repeating units represented by general formula (II) comprises two or more different types of synthetic polymer $Y^2$. In various embodiments, the one or more repeating units represented by general formula (II) comprises 2, 3, 4, 5, 6, 7 or 8 different types of synthetic polymer $Y^2$.

In various embodiments, the bioactive synthetic copolymer is a random polymer or a block copolymer. In some embodiments, the block polymer is a di-block or a triblock polymer. For example, the copolymer may have or is made up of two or three different polymer blocks. In some embodiments, the multi-block copolymer comprises more than three polymeric blocks. The blocks may be randomly distributed/arranged within the polymer.

Advantageously, the bioactive synthetic copolymer disclosed herein is highly customizable. Depending on the application that the bioactive synthetic copolymer is intended, X with the desired biological activity and $Y^2$ with the desired physical attributes may be selected to eventually obtain the bioactive synthetic copolymer with the desired repeating units represented by general formulae (I) and (II).

In various embodiments, the bioactive synthetic copolymer is blended with a base polymer for further use. In various embodiments, the base polymer is similar to or of the same type as the synthetic polymer $Y^2$ used in general formula (II). In various embodiments, a medical grade polymer is used for base material while low molecular weight synthetic polymer is used in the synthetic side chain of the bioactive synthetic copolymer. Advantageously, embodiments of the bioactive synthetic polymer allow for biomolecule to be blended into base material of synthetic polymer similar to the synthetic polymer side arms of copolymer, without phase separation.

In various embodiments, the bioactive copolymer is a medical grade polymer. In various embodiments, the bioactive copolymer is also a thermoplastic polymer.

It will be appreciated that other bioactive copolymers obtained by ROMP may also be suitable such as that disclosed in PCT application no. PCT/SG2020/050621, which is fully incorporated in its entirety by reference.

Fused Filament Fabrication (FFF) or Fused Deposition Modelling (FDM) Based Three-Dimensional Printing Method In various embodiments, there is also provided a bioactive polymer filament obtained from the filament production method disclosed herein. Advantageously, the bioactive polymer filament is a feedstock designed for use in fused filament fabrication (FFF) or fused deposition modelling (FDM) method of manufacturing which consists of thermally stable biological molecules that improves bioactivity with adequate mechanical properties. The bioactive polymer filament may comprise/consist essentially of/consist of the base polymer and bioactive copolymer disclosed herein. In various embodiments, the bioactive polymer filament is substantially free from or devoid of other additives such as lubricants.

In various embodiments, the bioactive polymer filament is substantially free from or devoid of other non-medically approved ingredients. In various embodiments, the bioactive polymer filament is a monofilament.

Accordingly, there is also provided a fused filament fabrication (FFF) or fused deposition modelling (FDM) based three-dimensional printing method using the bioactive polymer filament disclosed herein as a feedstock. In various embodiments, the method comprises feeding a bioactive polymer filament disclosed herein into a FFF or FDM based three-dimensional printing apparatus (e.g. fed to the print head of the apparatus); applying heat to bioactive polymer filament to obtain a molten/melted form of the bioactive polymer; and depositing the molten/melted bioactive polymer on a print bed to form a printed three-dimensional part or structure. Advantageously, FFF or FDM 3D printing/printers have great advantages such as low cost, shortened time to market and part customisation which are significantly beneficial for medical technology.

The method may further comprise performing one or more of post-printing analysis of the printed three-dimensional part or structure, the post-printing analysis selected from the group consisting of:

i. a mechanical analysis of the printed three-dimensional part or structure e.g. to assess its mechanical properties;
ii. a biocompatibility analysis of the printed three-dimensional part or structure e.g. to assess its biocompatibility with living cells;
iii. a thermal analysis on the printed three-dimensional part or structure e.g. to assess onset degradation of the bioactive polymer in the printed three-dimensional part or structure; and
iv. a spectrometric analysis of the printed three-dimensional part or structure to assess the presence of bioactive copolymer in the printed three-dimensional part or structure. For example, nuclear magnetic resonance (NMR) spectroscopy may be performed on the filament and/or the printed three-dimensional part or structure.

The mechanical analysis may be performed under ASTM standards or other equivalent standards to determine the properties of the printed structure and whether it is suitable for its specific use. It will be appreciated that any other test methods that are equivalent to the ASTM standards may be used as well. Furthermore, the biocompatibility tests may be carried out with various human cell lines which the materials are designed to interact with. The thermal analysis may comprise one or more of thermogravimetric analysis (TGA) and differential scanning calorimetry (DSC). In various embodiments, the thermal analysis comprises simultaneous thermal analysis (STA) through the simultaneous application of TGA and DSC.

In various embodiments, the step of applying heat is at a temperature that is based on a predetermined melt/softening temperature and a predetermined onset degradation temperature of the bioactive polymer. For example, the printing may be performed at a temperature (e.g. the temperature of the print head) that is no more than the temperature at which the biological/bioactive(s)/active pharmaceutical ingredient(s) part of the filament degrades/decomposes/disintegrates/depolymerises/breaks down. In various embodiments, the printing is performed at a temperature that is between the melt/softening temperature of bioactive polymer filament and the onset degradation temperature of the bioactive polymer. In various embodiments, the printing temperature is dependent on the bioactive polymer filament used for 3D printing. The printing may be performed at a temperature that is from about 15 °C to about 40 °C above the melting/softening point of the bioactive polymer filament and up to 5 °C below the degradation point of the bioactive polymer. In some embodiments, the printing is performed at a temperature that is from about 15 °C to about 40 °C, from about 16 °C to about 39 °C, from about 17 °C to about 38 °C, from about 18 °C to about 37 °C, from about 19 °C to about 36 °C, from about 20 °C to about 35 °C, from about 21 °C to about 34 °C, from about 22 °C to about 33 °C, from about 23 °C to about 32 °C, from about 24 °C to about 31 °C, from about 25 °C to about 30 °C, from about 26 °C to about 29 °C, or from about 27 °C to about 28 °C above the melting/softening point/temperature of the bioactive polymer filament. In some embodiments, the printing is performed at a temperature that is no more than about 5 °C, no more than about 4.5 °C, no more than about 4 °C, no more than about 3.5 °C, no more than about 3 °C, no more than about 2.5 °C, no more than about 2 °C, no more than about 1.5 °C, no more than about 1 °C, no more than about 0.5 °C, no more than about 0.4 °C, no more than about 0.3 °C, no more than about 0.2 °C, or no more than about 0.1 °C below the degradation point/temperature of the bioactive polymer.

The printing may be performed in the presence of a base plate that has a temperature that is no less than the temperature at which the thermoplastic solidifies or converts into solid state. In various embodiments, the base plate temperature is dependent on the bioactive polymer filament used for 3D printing. The temperature of the base plate may range from room temperature (e.g., no heating) and up to about 15 °C above the melting/softening temperature of the bioactive polymer filament. In some embodiments, the printing is performed in the presence of a base plate having a temperature ranging from about 20 °C to about 30 °C, from about 21 °C to about 29 °C, from about 22 °C to about 28 °C, from about 23 °C to about 27 °C, from about 24 °C to about 26 °C, or about 25 °C. In some embodiments, the printing is performed in the presence of a base plate having a temperature that is no more than about 15 °C, no more than about 14 °C, no more than about 13 °C, no more than about 12 °C, no more than about 11 °C, no more than about 10 °C, no more than about 9 °C, no more than about 8 °C, no more than about 7 °C, no more than about 6 °C, no more than about 5 °C, no more than about 4 °C, no more than about 3 °C, no more than about 2 °C, or no more than about 1 °C above the melting/softening point/temperature of the bioactive polymer filament.

In various embodiments, the printing is performed at a printing speed of from about 1.0 mm/s to about 70.0 mm/s, from about 2.0 mm/s to about 69.0 mm/s, from about 3.0 mm/s to about 68.0 mm/s, from about 4.0 mm/s to about 67.0 mm/s, from about 5.0 mm/s to about 66.0 mm/s, from about 6.0 mm/s to about 65.0 mm/s, from about 7.0 mm/s to about 64.0 mm/s, from about 8.0 mm/s to about 63.0 mm/s, from about 9.0 mm/s to about 62.0 mm/s, from about 10.0 mm/s to about 61.0 mm/s, from about 15.0 mm/s to about 60.0 mm/s, from about 20.0 mm/s to about 55.0 mm/s, from about 25.0 mm/s to about 50.0 mm/s, from about 30.0 mm/s to about 45.0 mm/s, or from about 35.0 mm/s to about 40.0 mm/s.

In various embodiments, the FFF or FDM based three-dimensional printing apparatus is configured for filament feedstock having filament diameters falling in the range of from about 1.5 mm to about 4.0 mm, from about 1.6 mm to about 3.9 mm, from about 1.7 mm to about 3.5 mm, from about 1.71 mm to about 3.4 mm, from about 1.72 mm to about 3.3 mm, from about 1.73 mm to about 3.2 mm, from about 1.74 mm to about 3.1 mm, from about 1.75 mm to about 3.0 mm, from about 1.76 mm to about 2.95 mm, from about 1.77 mm to about 2.90 mm, from about 1.78 mm to about 2.88 mm, from about 1.79 mm to about 2.86 mm, or from about 1.80 mm to about 2.85 mm.

Advantageously, in various embodiments, the printing method and bioactive polymer filament feedstock is capable of being used by commercially available FFF or FDM based three-dimensional printers or extruders.

In various embodiments, the bioactive polymer is printed with a printing nozzle having a diameter of from about 0.10 mm to about 1.00 mm, from about 0.11 mm to about 0.99 mm, from about 0.12 mm to about 0.98 mm, from about 0.13 mm to about 0.97 mm, from about 0.14 mm to about 0.96 mm, from about 0.15 mm to about 0.95 mm, from about 0.20 mm to about 0.90 mm, from about 0.25 mm to about 0.85 mm, from about 0.30 mm to about 0.80 mm, from about 0.35 mm to about 0.75 mm, from about 0.40 mm to about 0.70 mm, from about 0.45 mm to about 0.65 mm, from about 0.50 mm to about 0.60 mm, from about 0.51 mm to about 0.59 mm, from about 0.52 mm to about 0.58 mm, from about 0.53 mm to about 0.57 mm, from about 0.54 mm to about 0.56 mm, or about 0.55 mm.

In various embodiments, the FFF or FDM based three-dimensional printing is according to a design model to obtain a structure with the desired design. Accordingly, the method may further comprise, prior to the step of printing, digitally modelling/designing a 3D geometry/structure using a digital software.

In various embodiments, the printed 3D structure is not suitable for oral administration. In some embodiments, the printed 3D structure is biodegradable and/or biocompatible. In various embodiments, the printed 3D structure is structurally and mechanically capable of providing structural support and/or supporting cellular growth thereon.

BRIEF DESCRIPTION OF FIGURES

FIG. 20 and FIG. 21 show a comparison of bio-implanted murine skin tissues using PA-based materials in accordance with various embodiments disclosed herein.

GPHP). Bioactive nylon filament PA12-(PA6-GPHP) consists of PA12 as base polymer and PA6-GPHP as the bioactive copolymer. Image shown is representative with at least 4 C57BL/6 mice per group. Scale bar=50 μm.

FIG. 22 and FIG. 23 show a comparison of bio-implanted murine skin tissues using PCL-based materials in accordance with various embodiments disclosed herein.

Figure 22A:

FIG. 22A shows an image obtained from immunohistochemistry (IHC) staining for $CD3^+$ cells, with cell nuclei (dark coloured spots) and CD3 (representatively circled) differentially labelled. Skin tissues from negative control mice and bio-implanted mice elicited comparable level of immune response. Pathological assessment reports 1+ for negative control. Image shown is representative with at least 4 C57BL/6 mice per group. Scale bar=50 μm.

Figure 22B:
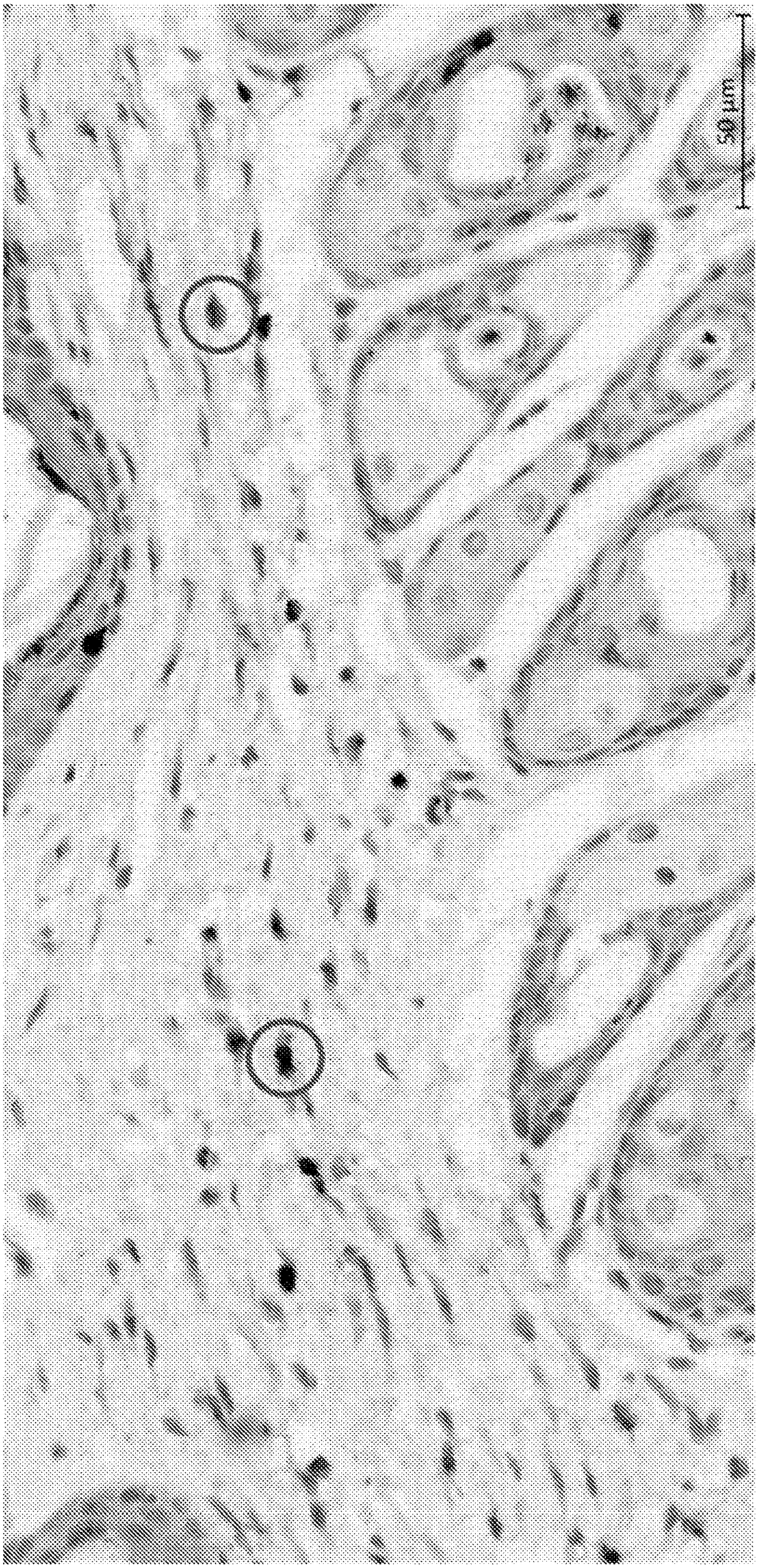

FIG. 22B shows an image obtained from immunohistochemistry (IHC) staining for $CD3^+$ cells, with cell nuclei (dark coloured spots) and CD3 (representatively circled) differentially labelled. Skin tissues from negative control mice and bio-implanted mice elicited comparable level of immune response. Pathological assessment reports 1+ for PCL. Image shown is representative with at least 4 C57BL/6 mice per group. Scale bar=50 μm.

Figure 22C:
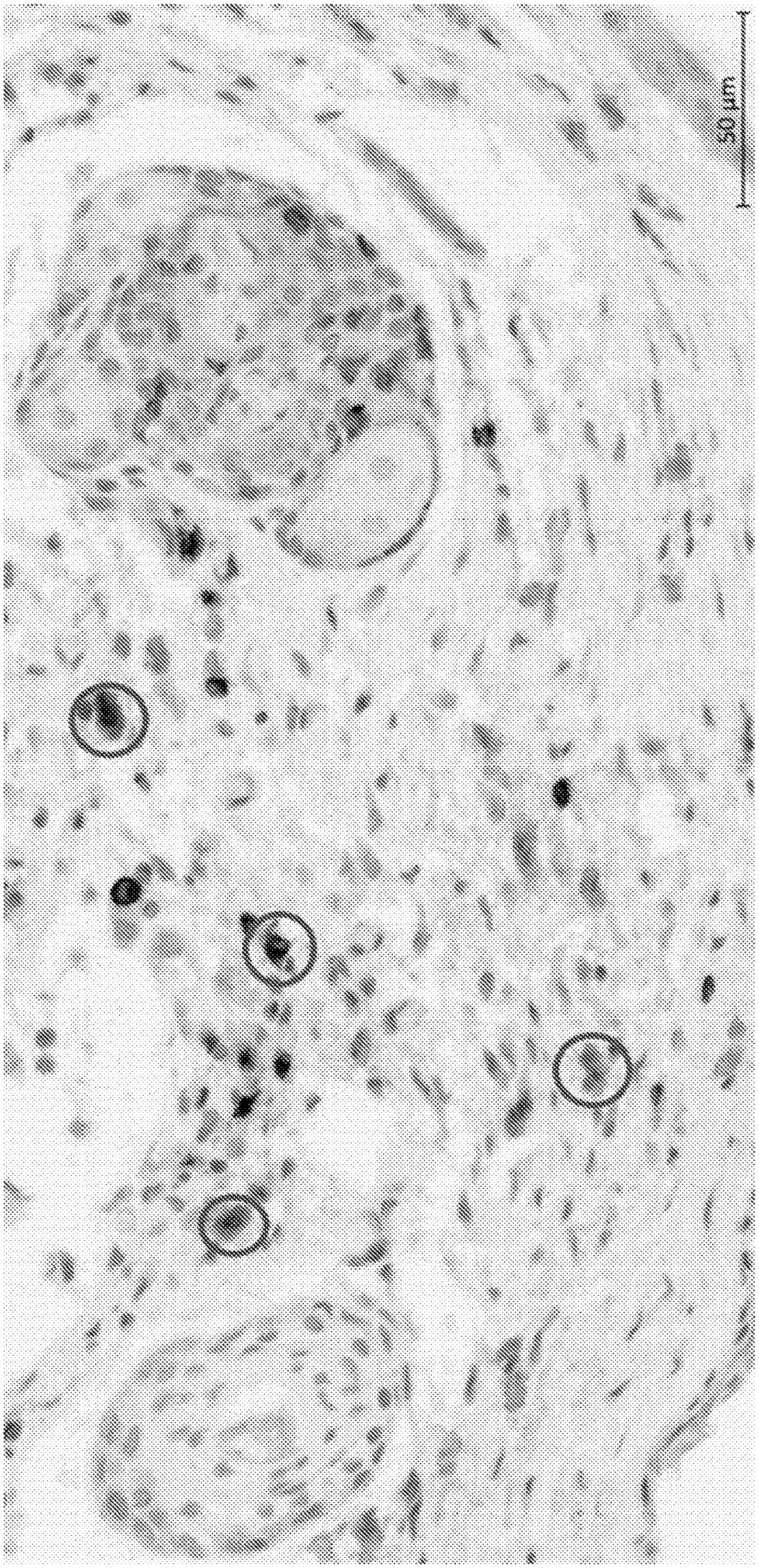

FIG. 22C shows an image obtained from immunohistochemistry (IHC) staining for $CD3^+$ cells, with cell nuclei (dark coloured spots) and CD3 (representatively circled) differentially labelled. Skin tissues from negative control mice and bio-implanted mice elicited comparable level of immune response. Pathological assessment reports 1+ for PCL-RGD. Image shown is representative with at least 4 C57BL/6 mice per group. Scale bar=50 μm.

Figure 22D:
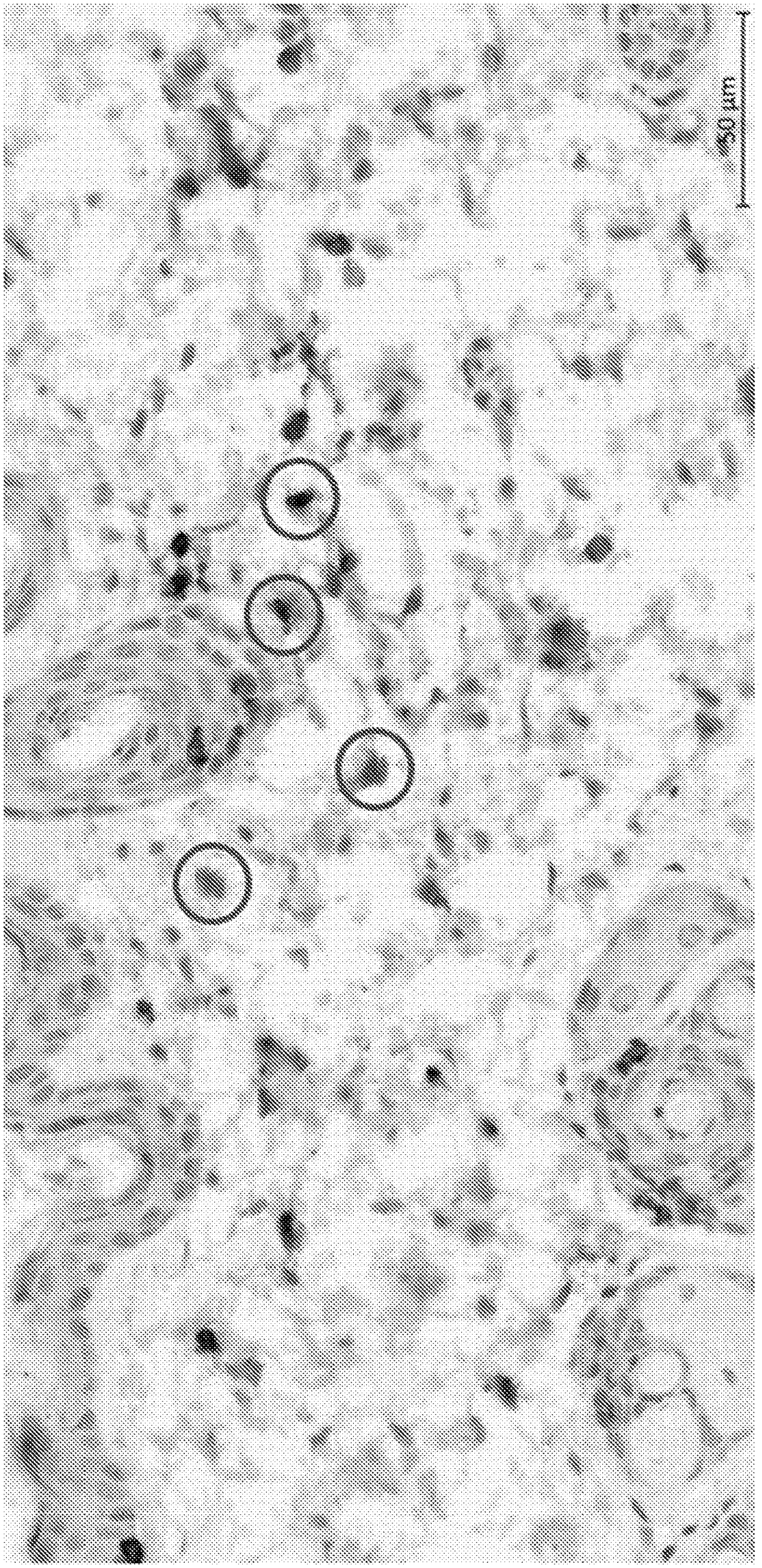

FIG. 22D shows an image obtained from immunohistochemistry (IHC) staining for $CD3^+$ cells, with cell nuclei (dark coloured spots) and CD3 (representatively circled) differentially labelled. Skin tissues from negative control mice and bio-implanted mice elicited comparable level of immune response. Pathological assessment reports 1+ for PCL-GPHP. Image shown is representative with at least 4 C57BL/6 mice per group. Scale bar=50 μm.

Figure 23A:
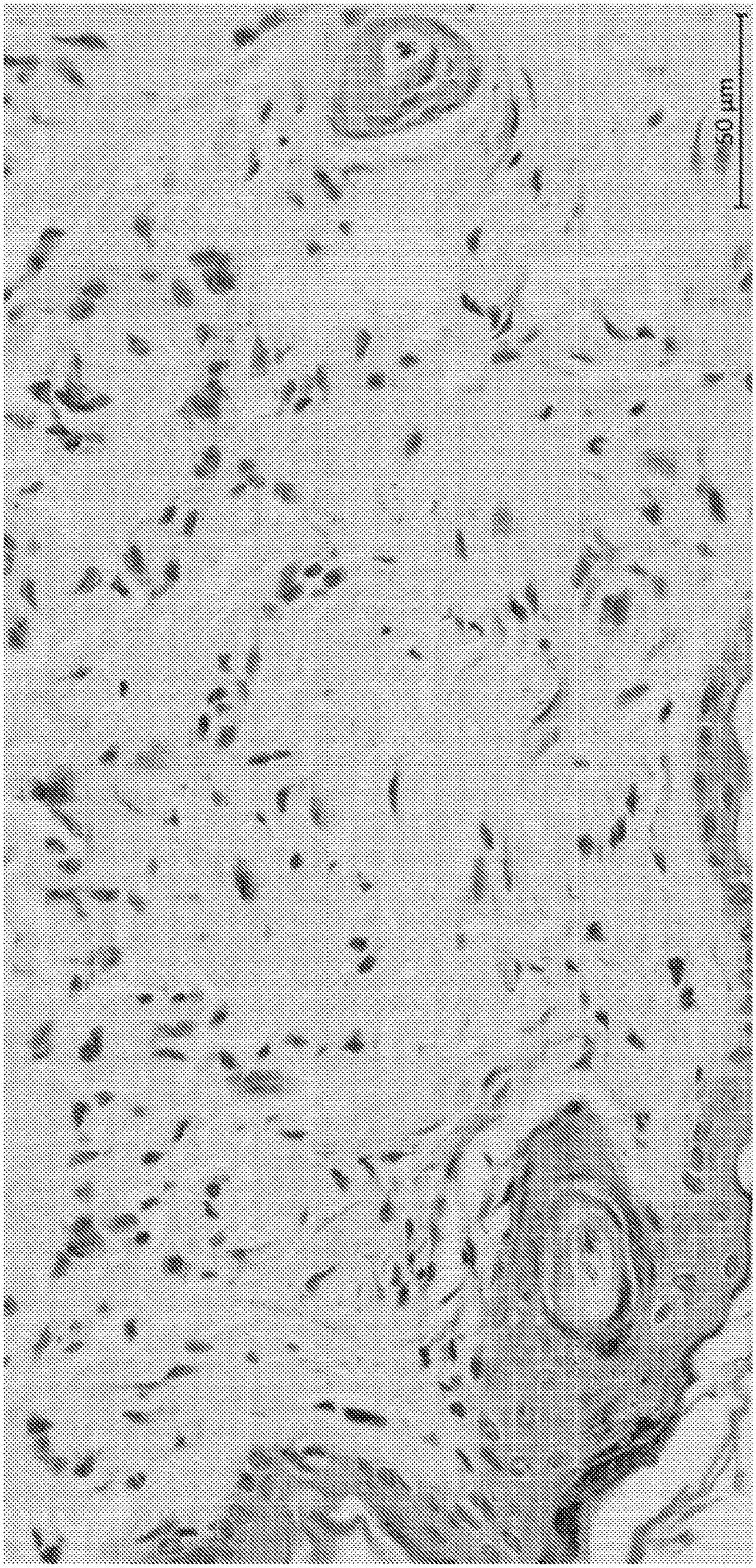

FIG. 23A shows an image obtained from Hematoxylin and Eosin (H&E) staining, with nuclear component (hematoxylin) and cytoplasmic components (eosin) differentially stained. Skin tissues from negative control mice and bio-implanted mice elicited comparable level of immune response. Pathological assessment reports 1+ for negative control. Image shown is representative with at least 4 C57BL/6 mice per group. Scale bar=50 μm.

Figure 23B:
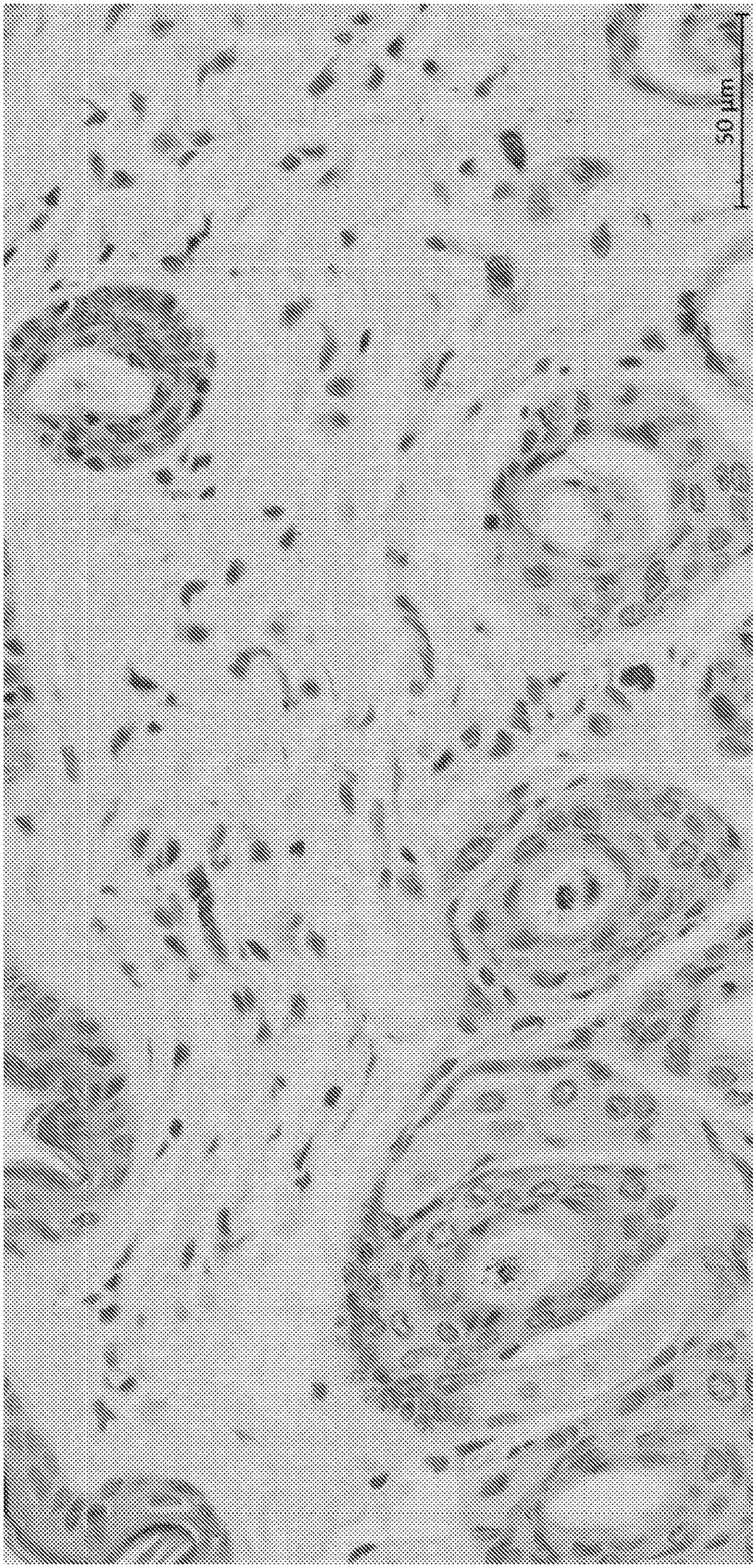

FIG. 23B shows an image obtained from Hematoxylin and Eosin (H&E) staining, with nuclear component (hematoxylin) and cytoplasmic components (eosin) differentially stained. Skin tissues from negative control mice and bio-implanted mice elicited comparable level of immune response. Pathological assessment reports 1+ for PCL. Image shown is representative with at least 4 $C_{57}$BL/6 mice per group. Scale bar=50 μm.

Figure 23C:
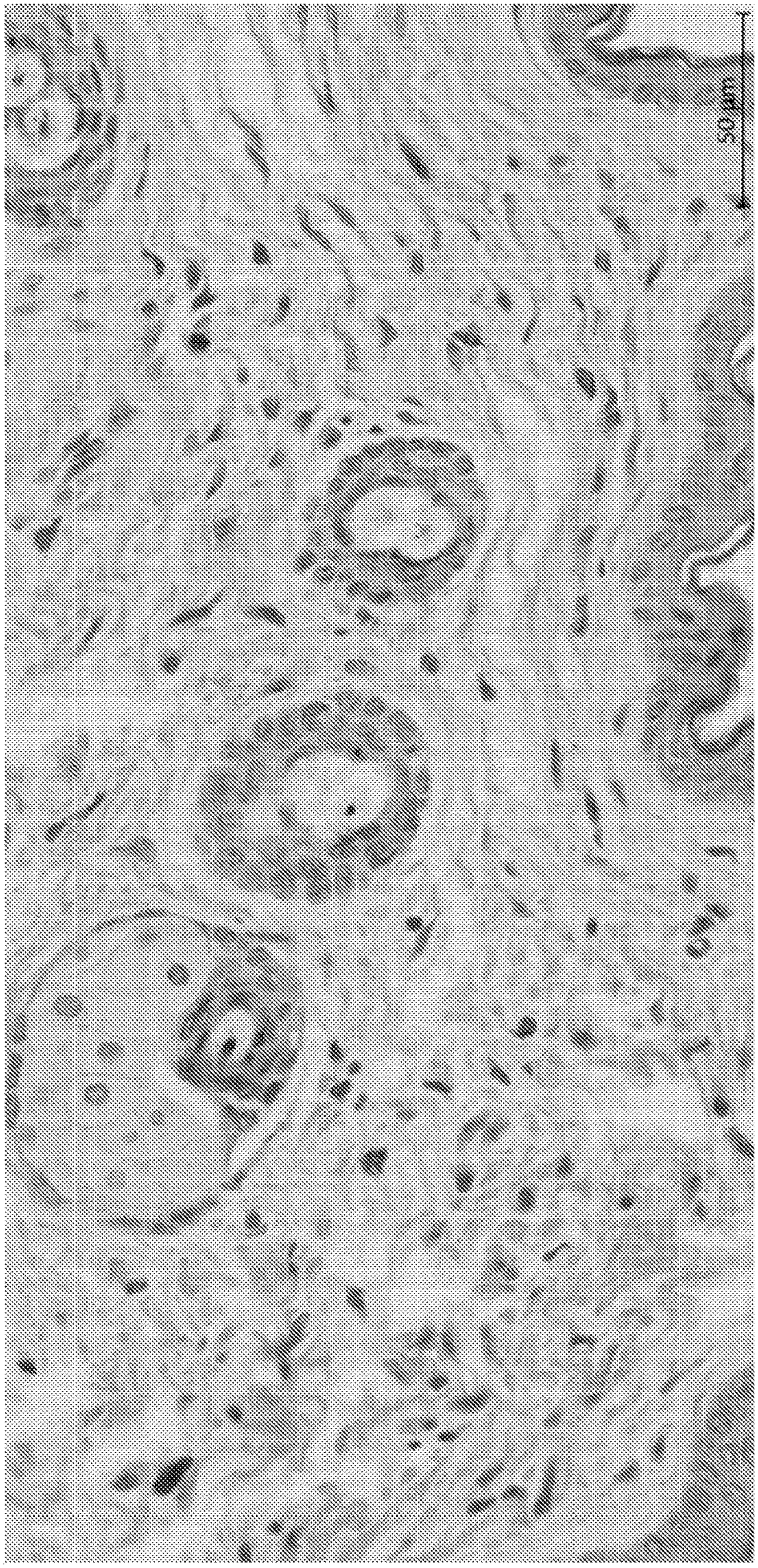

FIG. 23C shows an image obtained from Hematoxylin and Eosin (H&E) staining, with nuclear component (hematoxylin) and cytoplasmic components (eosin) differentially stained. Skin tissues from negative control mice and bio-implanted mice elicited comparable level of immune response. Pathological assessment reports 1+ for PCL-RGD. Image shown is representative with at least 4 C57BL/6 mice per group. Scale bar=50 μm.

Figure 23D:
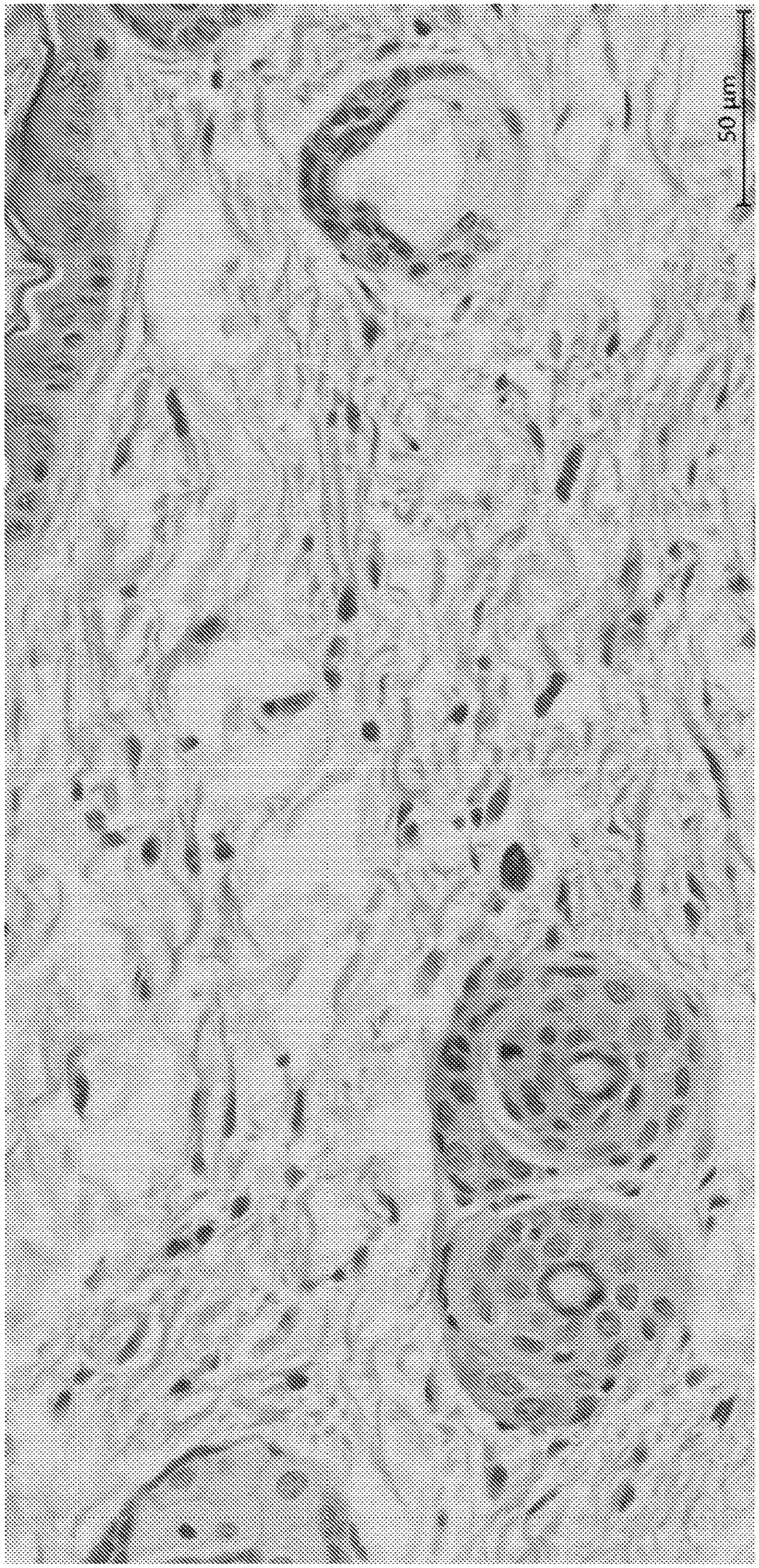

FIG. 23D shows an image obtained from Hematoxylin and Eosin (H&E) staining, with nuclear component (hematoxylin) and cytoplasmic components (eosin) differentially stained. Skin tissues from negative control mice and bio-implanted mice elicited comparable level of immune response. Pathological assessment reports 1+ for PCL-GPHP. Image shown is representative with at least 4 C57BL/6 mice per group. Scale bar=50 μm.

FIG. 24 and FIG. 25 show a bio-implanted murine skin tissues using PLA-based materials in accordance with various embodiments disclosed herein.

Figure 24A:

FIG. 24A shows an image obtained from immunohistochemistry (IHC) staining for $CD3^+$ cells, with cell nuclei (dark coloured spots) and CD3 (representatively circled) differentially labelled. Pathological assessment reports 1+ for negative control. Image shown is representative with at least 4 C57BL/6 mice per group. Scale bar=50 μm.

Figure 24B:
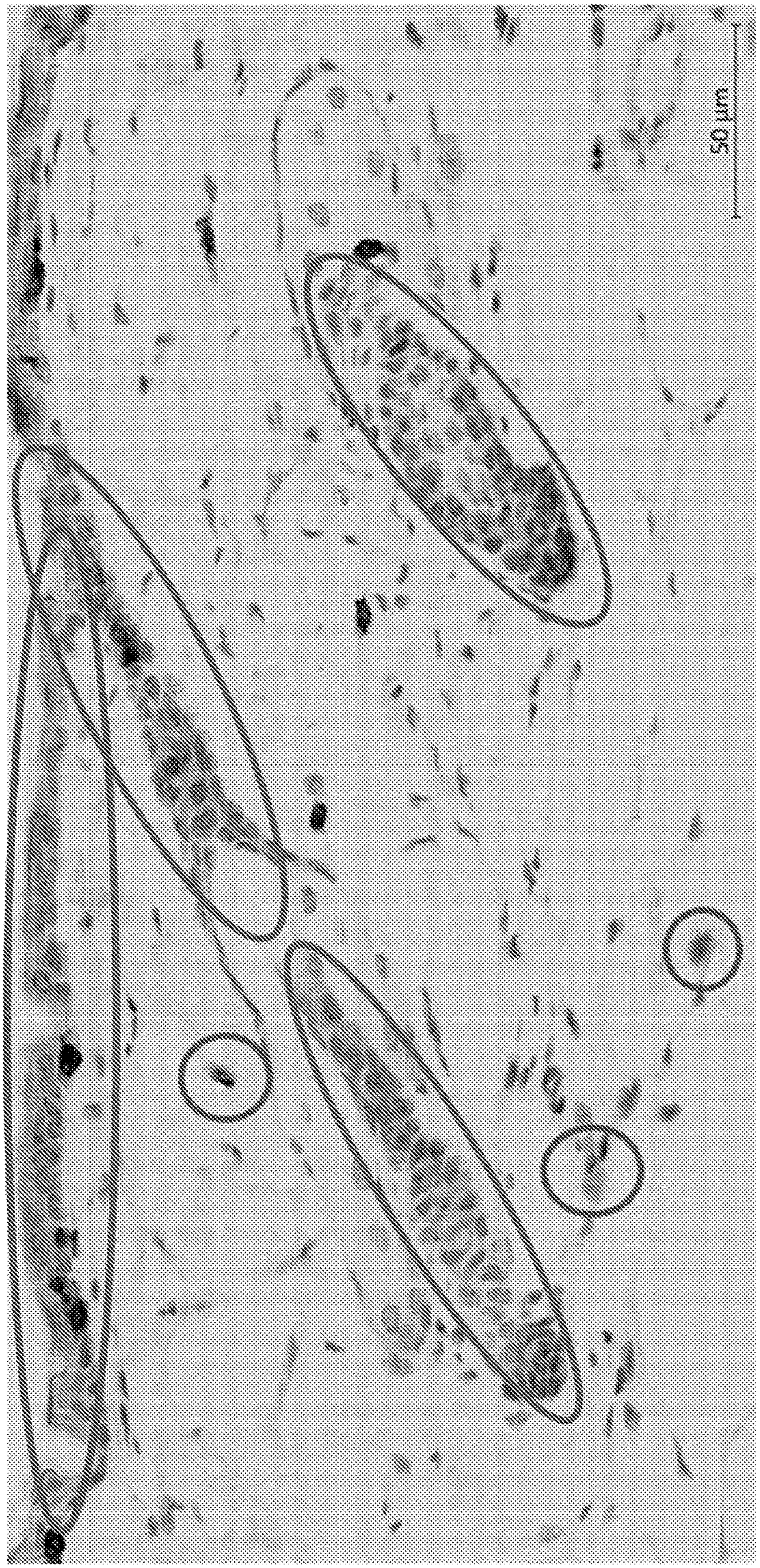

FIG. 24B shows an image obtained from immunohistochemistry (IHC) staining for $CD3^+$ cells, with cell nuclei (dark coloured spots) and CD3 (representatively circled) differentially labelled. Pathological assessment reports 1+ for PLA. Image shown is representative with at least 4 C57BL/6 mice per group. Scale bar=50 μm.

Figure 24C:
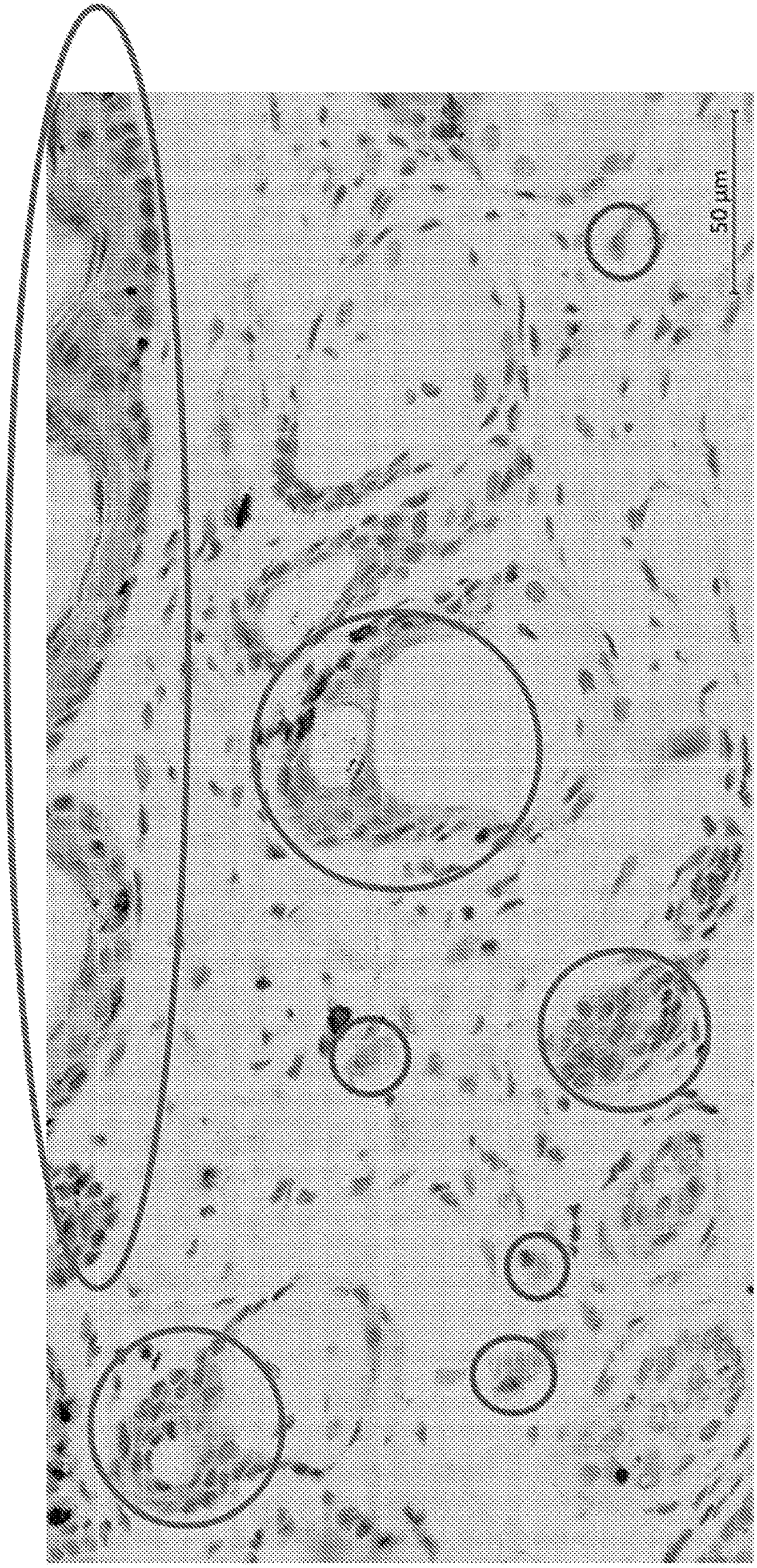

FIG. 24C shows an image obtained from immunohistochemistry (IHC) staining for $CD3^+$ cells, with cell nuclei (dark coloured spots) and CD3 (representatively circled) differentially labelled. Pathological assessment reports 1+ for PLA-HA. Image shown is representative with at least 4 C57BL/6 mice per group. Scale bar=50 μm.

Figure 24D:
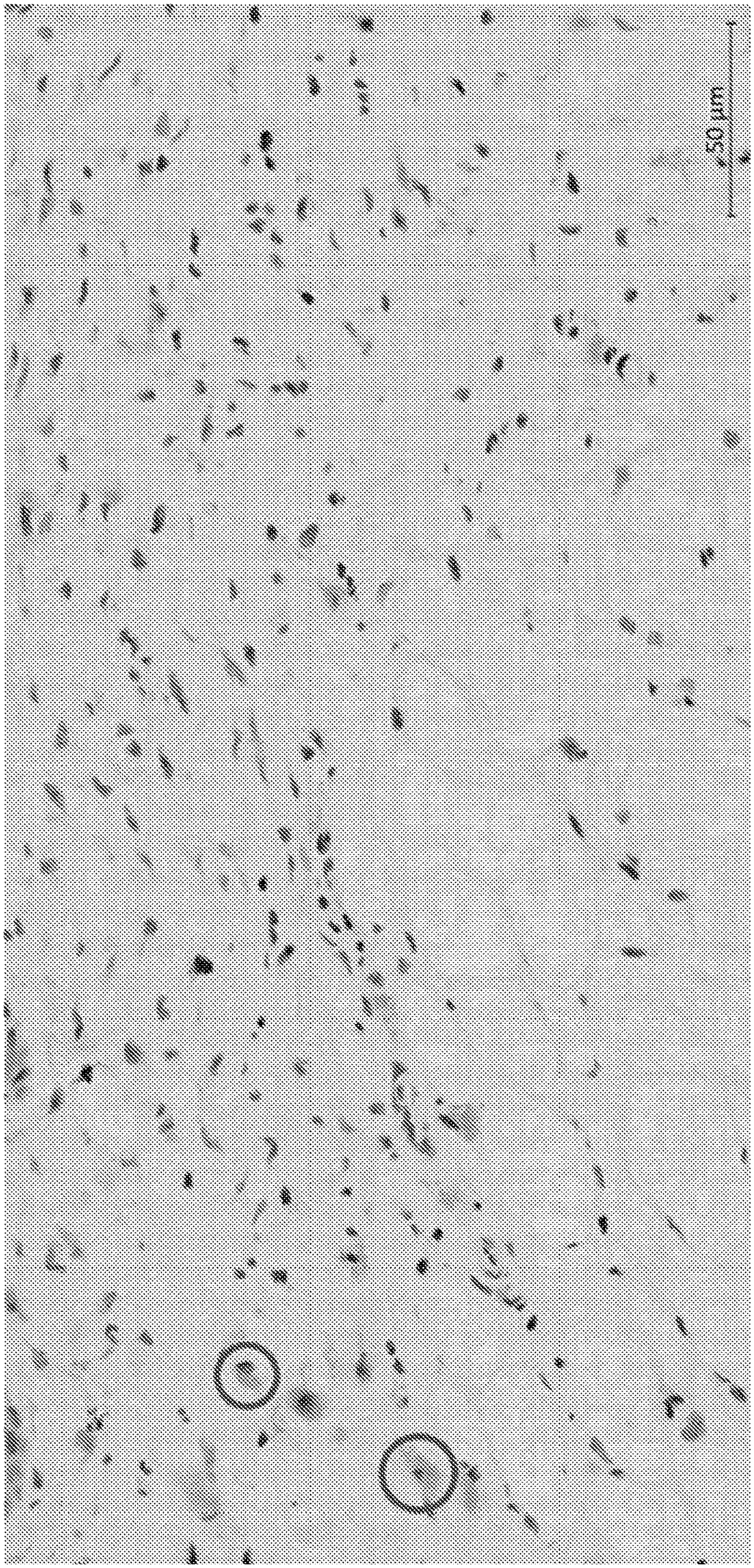

FIG. 24D shows an image obtained from immunohistochemistry (IHC) staining for $CD3^+$ cells, with cell nuclei (dark coloured spots) and CD3 (representatively circled) differentially labelled. Pathological assessment reports 0+ for PLA-RGD. Image shown is representative with at least 4 C57BL/6 mice per group. Scale bar=50 μm.

Figure 24E:
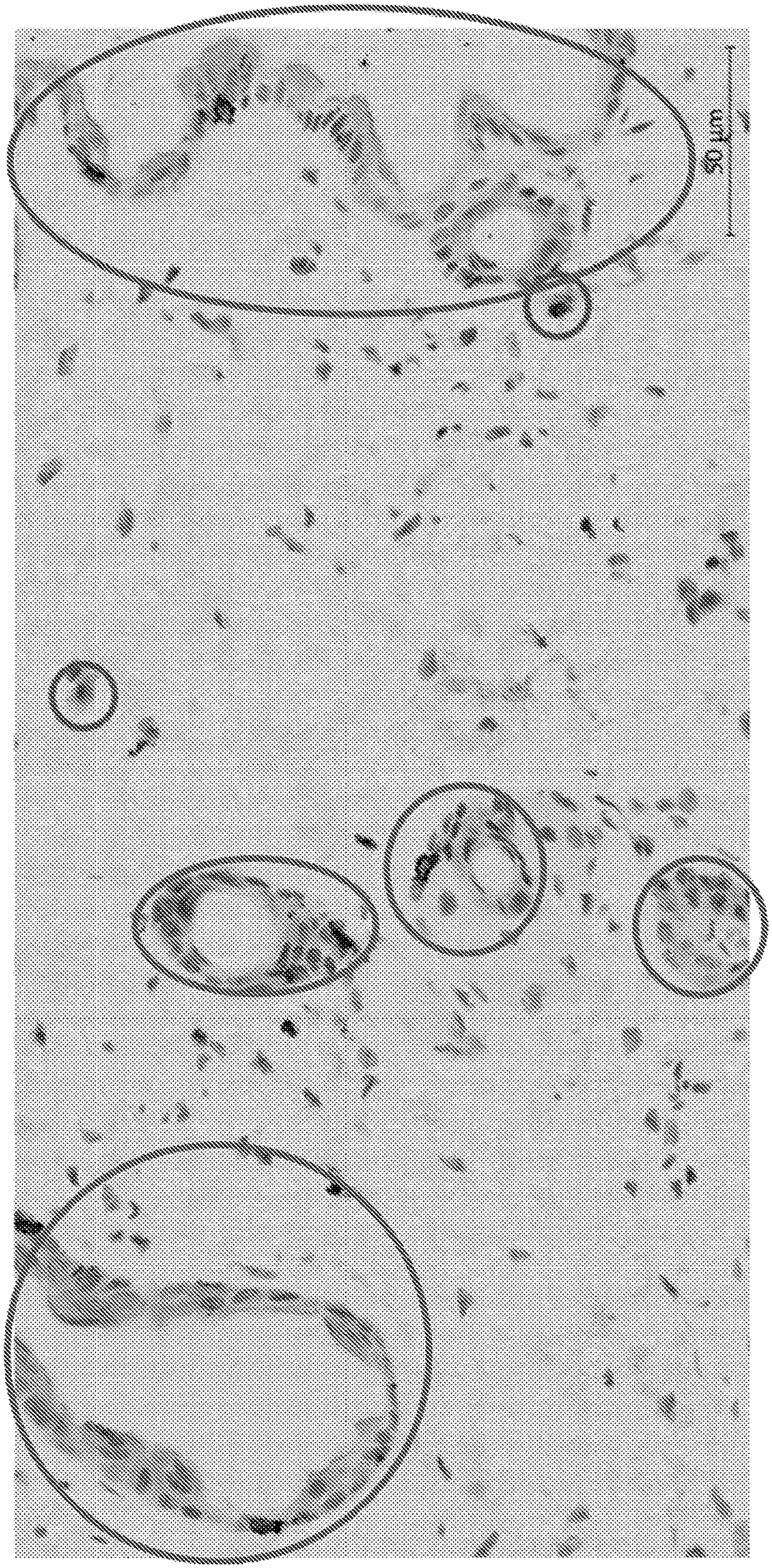

FIG. 24E shows an image obtained from immunohistochemistry (IHC) staining for $CD3^+$ cells, with cell nuclei (dark coloured spots) and CD3 (representatively circled) differentially labelled. Pathological assessment reports 1+ for PLA-GPHP. Image shown is representative with at least 4 C57BL/6 mice per group. Scale bar=50 μm.

Figure 25A:
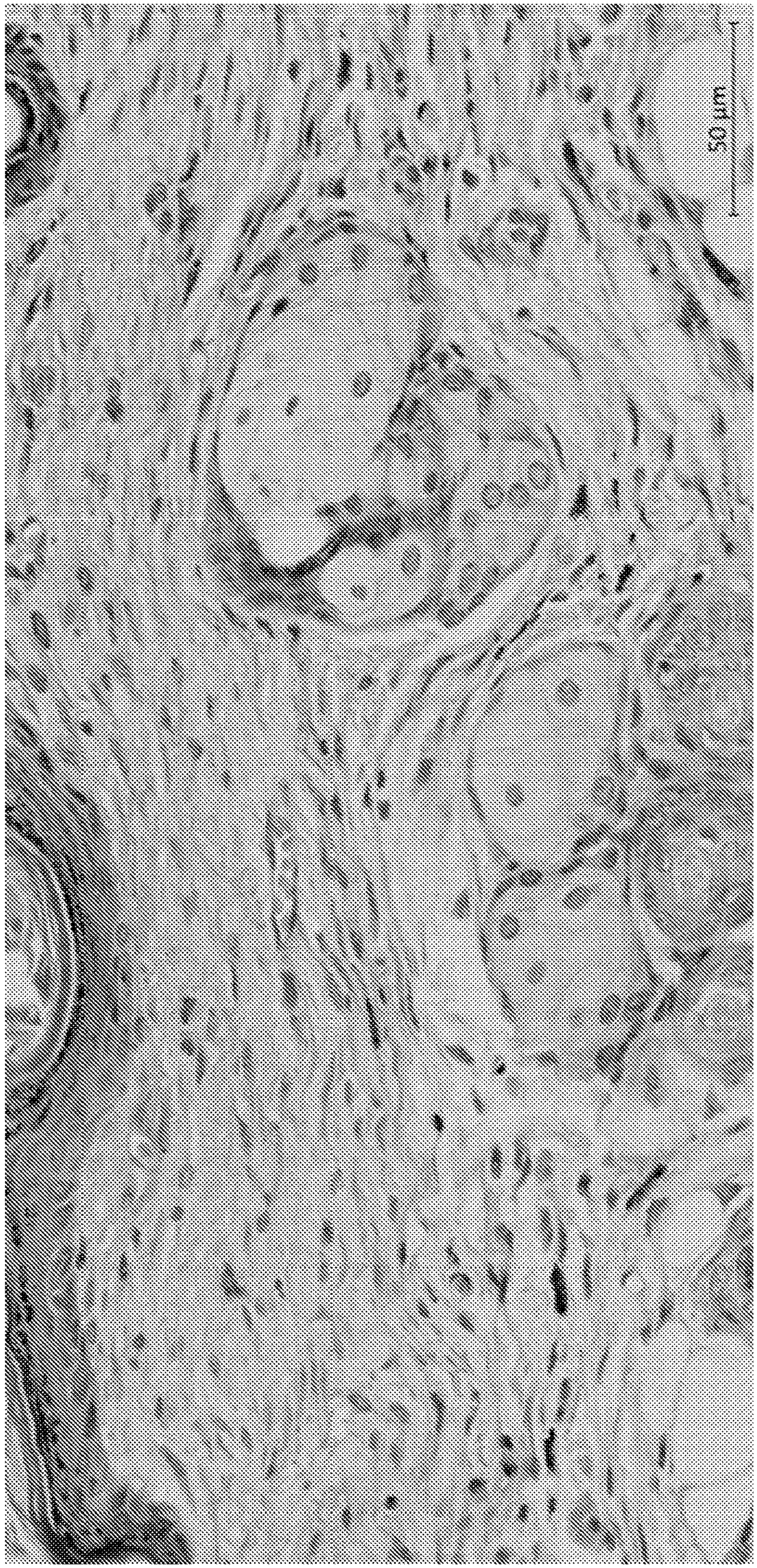

FIG. 25A shows an image obtained from Hematoxylin and Eosin (H&E) staining, with nuclear component (hematoxylin) and cytoplasmic components (eosin) differentially stained. Pathological assessment reports 1+ for negative control. Image shown is representative with at least 4 C57BL/6 mice per group. Scale bar=50 μm.

Figure 25B:
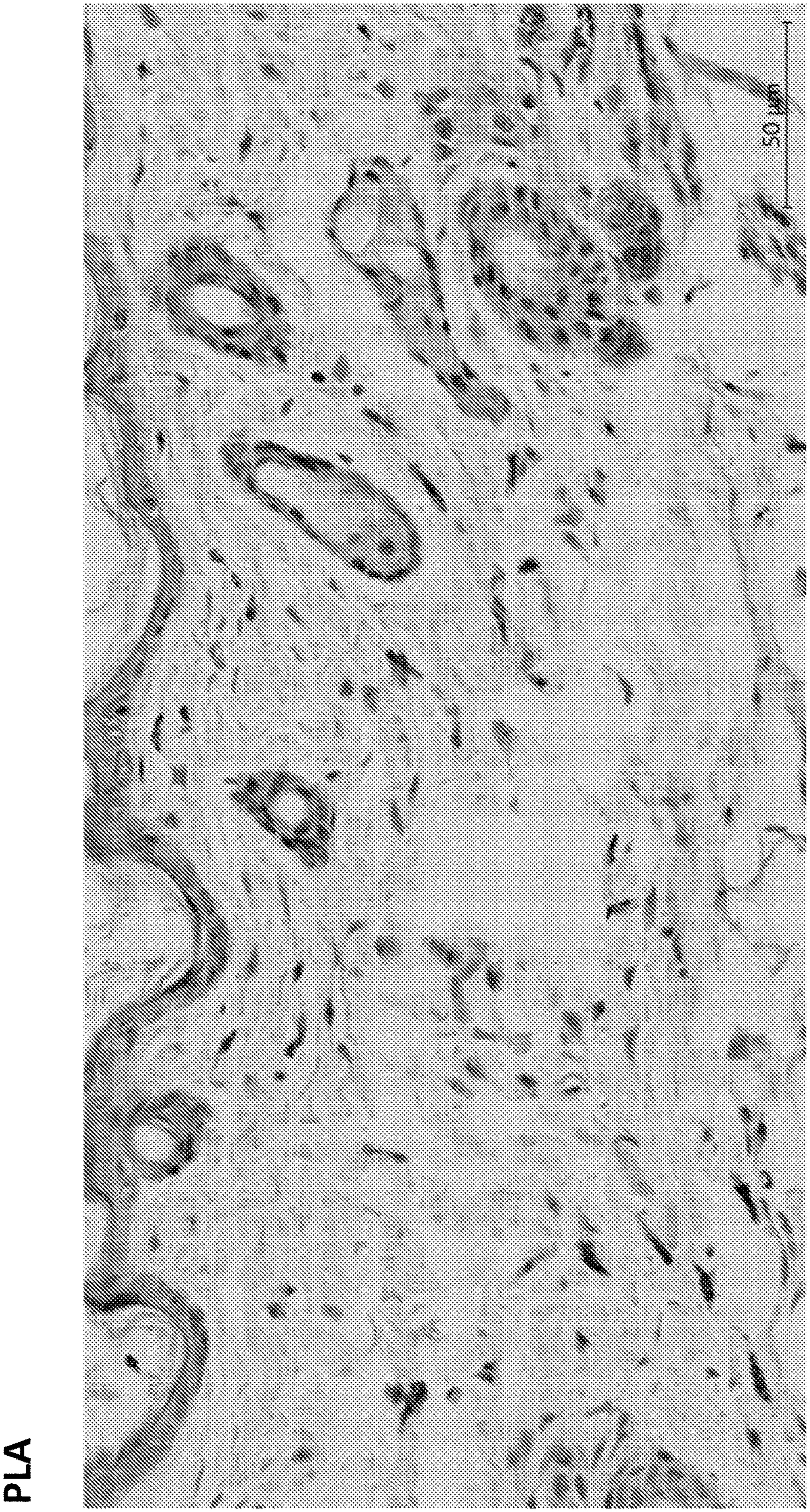

FIG. 25B shows an image obtained from Hematoxylin and Eosin (H&E) staining, with nuclear component (hematoxylin) and cytoplasmic components (eosin) differentially stained. Pathological assessment reports 1+ for PLA. Image shown is representative with at least 4 C57BL/6 mice per group. Scale bar=50 μm.

Figure 25C:

FIG. 25C shows an image obtained from Hematoxylin and Eosin (H&E) staining, with nuclear component (hematoxylin) and cytoplasmic components (eosin) differentially stained. Pathological assessment reports 1+ for PLA-HA. Image shown is representative with at least 4 C57BL/6 mice per group. Scale bar=50 μm.

Figure 25D:
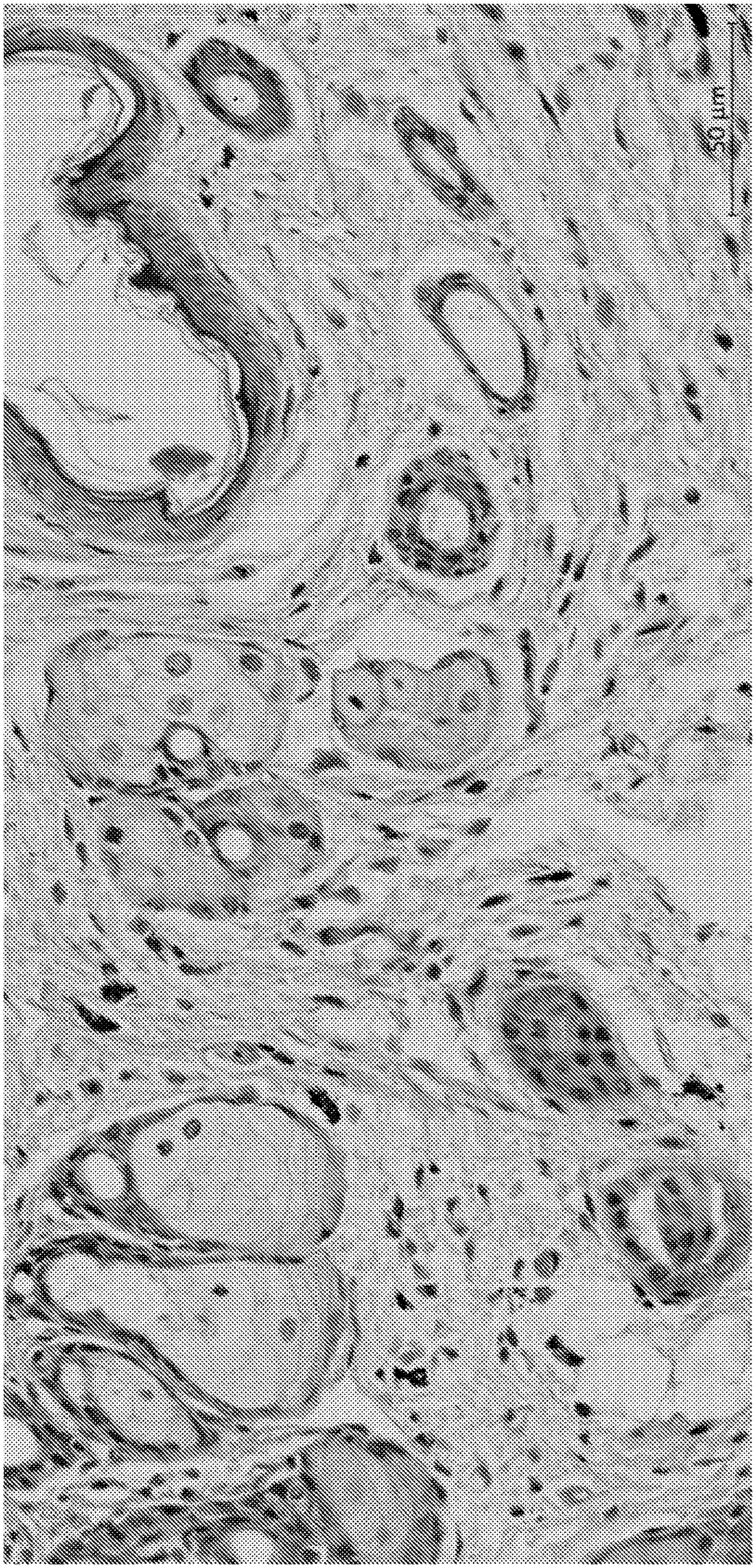

FIG. 25D shows an image obtained from Hematoxylin and Eosin (H&E) staining, with nuclear component (hematoxylin) and cytoplasmic components (eosin) differentially stained. Pathological assessment reports 0+ for PLA-RGD. Image shown is representative with at least 4 C57BL/6 mice per group. Scale bar=50 μm.

Figure 25E:
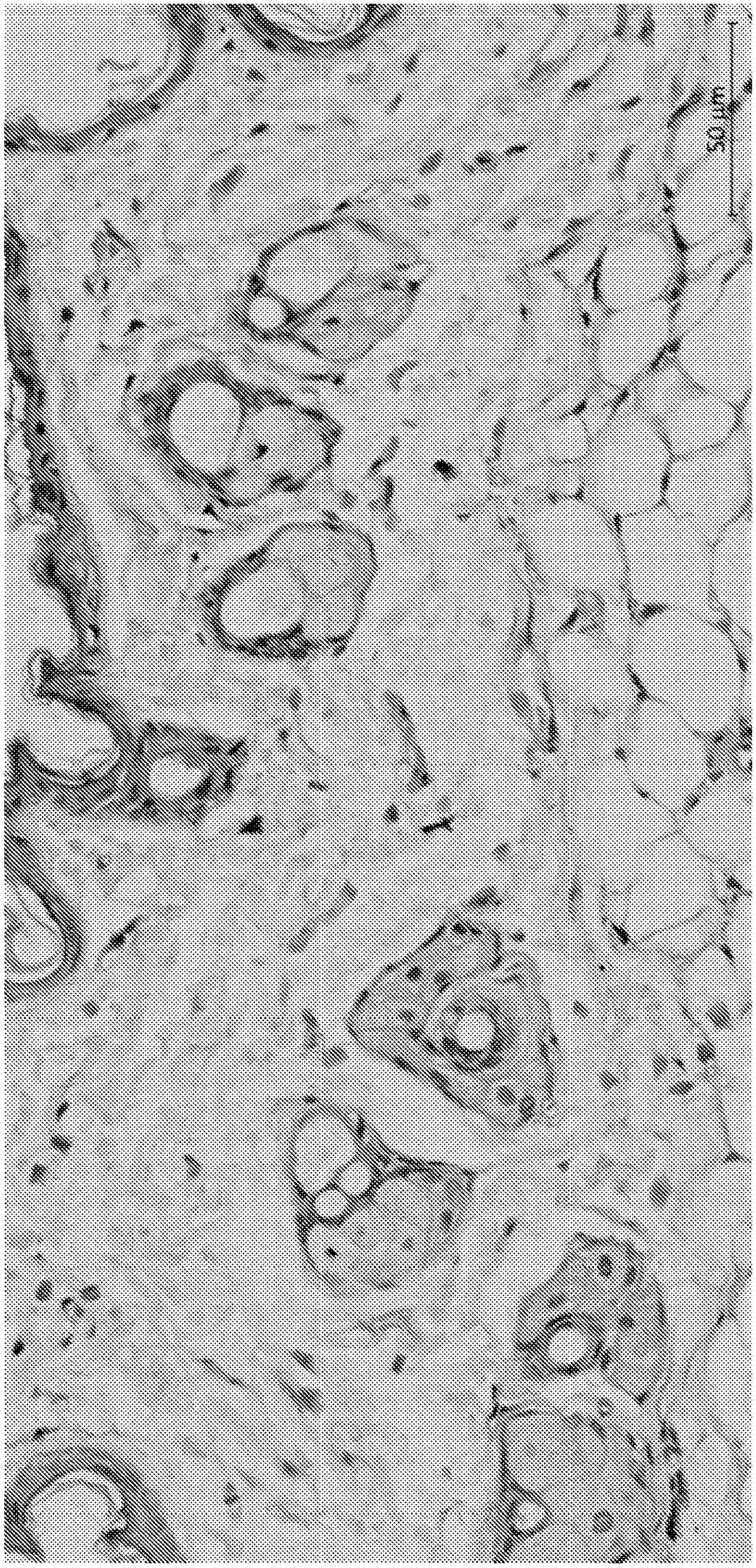

FIG. 25E shows an image obtained from Hematoxylin and Eosin (H&E) staining, with nuclear component (hematoxylin) and cytoplasmic components (eosin) differentially stained. Pathological assessment reports 1+ for PLA-GPHP. Image shown is representative with at least 4 C57BL/6 mice per group. Scale bar=50 μm.

FIG. 26 and FIG. 27 show a bio-implanted murine skin tissues using PLGA-based materials in accordance with various embodiments disclosed herein.

Figure 26A:
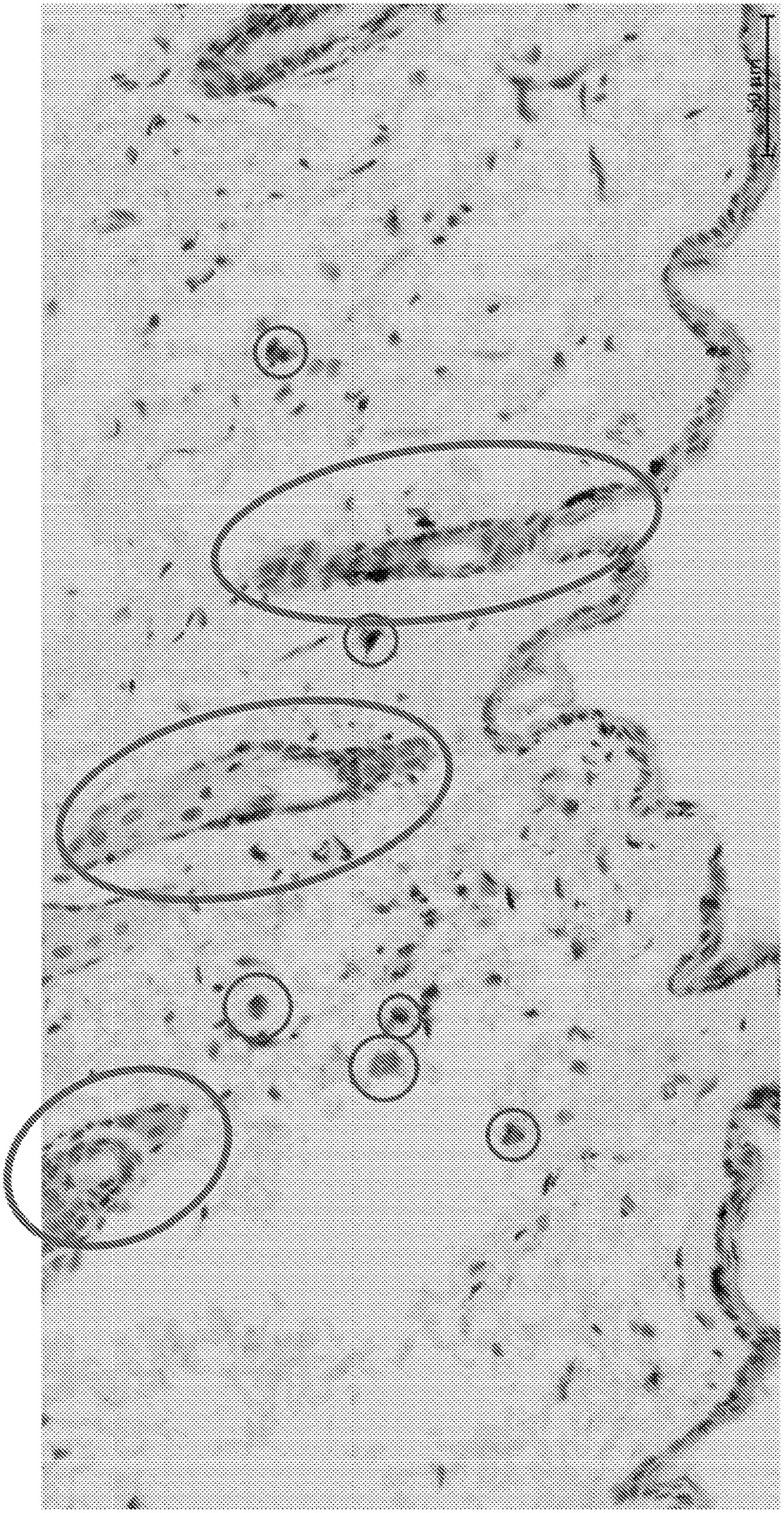

FIG. 26A shows an image obtained from immunohistochemistry (IHC) staining for $CD3^+$ cells, with cell nuclei (dark coloured spots) and CD3 (representatively circled) differentially labelled. Pathological assessment reports 2+ for negative control. Image shown is representative with at least 4 C57BL/6 mice per group. Scale bar=50 μm.

Figure 26B:
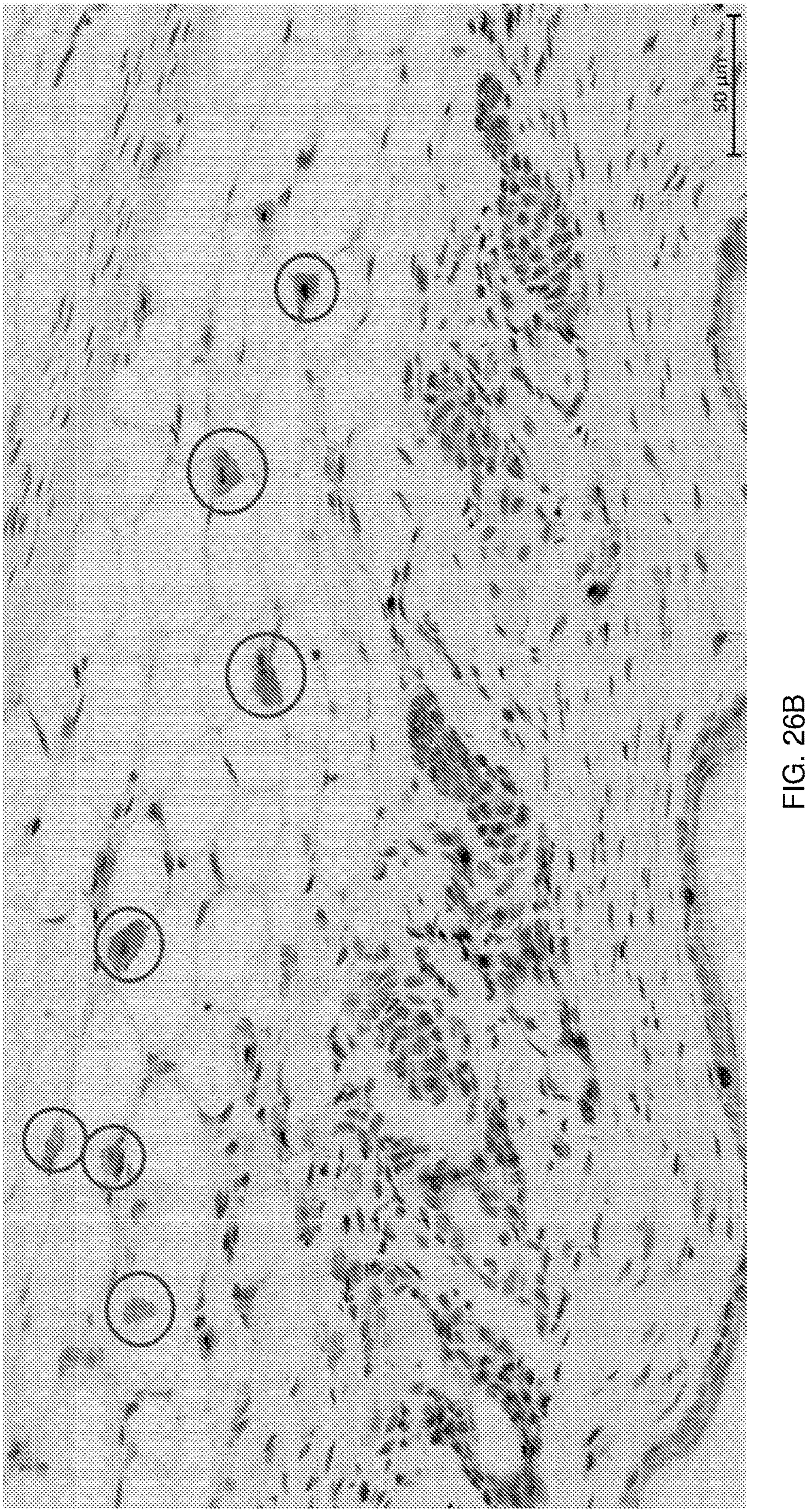

FIG. 26B shows an image obtained from immunohistochemistry (IHC) staining for $CD3^+$ cells, with cell nuclei (dark coloured spots) and CD3 (representatively circled) differentially labelled. Pathological assessment reports 2+ for PLGA. Image shown is representative with at least 4 C57BL/6 mice per group. Scale bar=50 μm.

Figure 26C:
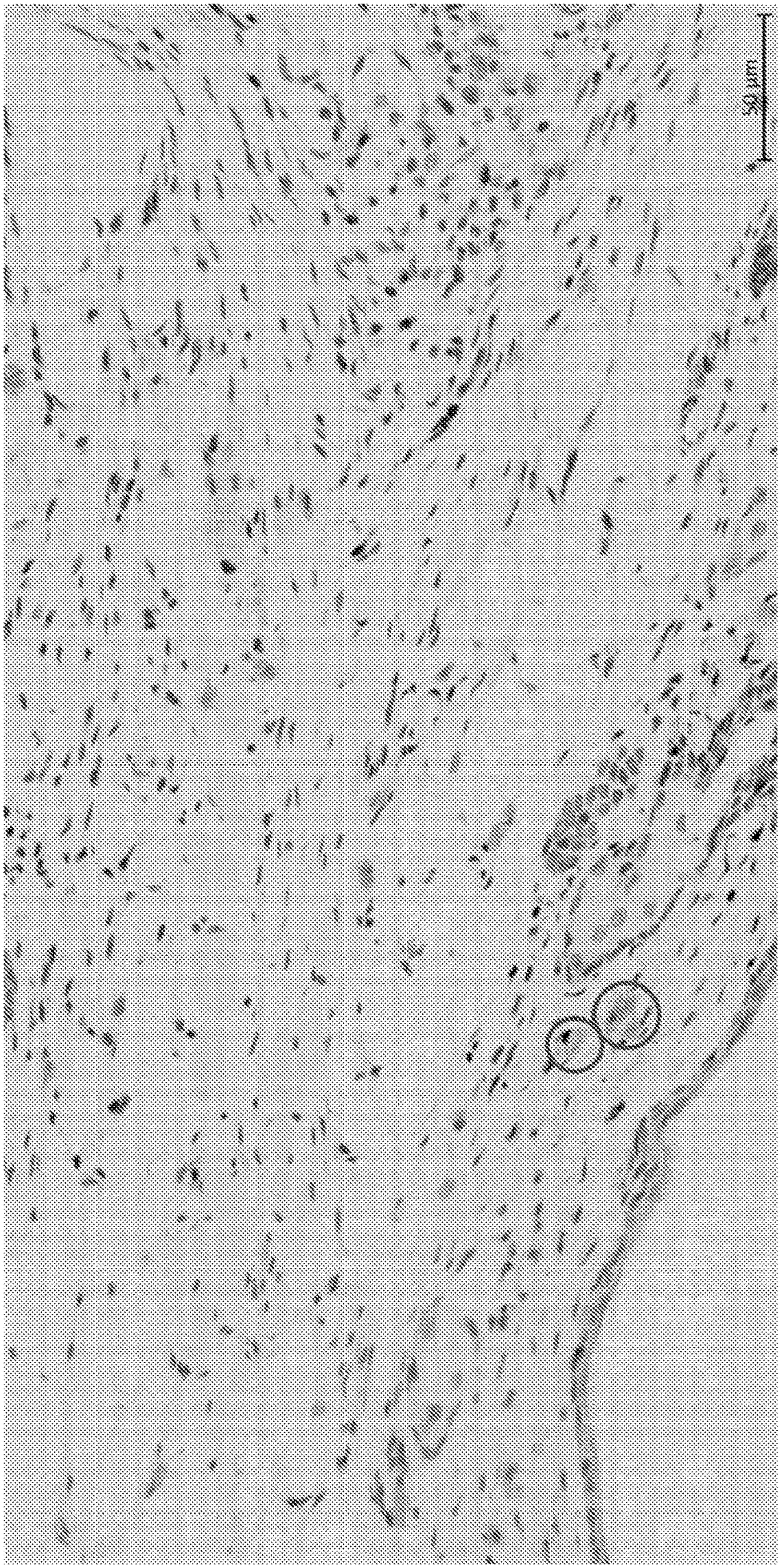

FIG. 26C shows an image obtained from immunohistochemistry (IHC) staining for $CD3^+$ cells, with cell nuclei (dark coloured spots) and CD3 (representatively circled) differentially labelled. Pathological assessment reports 2+ for PLGA-RGD10%. Image shown is representative with at least 4 C57BL/6 mice per group. Scale bar=50 μm.

Figure 26D:
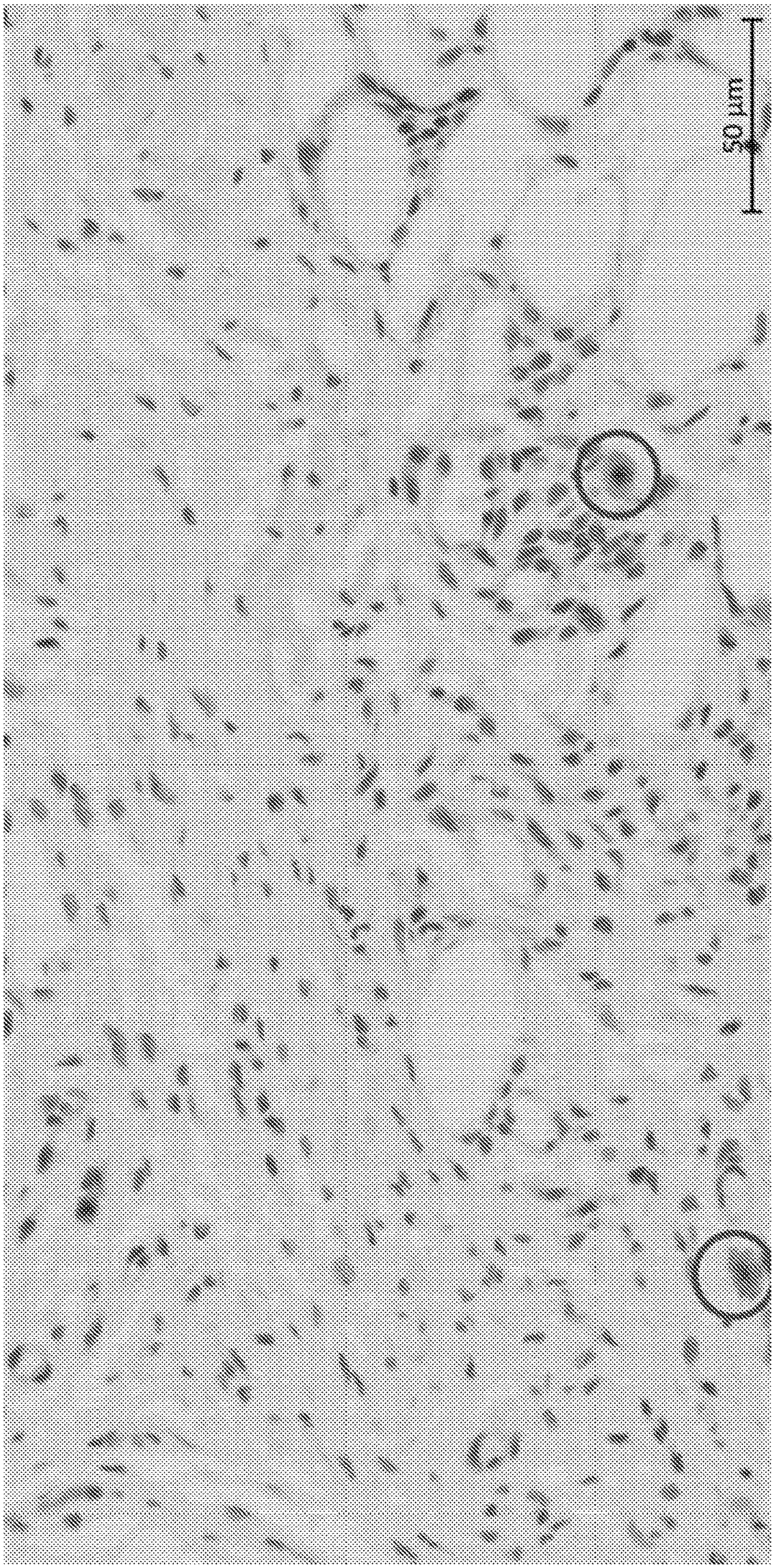

FIG. 26D shows an image obtained from immunohistochemistry (IHC) staining for $CD3^+$ cells, with cell nuclei (dark coloured spots) and CD3 (representatively circled) differentially labelled. Pathological assessment reports 1+ for PLGA-RGD20%. Image shown is representative with at least 4 C57BL/6 mice per group. Scale bar=50 μm.

Figure 27A:
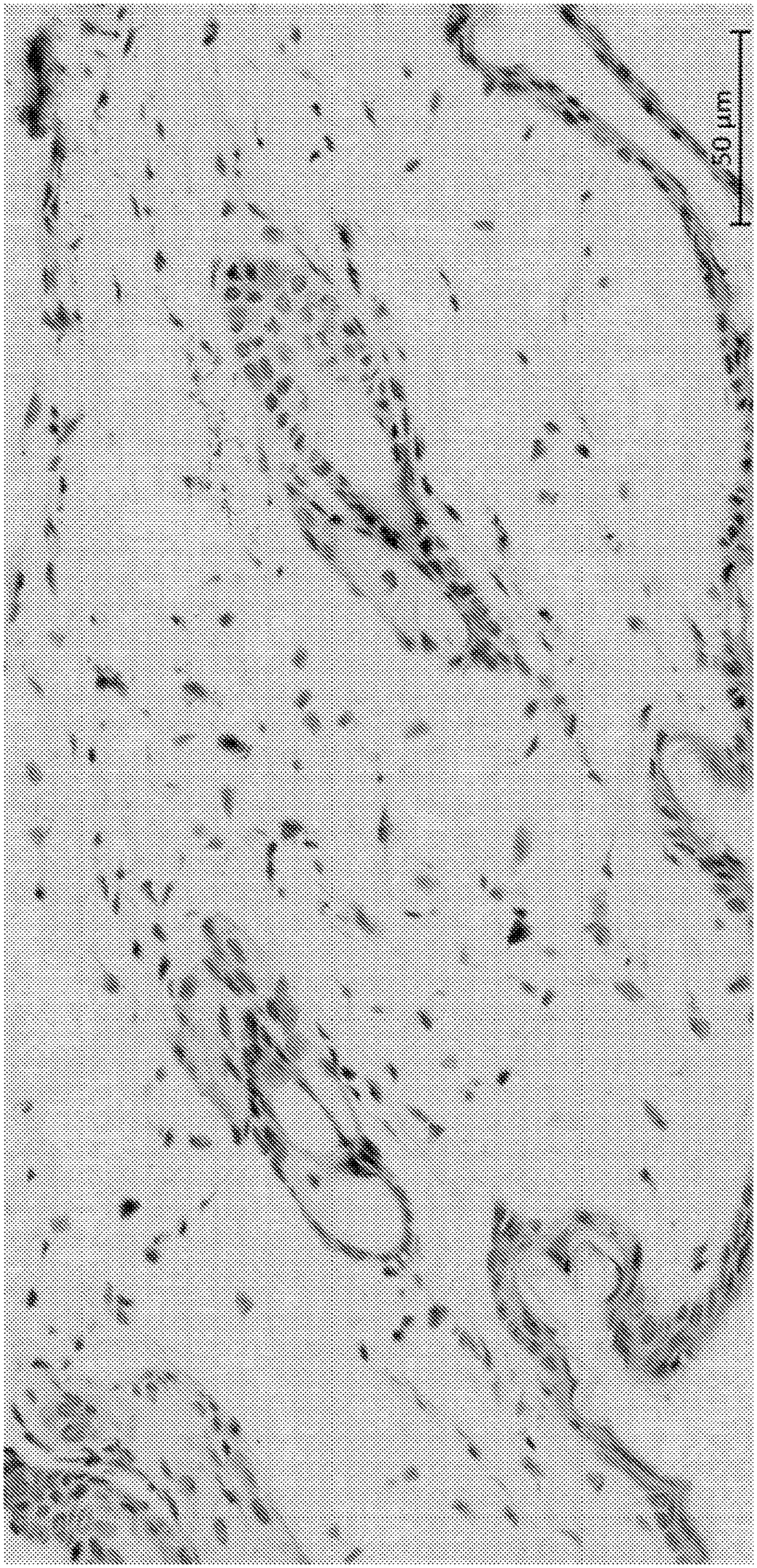

FIG. 27A shows an image obtained from Hematoxylin and Eosin (H&E) staining, with nuclear component (hematoxylin) and cytoplasmic components (eosin) differentially stained. Pathological assessment reports 2+ for negative control. Image shown is representative with at least 4 C57BL/6 mice per group. Scale bar=50 μm.

Figure 27B:
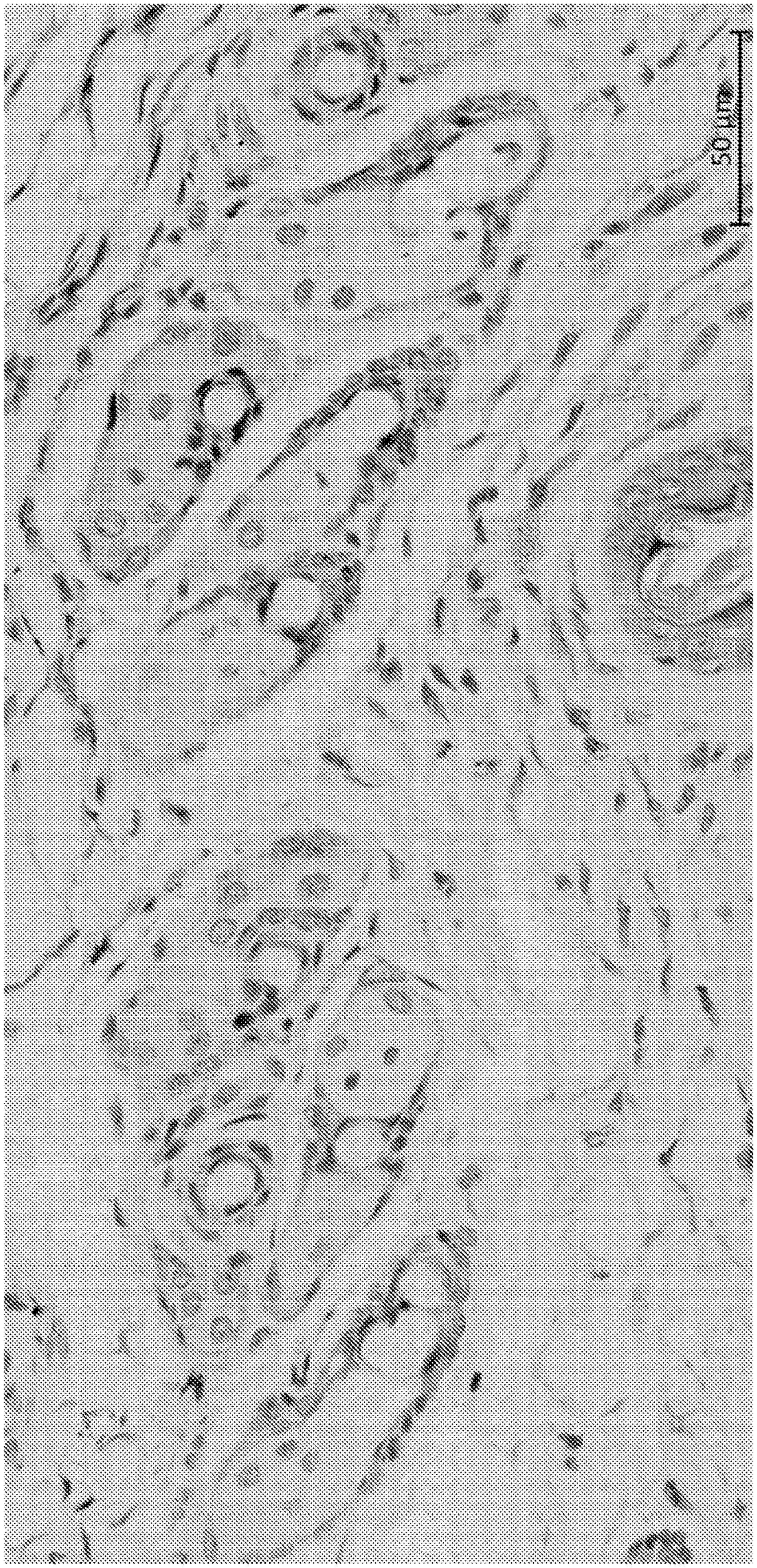

FIG. 27B shows an image obtained from Hematoxylin and Eosin (H&E) staining, with nuclear component (hematoxylin) and cytoplasmic components (eosin) differentially stained. Pathological assessment reports 2+ for PLGA. Image shown is representative with at least 4 C57BL/6 mice per group. Scale bar=50 μm.

Figure 27C:
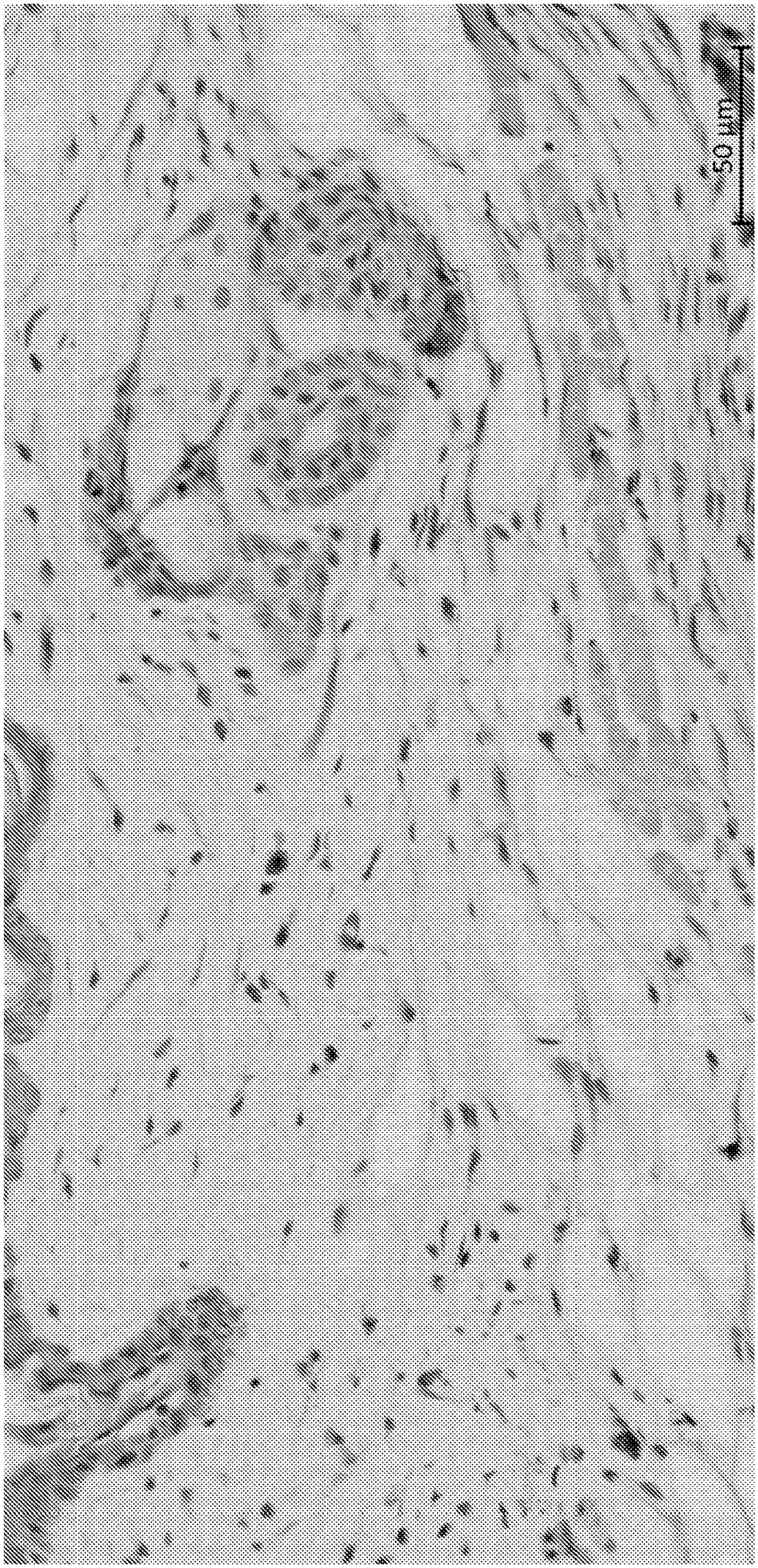

FIG. 27C shows an image obtained from Hematoxylin and Eosin (H&E) staining, with nuclear component (hematoxylin) and cytoplasmic components (eosin) differentially stained. Pathological assessment reports 2+ for PLGA-RGD10%. Image shown is representative with at least 4 C57BL/6 mice per group. Scale bar=50 μm.

Figure 27D:
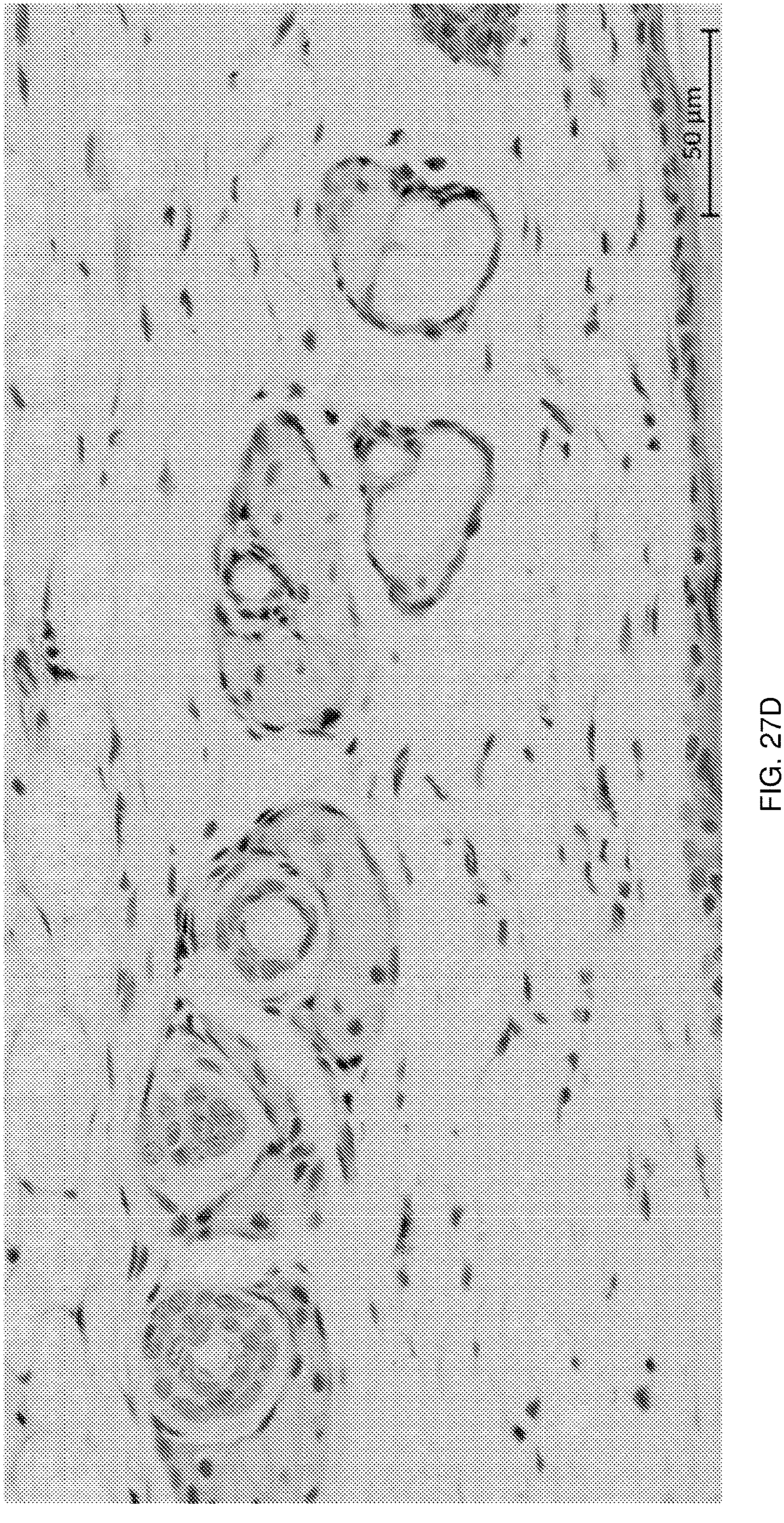

FIG. 27D shows an image obtained from Hematoxylin and Eosin (H&E) staining, with nuclear component (hematoxylin) and cytoplasmic components (eosin) differentially stained. Pathological assessment reports 1+ for PLGA-RGD20%. Image shown is representative with at least 4 C57BL/6 mice per group. Scale bar=50 μm.

Figure 28:

FIG. 28 shows Hematoxylin and Eosin (H&E) staining image of skin tissue around implantation site. PLGA was observed to be intact despite repeated washing and attempts to detach material from tissues. Skin tissues were also observed to fill up the void left behind by degraded PLGA (circled area).

Figure 29:
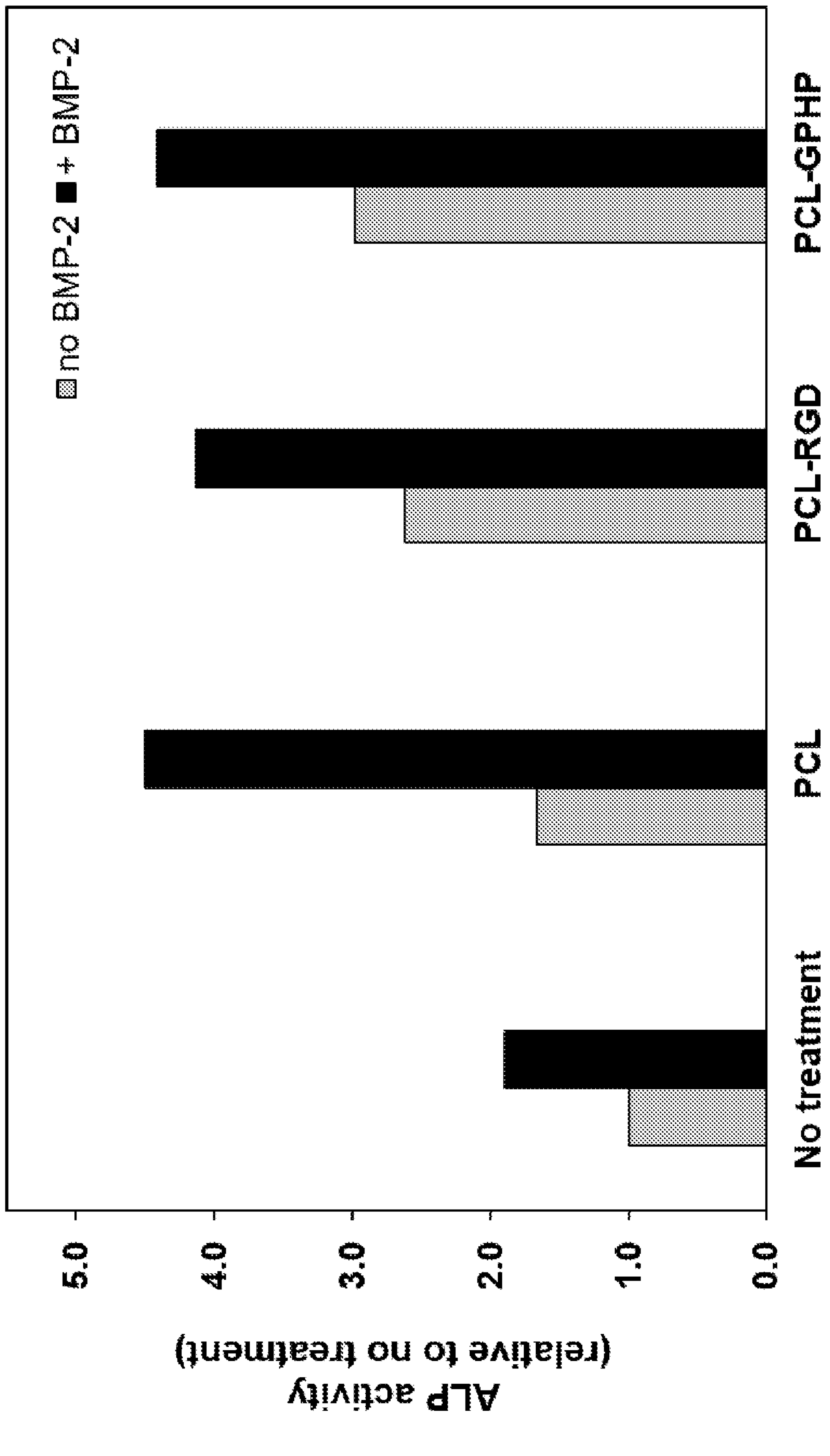

FIG. 29 shows alkaline phosphatase (ALP) activity of C2C12 cells cultured on PCL coupons pre-incubated with or without BMP-2 after 3 days. Data are represented as the mean ALP activity (n=2) relative to no treatment.

Figure 30:
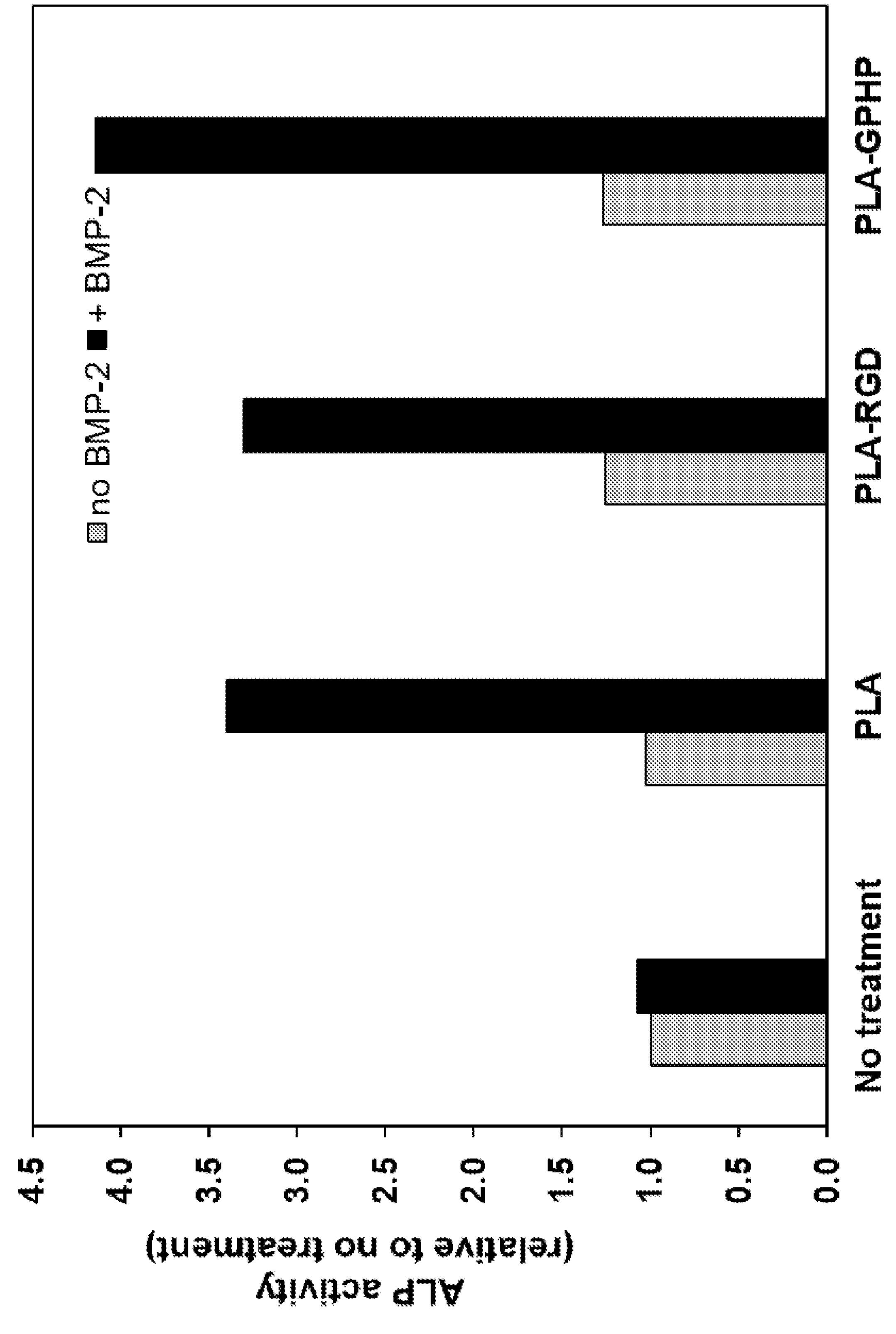

FIG. 30 shows alkaline phosphatase (ALP) activity of C2C12 cells cultured on PLA coupons pre-incubated with or without BMP-2 after 3 days. Data are represented as the mean ALP activity (n=2) relative to no treatment.

Figure 31:
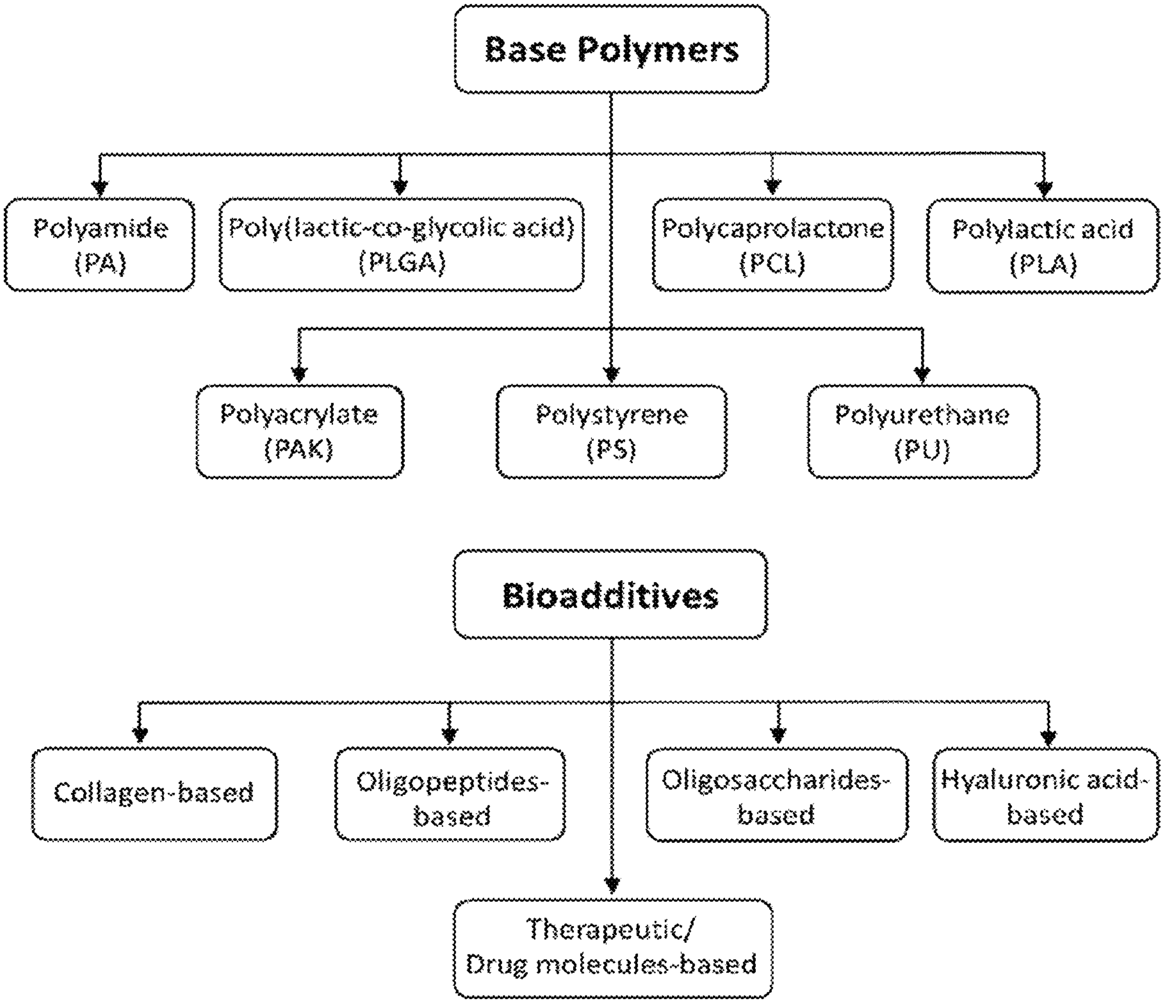

FIG. 31 is a scheme showing exemplary base polymers and bioadditives for manufacturing bioactive polymer filaments.

Figure 32:
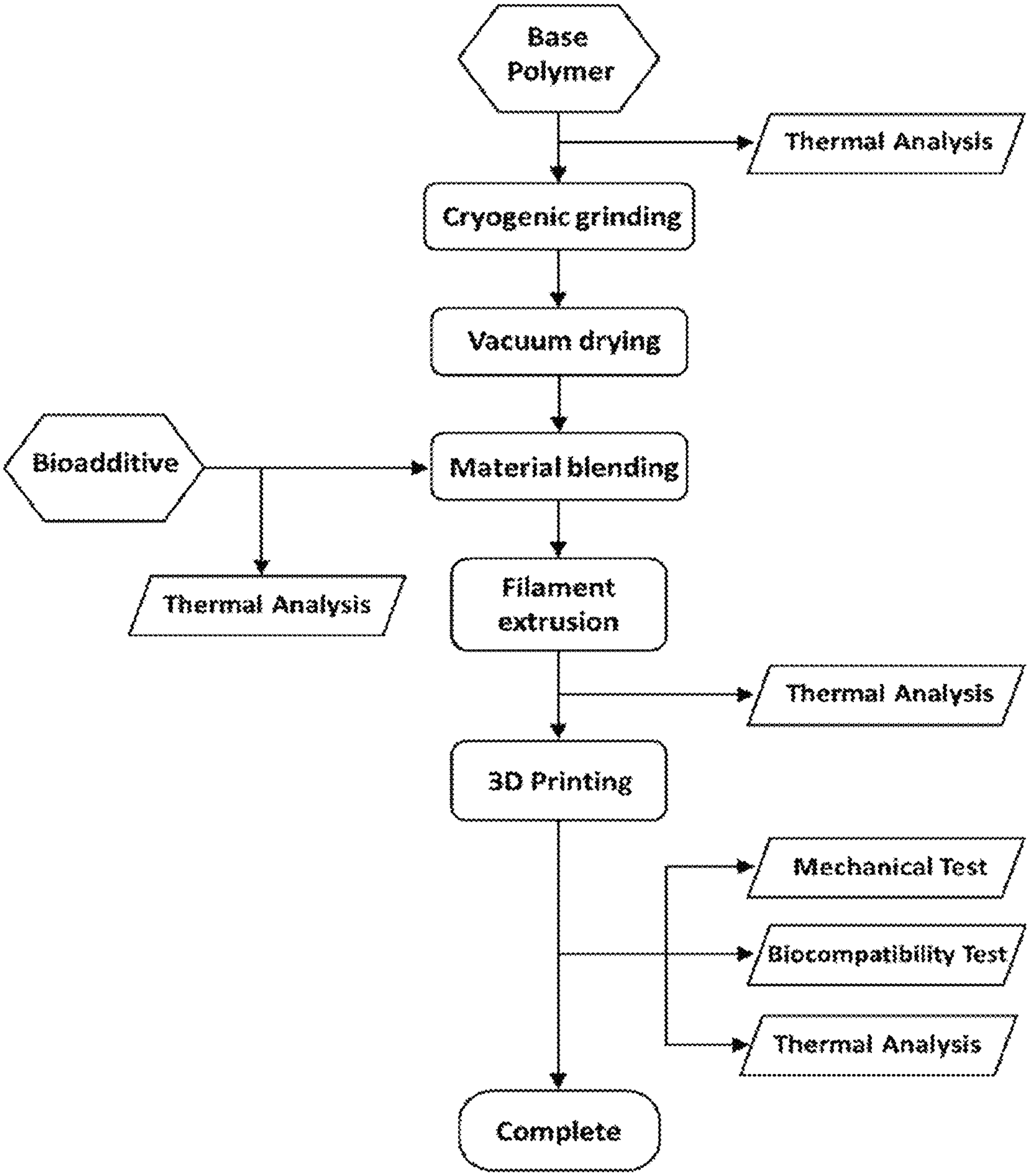

FIG. 32 is a scheme showing exemplary experimental process workflow for manufacturing bioactive polymer filaments.

Figure 33:
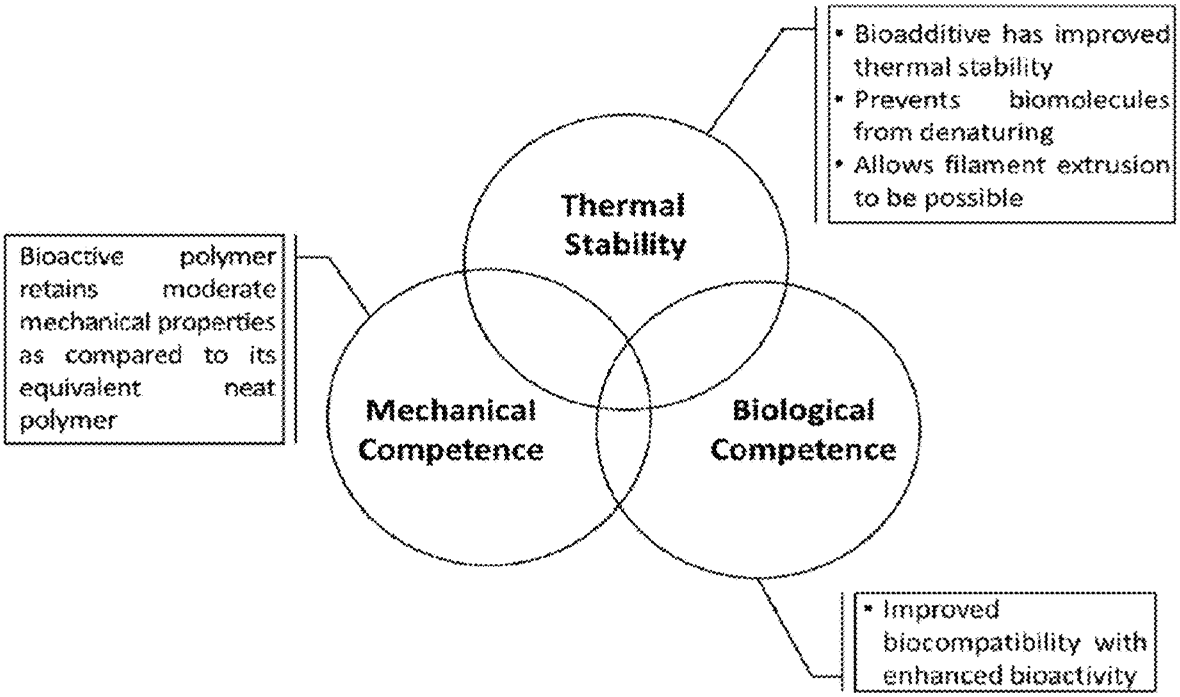

FIG. 33 is a scheme showing technical features of the bioactive polymer filament produced in accordance with various embodiments disclosed herein.

EXAMPLES

Example embodiments of the disclosure will be better understood and readily apparent to one of ordinary skill in the art from the following examples, tables and if applicable, in conjunction with the figures. It should be appreciated that other modifications related to structural, biological and/or chemical changes may be made without deviating from the scope of the invention. Example embodiments are not necessarily mutually exclusive as some may be combined with one or more embodiments to form new example embodiments. The example embodiments should not be construed as limiting the scope of the disclosure.

Fused filament fabrication (FFF) or fused deposition modelling (FDM) allows for end-to-end precise manufacturing of medical devices with biological and mechanical properties using suitable filament feedstock. Creation of filaments made of appropriate polymers is paramount to the utilization of FFF or FDM printing technology. The following examples present the technical process of creating filament made of bioactive polymers for FFF-based or FDM-based 3D printers with ø2.85 mm filament diameter configuration. Twin-screw extruder (TSE) was utilized in the examples to produce bioactive polymer filaments as it allows good mixing of base polymer and bioadditive while reducing residence time in the heated sections to avoid thermal degradation of material. Thermal analysis, mechanical test and biocompatibility tests were performed to determine the material properties for its mechanical and biological competence.

The following examples describe the conversion of bioactive polymer formulation (comprising a base polymer and a bioadditive) into filament feedstock which can be used with FFF-type or FDM-type 3D printers for medical device manufacture. That is, filament feedstock are created which are made of bioactive polymers comprising a copolymer of biological molecules (e.g., oligopeptide, collagen and/or sugar, oligosaccharides, hyaluronic acid) and a synthetic polymer. The filament feedstock to be fed into the printhead is made of bioactive polymers. A method of producing bioactive polymer filaments with bioadditive homogenously distributed throughout the base polymer matrix is also described.

Example 1: Base Polymers and Bioadditives

Fused filament fabrication (FFF) or fused deposition modelling (FDM) is a preferred manufacturing method due to its technological advantages. Advantageously, the filament extrusion process offers significant material blending that enables the use of developed bioactive polymers. The base polymer and bioadditive may be chosen depending on the biological and physical requirements of the desired application. The term "bioadditive" refers to a copolymer of synthetic polymer and biological molecule prepared by ring-opening metathesis polymerisation (ROMP). It is an acellular material which does not contain any live cells but is able to stimulate host cells to proliferate which promotes tissue growth. FIG. 31. below shows examples of different base polymers and bioadditives that may be used.

Base polymers can be various thermoplastic polymers or free radical polymers to be used with the bioadditive composition to produce the bioactive polymer disclosed herein. Examples of polymers are polyamide, poly(lactic-co-glycolic) acid, polycaprolactone, poly(lactic) acid, polyacrylate, polystyrene and polyurethane. Bioadditive is a copolymer of biological molecules and synthetic polymer prepared by ring-opening metathesis polymerisation (ROMP) method. Synthetic polymer herein may or may not be similar to that of the base polymer disclosed. Examples of biological molecules are collagen, oligopeptide, oligosaccharides, sugar and hyaluronic acid. In various embodiments, the method disclosed herein comprises incorporating at least one bioadditive composition with one base polymer into the monofilament required as the feedstock for FFF or FDM method of manufacturing.

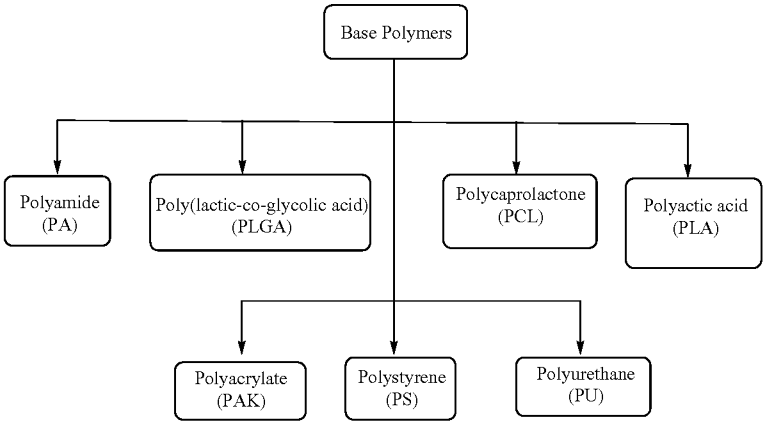

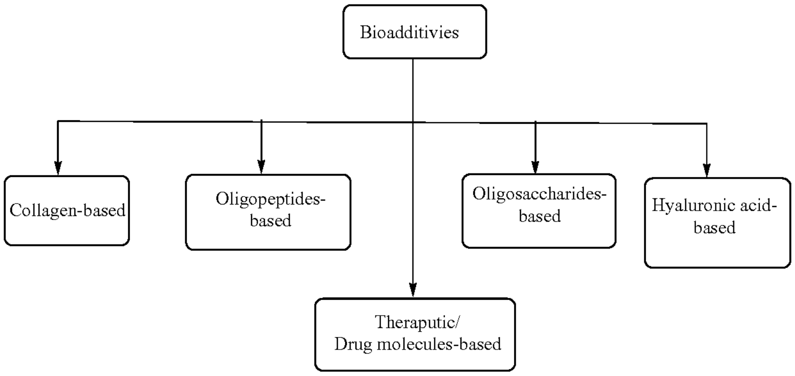

Example 2: Experimental Process Workflow

FIG. 32. shows the complete process workflow. Material preparation includes bioadditive synthesis, cryogenic grinding of base polymer, vacuum drying of materials and blending of bioadditive with base polymer.

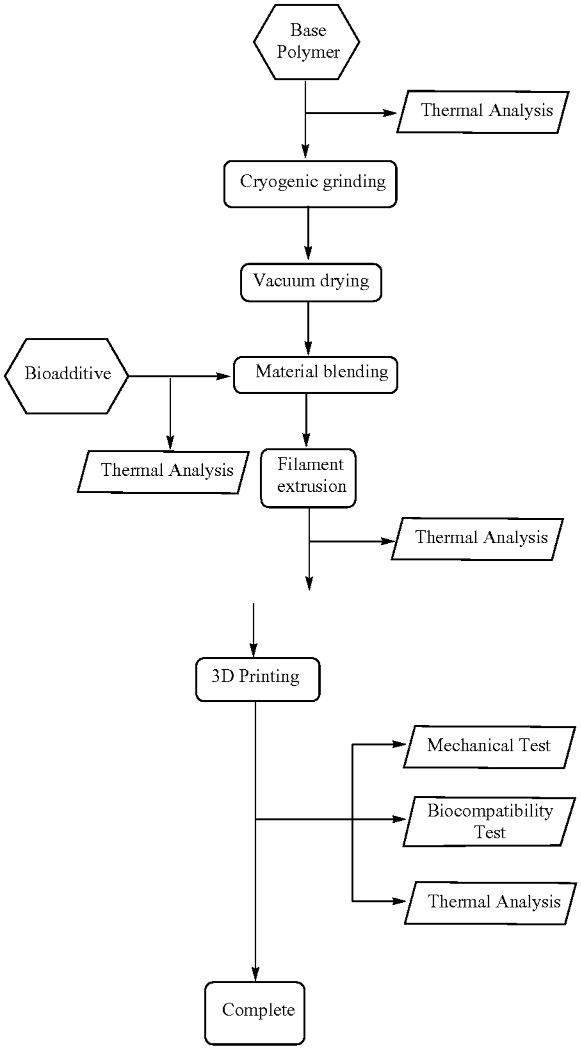

Bioactive polymer filament extrusion constitutes of cryogenic milling of base polymer pellets into powder form, vacuum drying of base polymer and bioadditive, blending of base polymer and bioadditive into a single formulation and filament extrusion of formulation into monofilaments.

Base polymer pellets were cryogenically grinded to powder form that is less than 1 mm in particle size using SPEX 6770 Freezer/Miller or SPEX 6875 Freezer/Miller. Each base polymer (e.g., polyamide-12 (PA12), poly(lactic acid) (PLA), poly(lactic-co-glycolic acid) (PLGA), poly(caprolactone) (PCL)) was subjected to different cryogenic grinding parameters as shown in Table 1. The vacuum drying parameters are shown in Table 2. Subsequently, the base polymer and bioadditive were mixed using ThinkyMixer ARE-250 or SPEX 8000D Mixer/Mill for at least 10 to 12 minutes and this mixture is referred to as the “formulation”.

Filament extrusion was performed using ThermoScientific Process 11 Twin-Screw Extruder (TSE) which comprises extruder, melt pump with a nozzle of Ø3 mm, water bath and haul unit. The filament extrusion parameters are shown in Table 3 and the filament extrusion result is shown in Table 4. Filament diameter needs to range between 2.5 mm to 3.1 mm as the FFF printer is configured for Ø2.85 mm filament. It is also able to manufacture filament suitable for FFF printer with Ø1.75 mm filament configuration.

In the following examples, simultaneous thermal analysis (STA) comprising thermogravimetric analysis (TGA) and differential scanning calorimetry (DSC) were carried out at different points to obtain the thermal properties of the bioadditive, bioactive polymer filament and 3D printed sheet. These results would provide necessary data required for filament extrusion and allow a side-by-side comparison of onset degradation of the materials after undergoing two high temperature processes, namely filament extrusion and 3D printing.

Mechanical tests were carried out according to American Society for Testing and Materials (ASTM) standards to determine the relevant mechanical properties of the materials tested.

Samples were also sent for biocompatibility tests with various human cell lines which the materials are designed to interact with.

TABLE 1

Cryogenic grinding parameters for base polymers

| Number of Cycles | Precool Time (min) | Cycle Duration (min) | Cool Time (min) | Impactor Speed (cycles/second) |
|---|---|---|---|---|
| PA12, PLA | | | | |
| 3 | 1 | 3 | 2 | 14 |
| PCL, PLGA | | | | |
| 2 | 1 | 3 | 2 | 14 |

TABLE 2

Vacuum drying parameters

| Material | Drying Temperature (°C) | Duration (Hrs) |
|---|---|---|
| PA12 | 80 | 8-12 |
| PA12 bioadditives | 45 | 8-12 |
| PCL | 40 | <12 |
| PCL bioadditives | 42.5 | <12 |
| PLA | 45 | <12 |
| PLA bioadditives | 45 | <12 |
| PLGA | 40 | <12 |
| PLGA bioadditives | 42.5 | <12 |

TABLE 3

| Filament extrusion parameters | | | | | | | | | | | | |
|---|---|---|---|---|---|---|---|---|---|---|---|---|
| Screw | Melt Pump | Feed | Heating | | | | | | | Die | Melt Pump | Spool |
| Speed (RPM) | Speed (RPM) | Rate (%) | Zone 2 (°C) | Zone 3 (°C) | Zone 4 (°C) | Zone 5 (°C) | Zone 6 (°C) | Zone 7 (°C) | Zone 8 (°C) | Temp. (°C) | Temp. (°C) | Speed (m/min) |
| Material(s): PA12, PA12-GPHP, PA12-PHPG/Cooling medium: Water | | | | | | | | | | | | |
| 105 | 5 | 14 | 180 | 200 | 210 | 220 | 240 | 240 | 230 | 230 | 220 | 0.4 |
| Material(s): PCL, PCL-GPHP, PCL-RGD/Cooling medium: Water | | | | | | | | | | | | |
| 275-360 | 4.8-5 | 18-25 | 40 | 60 | 70 | 80 | 90 | 100 | 100 | 95 | 85 | 0.4 |
| Material(s): PLA, PLA-GPHP, PLA-RGD, PLA-HA/Cooling medium: Air | | | | | | | | | | | | |
| 220-280 | 10-12 | 12 | 100-180 | 140-190 | 180-200 | 200-210 | 210-220 | 210-230 | 210-220 | 210-220 | 205-215 | 0.4 |
| Material(s): PLGA, PLGA-RGD, PLGA-HA/Cooling medium: Air | | | | | | | | | | | | |
| 220-260 | 4.5-4.7 | 11-15 | 60-100 | 100-140 | 120-180 | 140-190 | 160-200 | 180-200 | 180-190 | 170-180 | 160-170 | 0.4 |

Example 3: Polyamide (PA)-Based Bioactive Polymer Filament

3.1. Bioactive Polymer Filament (e.g., Produced from Polyamide (PA) and Collagen)

In this example, the collagen-like peptides used for synthesis were (Pro-Hyp-Gly)$_3$, abbreviated as PHPG, and (Gly-Pro-Hyp)$_3$, abbreviated as GPHP. Bioadditives synthesized are chemically similar and comprised poly(norbornene) dicarboximide brush polymers with polyamide-6 and poly(ethylene glycol)-collagen side chains which are referred to as PA6-PHPG and PA6-GPHP. The bioactive polymers produced by filament extrusion are referred to as PA12-PHPG and PA12-GPHP. Scheme 3 shows chemical structure of an example of PA6-[GPHyp]3 brush copolymer bio additive.

3.2. Simultaneous Thermal Analysis (STA

Figure 1:
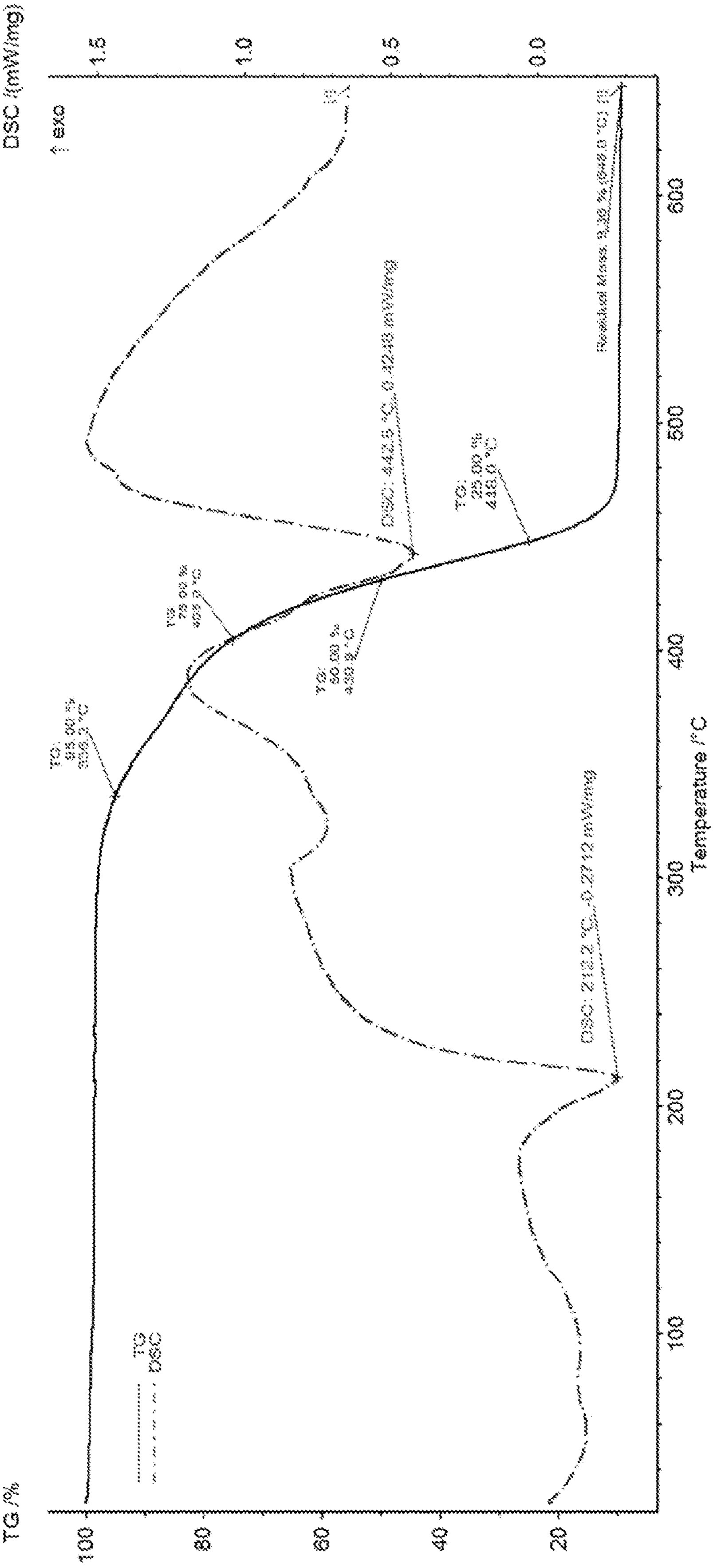
FIG. 1 shows simultaneous thermal analysis (STA) results of PA6-GPHP in accordance with various embodiments disclosed herein. In the figure, thermogravimetric analysis (TGA) graph is represented by solid line (see y-axis on the left) and differential scanning calorimetry (DSC) is represented by dashed line (see y-axis on the right). PA6 refers to polyamide-6 and GPHP refers to $(GPHyp)_3$.
Figure 2:
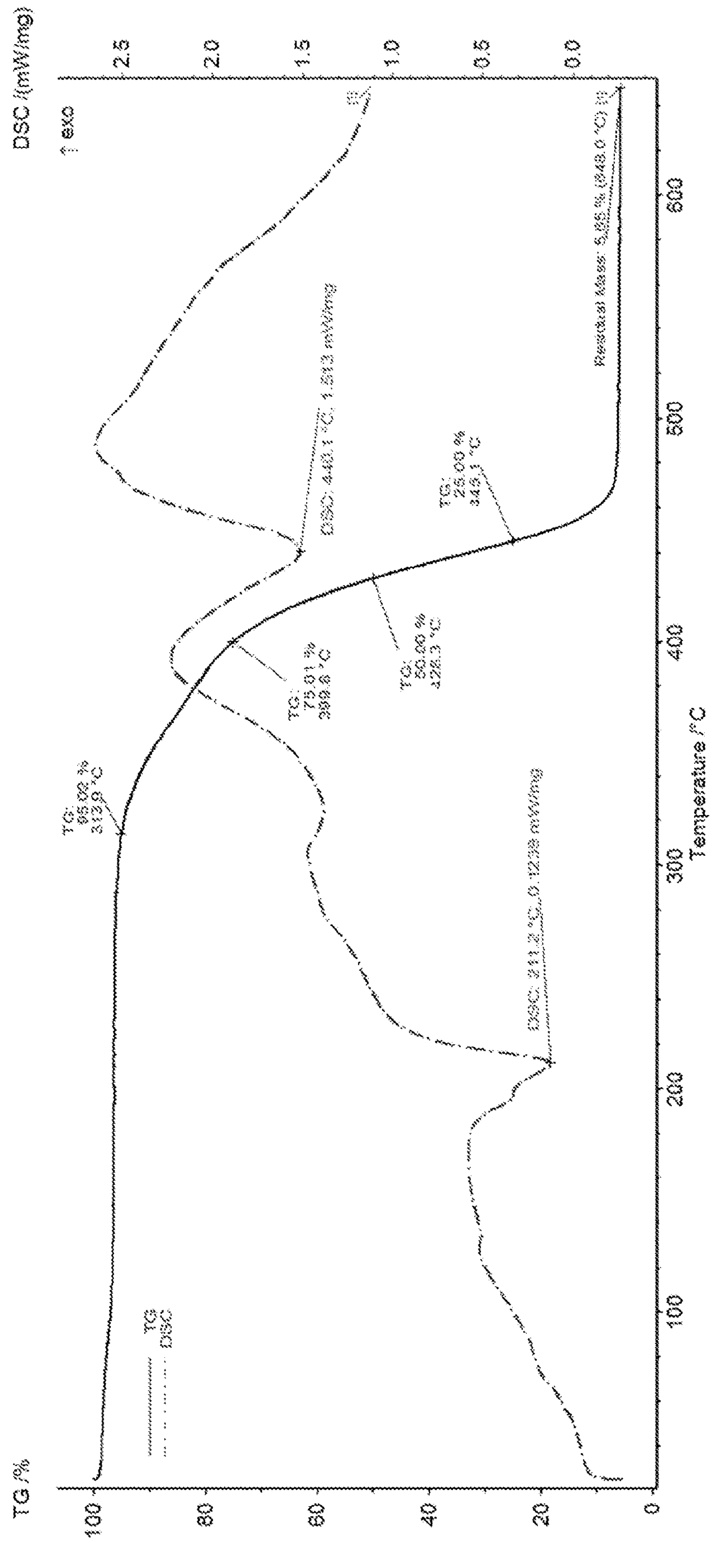
FIG. 2 shows simultaneous thermal analysis (STA) results of PA6-PHPG in accordance with various embodiments disclosed herein. In the figure, thermogravimetric analysis (TGA) graph is represented by solid line (see y-axis on the left) and differential scanning calorimetry (DSC) is represented by dashed line (see y-axis on the right). PA6 refers to polyamide-6 and PHPG refers to $(PHypG)_3$.

STA was carried out for each bioadditive component prior to filament extrusion. From FIG. 1 and FIG. 2, DSC graphs featured PA6-GPHP and PA6-PHPG melting at 213.2 °C and 211.5 °C respectively which are higher than the melting temperature of PA12 (180 °C). Without being bound by theory, it is believed that this was largely due to the presence of PA6 which is known to have higher melting temperature than PA12. TGA graphs of PA6-GPHP and PA6-PHPG highlights onset degradation temperatures of 336.5 °C and 313.9 °C respectively at 95% weight percentage. These results establish the working temperature range that should be adhered to. This facilitates in determining the suitable temperature profile to be used on twin screw extruder (TSE) for a good blending process during the filament extrusion of PA12-collagen.

Scheme 3

Chemical structure of PA6-[GPHyp]$_3$ brush copolymer bio additive

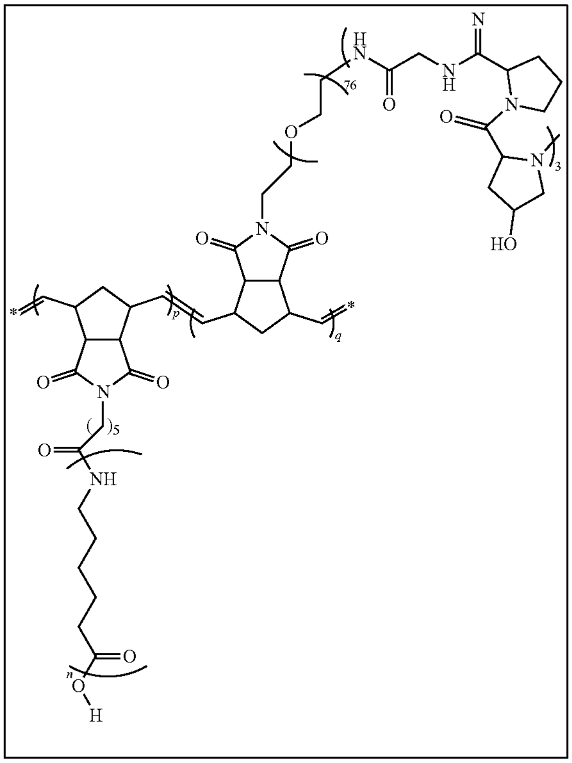

3.3. Filament Extrusion and PA12-Collagen Filament

Filament extrusion was carried out using the parameters as shown in Table 3. It was observed that thermoplastic polymers exhibit good melt viscosity when heated at 15 °C to 40 °C above the melting temperature which enables good material flow for filament extrusion. Melt pump temperature of 220 °C was specifically used as the molten extrudate to allow more time for it to be manipulated into the water bath, measuring unit and haul unit for spooling process to occur.

In addition to the above, a desired filament diameter can be achieved by adjusting the speed-based parameters such as screw speed, melt pump and spool speed. Molten extrudate which has cooled down is then referred to as the "filament".

Figure 3:
FIG. 3 shows a photograph taken for a PA12-collagen filament in accordance with various embodiments disclosed herein. Bioactive polymer: PA6-collagen; additive content: 10%; and filament diameter: 2.85±0.1 mm.

FIG. 3 shows a photograph of the obtained PA12-collagen filaments, which appeared to be in a translucent tangerine colour.

3.4. Thermogravimetric Analysis (TGA)

Figure 4:
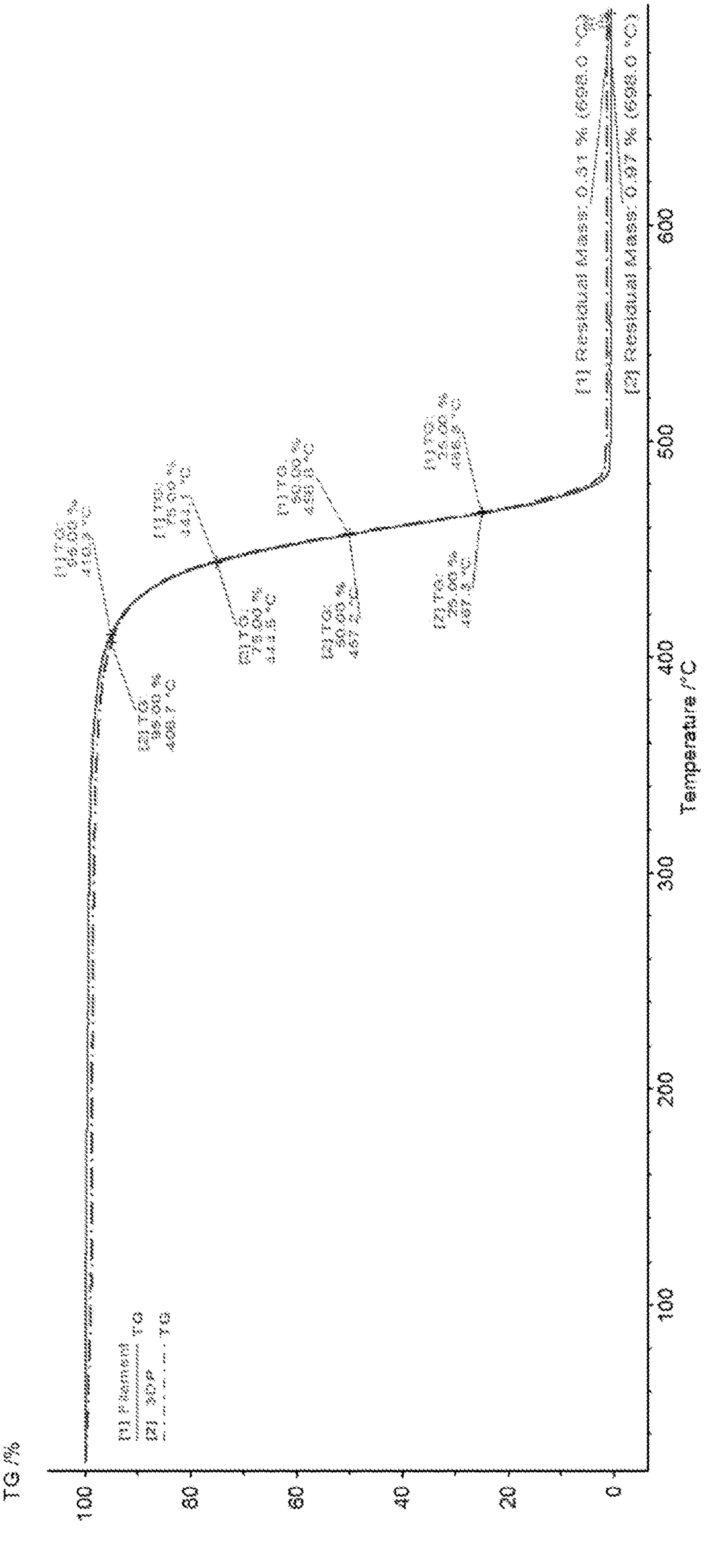
FIG. 4 shows thermogravimetric analysis (TGA) results of PA12-PHPG samples of 3D printed sheet and its filament in accordance with various embodiments disclosed herein. In the figure, PA12-PHPG 3DP sheet is represented by graph [2]; dashed line and its filament is represented by graph [1]; solid line. PA12 refers to polyamide-12 and PHPG refers to $(PHypG)_3$.
Figure 5:
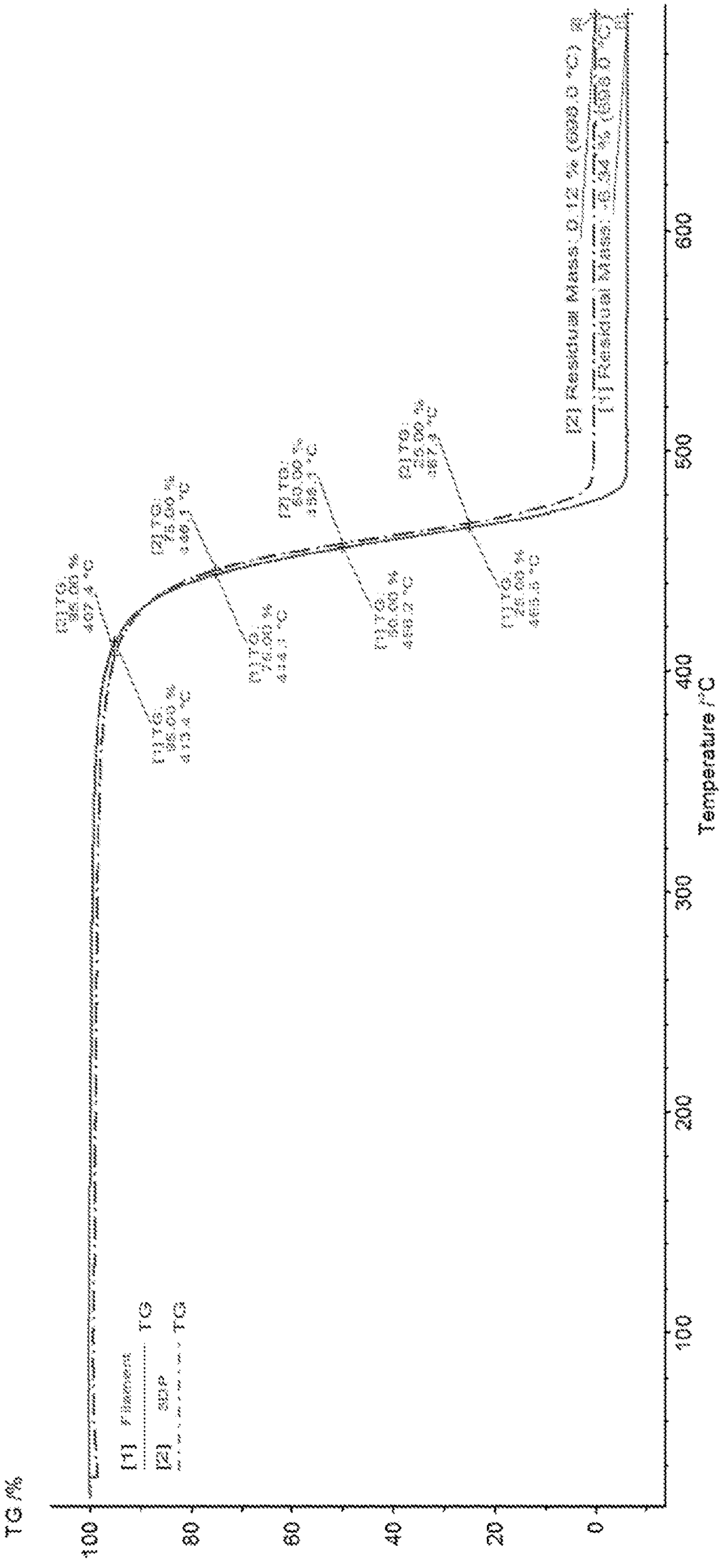
FIG. 5 shows thermogravimetric analysis (TGA) results of PA12-GPHP samples of 3D printed sheet and its filament in accordance with various embodiments disclosed herein. In the figure, PA12-GPHP 3DP sheet is represented by graph [2]; dashed line and its filament is represented by graph [1]; solid line. PA12 refers to polyamide-12 and GPHP refers to $(GPHyp)_3$.

FIG. 4 shows two graphs stacked together, featuring PA12-PHPG samples of 3D printed sheet (dashed line) and its filament (solid line) while FIG. shows two graphs stacked together, featuring PA12-GPHP samples of 3D printed sheet and filament. It was observed that PA12-PHPG filament and 3D printed samples have similar thermal degradation profile whereby the difference in degradation temperature at various weight percentages ranged between 0.09 to 0.8% only. Similarly, PA12-GPHP exhibited similar thermal degradation profile for filament and 3D printed samples whereby the difference in degradation temperature at various weight percentages ranged between 0.4 to 1.5%. This finding substantiates the thermal stability of the bioactive copolymers tested and shows that the biological molecule is not lost after filament extrusion and 3D printing.

3.5. Mechanical Properties

Figure 6:
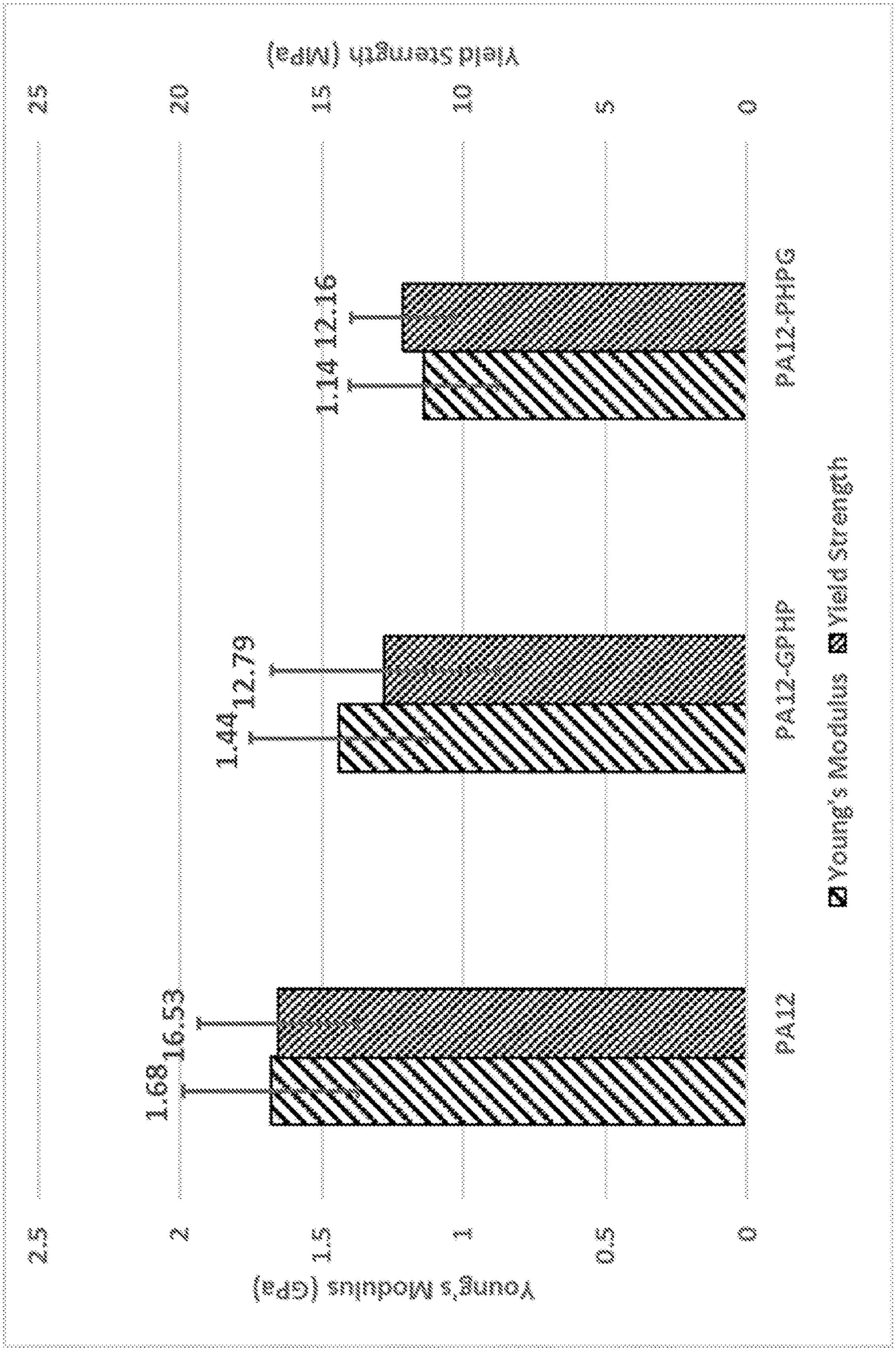
FIG. 6 is a graph showing Young's modulus (on the left axis) and yield strength (on the right axis) of PA12-based specimens, namely PA12-PHPG and PA12-GPHP in accordance with various embodiments disclosed herein.

Mechanical test was carried out to determine the tensile properties of the materials according to ASTM D638 (Standard Test Method for Tensile Properties of Plastics). The test specimens were dimensioned to the specifications of Type V specimen. Results from the test are compiled and shown in the bar graphs in FIG. 6.

It can be observed that the Young's modulus and yield strength of PA12-PHPG and PA12-GPHP were reduced as compared to pure PA12 which implies that the addition of the bioadditive resulted in those reduction. This was due to the pegylated peptide in the bioactive polymers as the biological molecules are amorphous with no significant mechanical advantage which compromises the tensile test results.

From the Young's modulus result, PA12 has an average of 1.68 GPa while PA12-GPHP and PA12-PHPG have an average of 1.44 GPa and 1.14 GPa, which translate to a reduction of 14.3% and 32.1% respectively.

From the yield strength result, PA12 has an average of 16.53 MPa while PA12-GPHP and PA12-PHPG have an average of 12.79 MPa and 12.16 MPa, which translate to a yield strength reduction of 22.6% and 26.4% respectively.

It was observed that the specimens did not fracture cleanly as a whole because some layers of the specimens fractured earlier than others and this was observed in all of the materials tested. However, PA12 test specimens displayed less of this phenomenon as compared to PA12-PHPG and this was largely due the nature of FFF method of manufacturing. In addition, two of the PA12-PHPG specimens also exhibited premature layer delamination during the test which could have compromised the mechanical properties to a certain degree. This was due to a printing issue known as under-extrusion whereby very little material was extruded which created gaps between the infill lines and inconsistent layer height.

3.6. Biocompatibility Tests

Figure 7:
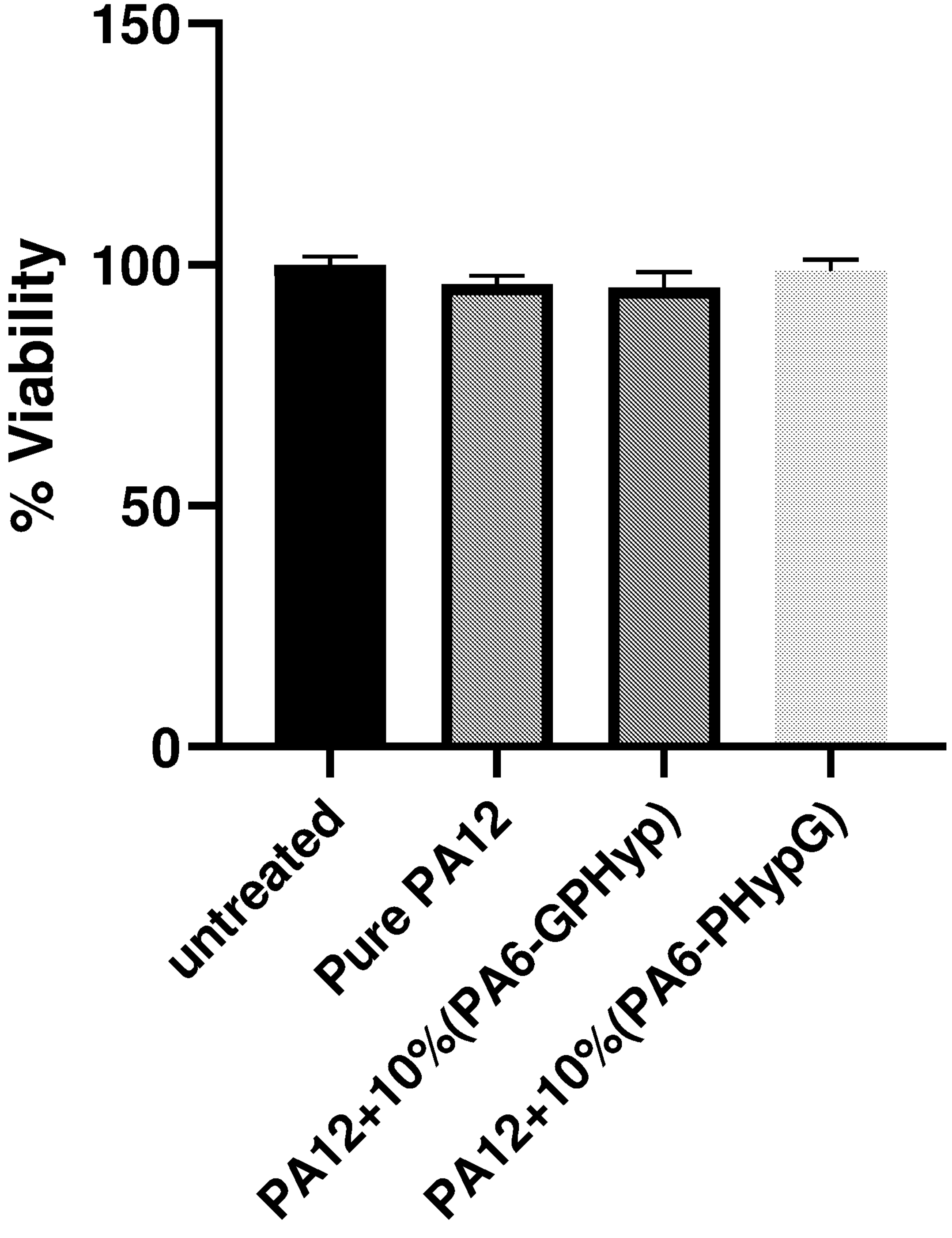
FIG. 7 is a graph showing biocompatibility test results (i.e. % cell viability count) of sheet samples, namely (1) untreated sample; (2) pure PA12 sheet; (3) PA12+10% PA6-GPHyp; and (4) PA12+10% PA6-PHypG in accordance with various embodiments disclosed herein. The untreated sample acts as a control.

Biocompatibility test was performed using cell viability test assays with human fibroblasts Hs27 on 3D printed sheet samples. The result indicates that each of the bioactive material tested was biocompatible in comparison to untreated and virgin PA12 groups, as shown in FIG. 7.

Example 4: Polycaprolactone (PCL)-Based Bioactive Polymer Filament

Figure 8:
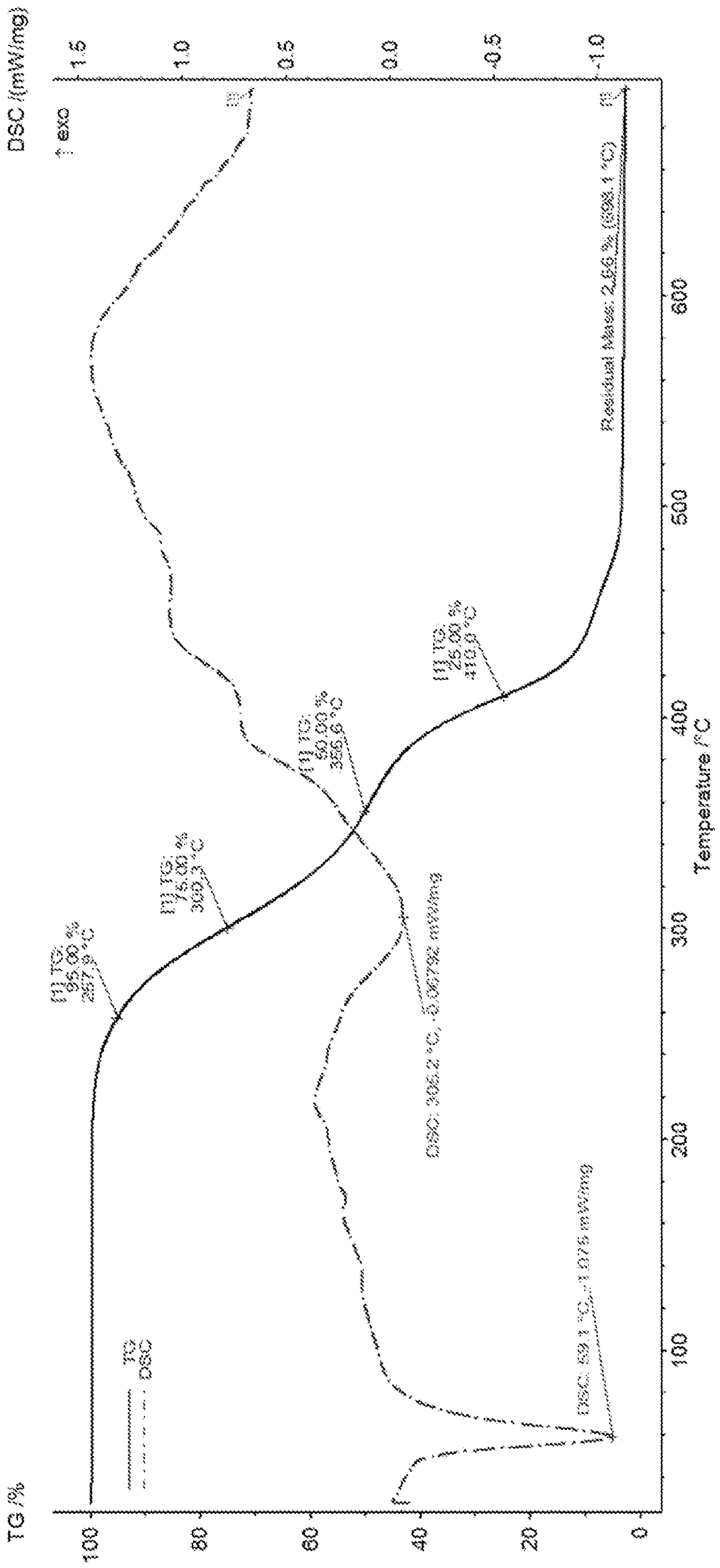
FIG. 8 shows simultaneous thermal analysis (STA) results of PCL-GPHP in accordance with various embodiments disclosed herein. In the figure, thermogravimetric analysis (TGA) graph is represented by solid line (see y-axis on the left) and differential scanning calorimetry (DSC) is represented by dashed line (see y-axis on the right). PCL refers to poly(caprolactone) and GPHP refers to $(GPHyp)_3$.
Figure 9:
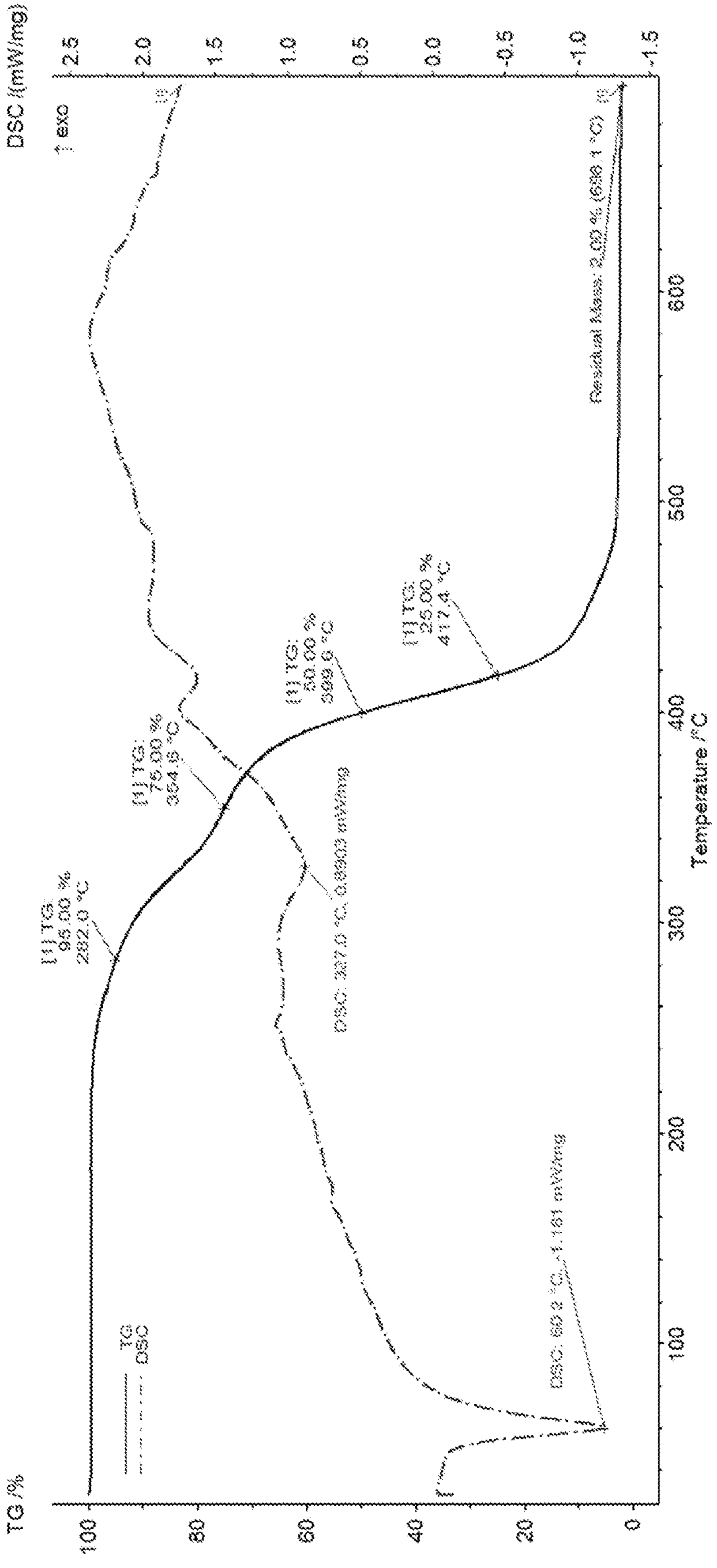
FIG. 9 shows simultaneous thermal analysis (STA) results of PCL-RGD in accordance with various embodiments disclosed herein. In the figure, thermogravimetric analysis (TGA) graph is represented by solid line (see y-axis on the left) and differential scanning calorimetry (DSC) is represented by dashed line (see y-axis on the right). PCL refers to poly(caprolactone) and RGD refers to arginine-glycine-aspartic acid.
Figure 10:
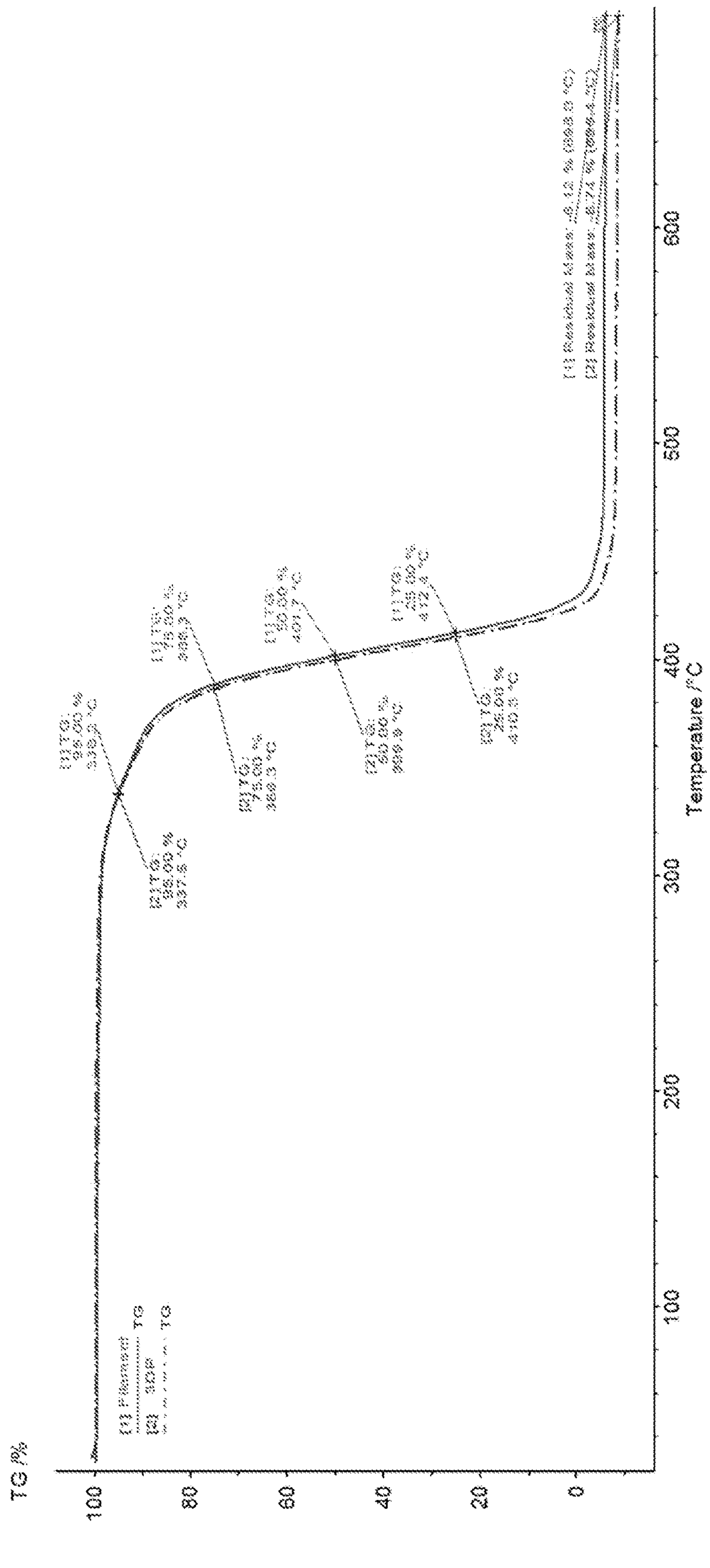
FIG. 10 shows thermogravimetric analysis (TGA) results of PCL-GPHP samples of 3D printed sheet and its filament in accordance with various embodiments disclosed herein. In the figure, PCL-GPHP 3DP sheet is represented by graph [2]; dashed line and its filament is represented by graph [1]; solid line. PCL refers to poly(caprolactone) and GPHP refers to $(GPHyp)_3$.

In this example, simultaneous thermal analysis (STA) consisting of thermogravimetric (TGA) and differential scanning calorimeter (DSC) analyses were performed on PCL-based bioadditives and bioactive PCLs after extrusion and 3D printing (3DP) processes. From FIG. 8 and FIG. 9, it can be derived that bioadditives, PCL-GPHP and PCL-RGD, melted between 59 °C to 60 °C while onset degradation occurred at 257.9 °C and 282 °C respectively at weight percentage of 95%. These results enabled for process optimization of extrusion and 3DP processes whereby processing temperatures should be between 90 °C to 240 °C ensuring good melt flow. The parameters used for filament extrusion process are shown in Table 3 above. Additionally, FIG. 10 shows the thermographs of bioactive PCL, PCL-GPHP, after filament extrusion and 3DP processes. It can be seen that the degradation at various weight percentages were similar with a difference ranging between 0.2 to 0.5%. This exhibits the thermal stability of the bioadditive where there was no loss of biological molecule after two high heat processes.

Example 5: Poly(Lactic Acid) (PLA)-Based Bioactive Polymer Filament

In this example, simultaneous thermal analysis (STA) consisting of thermogravimetric (TGA) and differential scanning calorimeter (DSC) analyses were performed on PLA-based bioadditives.

Figure 11:
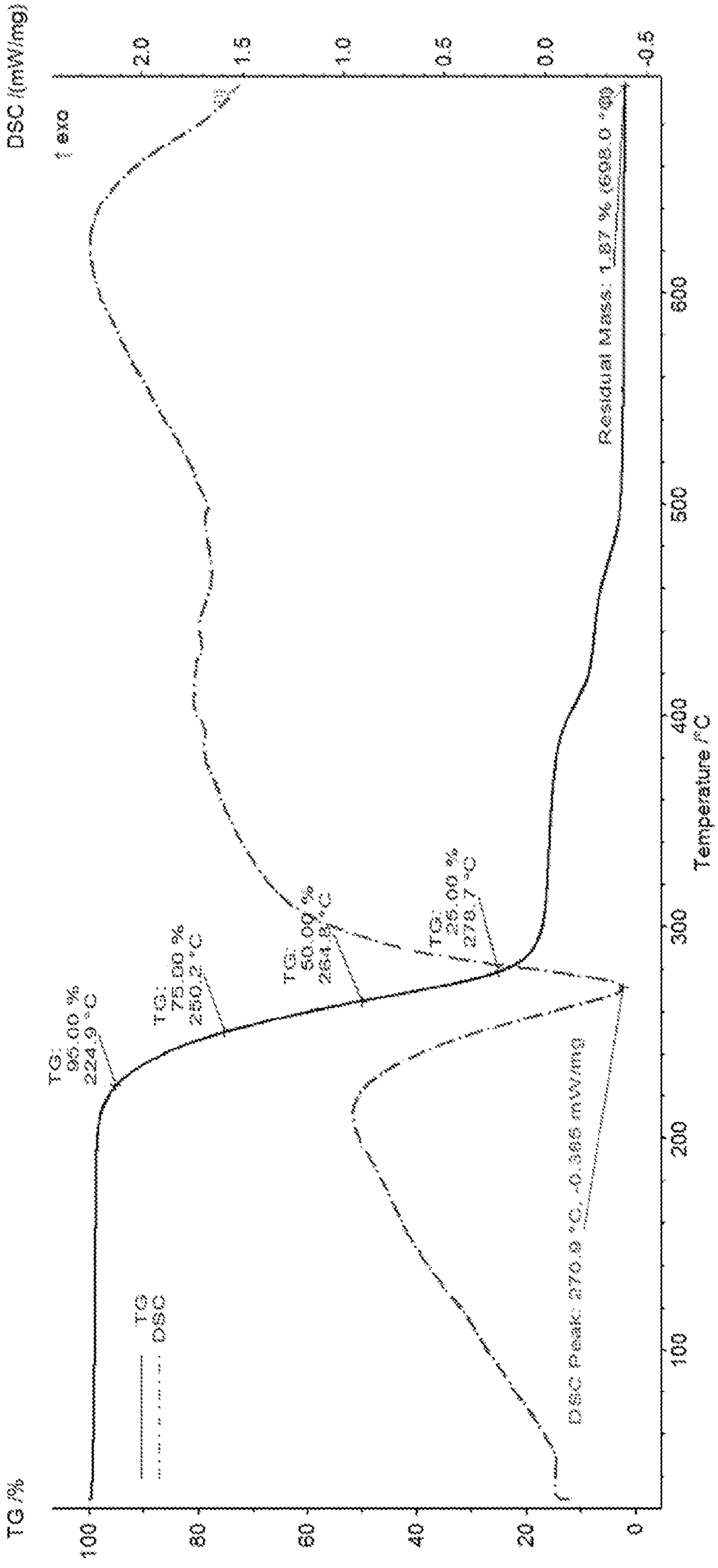
FIG. 11 shows simultaneous thermal analysis (STA) results of PLA-GPHP in accordance with various embodiments disclosed herein. In the figure, thermogravimetric analysis (TGA) graph is represented by solid line (see y-axis on the left) and differential scanning calorimetry (DSC) is represented by dashed line (see y-axis on the right). PLA refers to poly(lactic acid) and GPHP refers to $(GPHyp)_3$.
Figure 12:
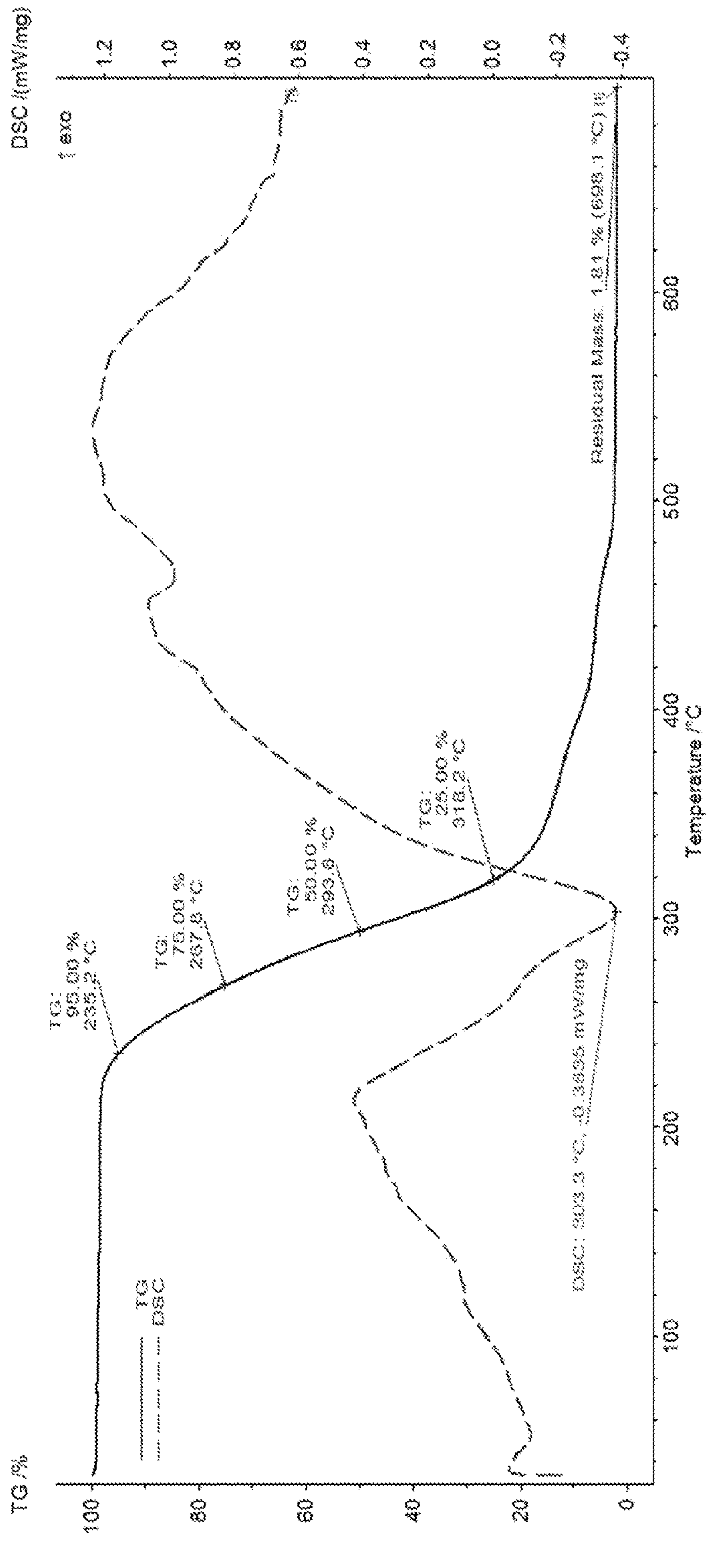
FIG. 12 shows simultaneous thermal analysis (STA) results of PLA-RGD in accordance with various embodiments disclosed herein. In the figure, thermogravimetric analysis (TGA) graph is represented by solid line (see y-axis on the left) and differential scanning calorimetry (DSC) is represented by dashed line (see y-axis on the right). PLA refers to poly(lactic acid) and RGD refers to arginine-glycine-aspartic acid.
Figure 13:
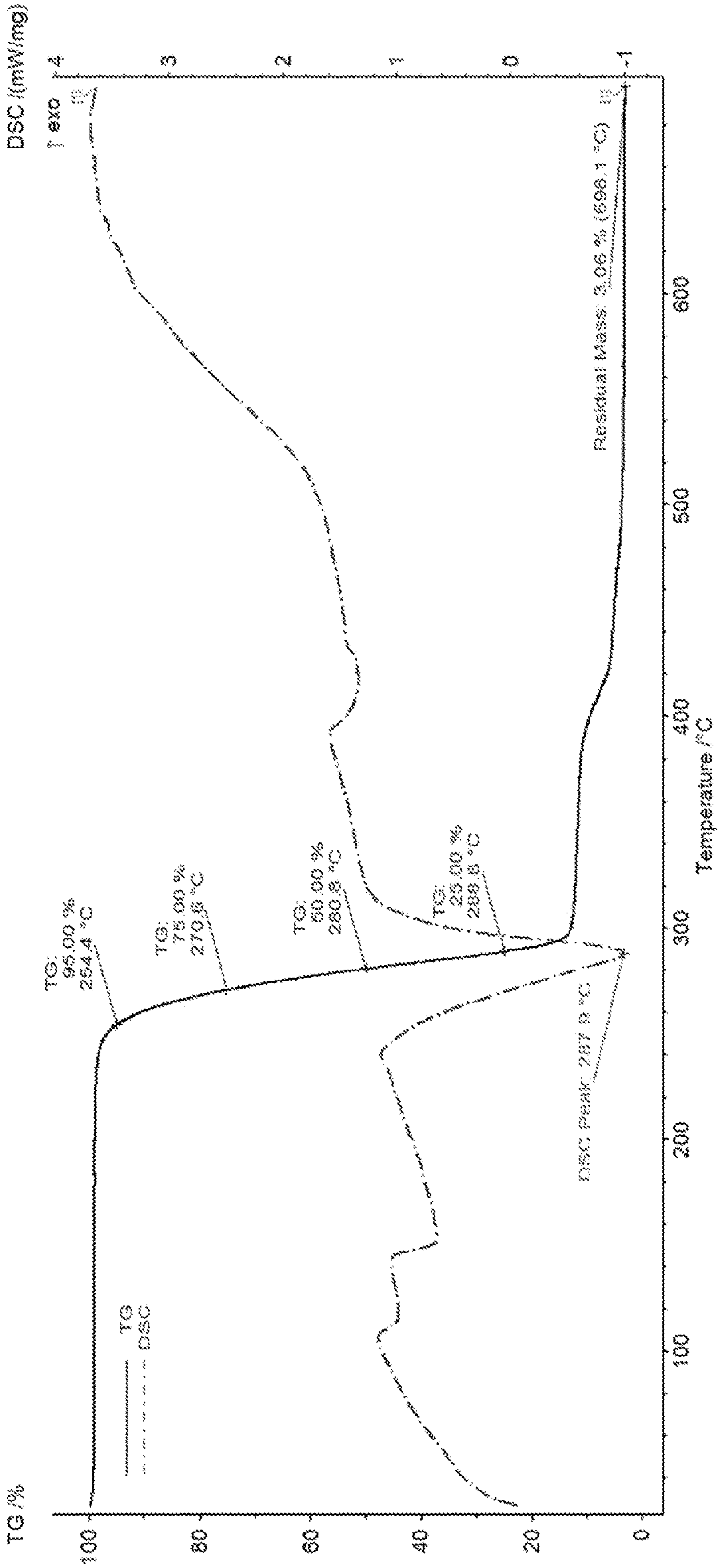
FIG. 13 shows simultaneous thermal analysis (STA) results of PLA-HA in accordance with various embodiments disclosed herein. In the figure, thermogravimetric analysis (TGA) graph is represented by solid line (see y-axis on the left) and differential scanning calorimetry (DSC) is represented by dashed line (see y-axis on the right). PLA refers to poly(lactic acid) and HA refers to hyaluronic acid.
Figure 14:
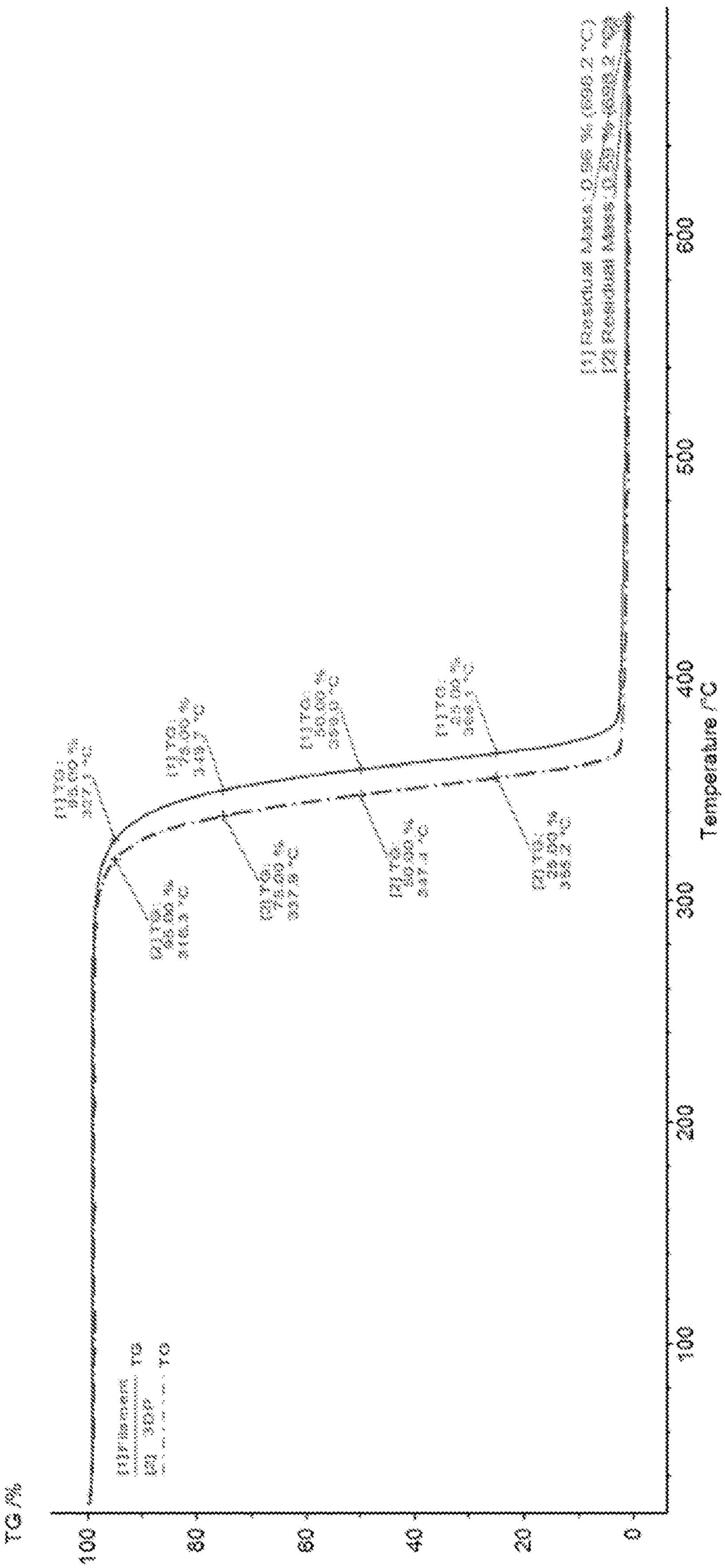
FIG. 14 shows thermogravimetric analysis (TGA) results of PLA-GPHP samples of 3D printed sheet and its filament in accordance with various embodiments disclosed herein. In the figure, PLA-GPHP 3DP sheet is represented by graph [2]; dashed line and its filament is represented by graph [1]; solid line. PLA refers to poly(lactic acid) and GPHP refers to $(GPHyp)_3$.

FIG. 11, FIG. 12 and FIG. 13 respectively show the STA graphs of PLA-based bioadditives, namely PLA-GPHP, PLA-RGD and PLA-HA whereby no specific melting points were identified which corresponded to an amorphous structure of the bioadditives. Onset degradation of the bioadditives occurred between 224 °C to 254 °C at 95% weight percentage. PLA-HA attained the highest temperature resisting thermal degradation due to the longer chain length of hyaluronic acid as compared to peptide and collagen. However, pure semi-crystalline PLA used as the base polymer exhibited a melting point of 190 °C, resulting in a narrow processing temperature range, namely 190 °C to 220 °C for PLA-GPHP & PLA-RGD and 190 °C to 250 °C for PLA-HA. Table 3 shows the parameters used for filament extrusion process. From FIG. 14, TGA thermographs of PLA-GPHP filament and 3D printed samples exhibited similar degradation points at different weight percentages with the difference ranging between 2.7% to 3.5%. This shows the thermal stability of the bioadditive whereby no biological molecule was lost after undergoing extrusion and 3DP processes at elevated temperatures.

Example 6: Poly(Lactic-Co-Glycolic Acid) (PLGA)-Based Bioactive Polymer Filament In this example, simultaneous thermal analysis (STA) consisting of thermogravimetric (TGA) and differential scanning calorimeter (DSC) analyses were performed on PLGA-based bioadditives.

Figure 15:
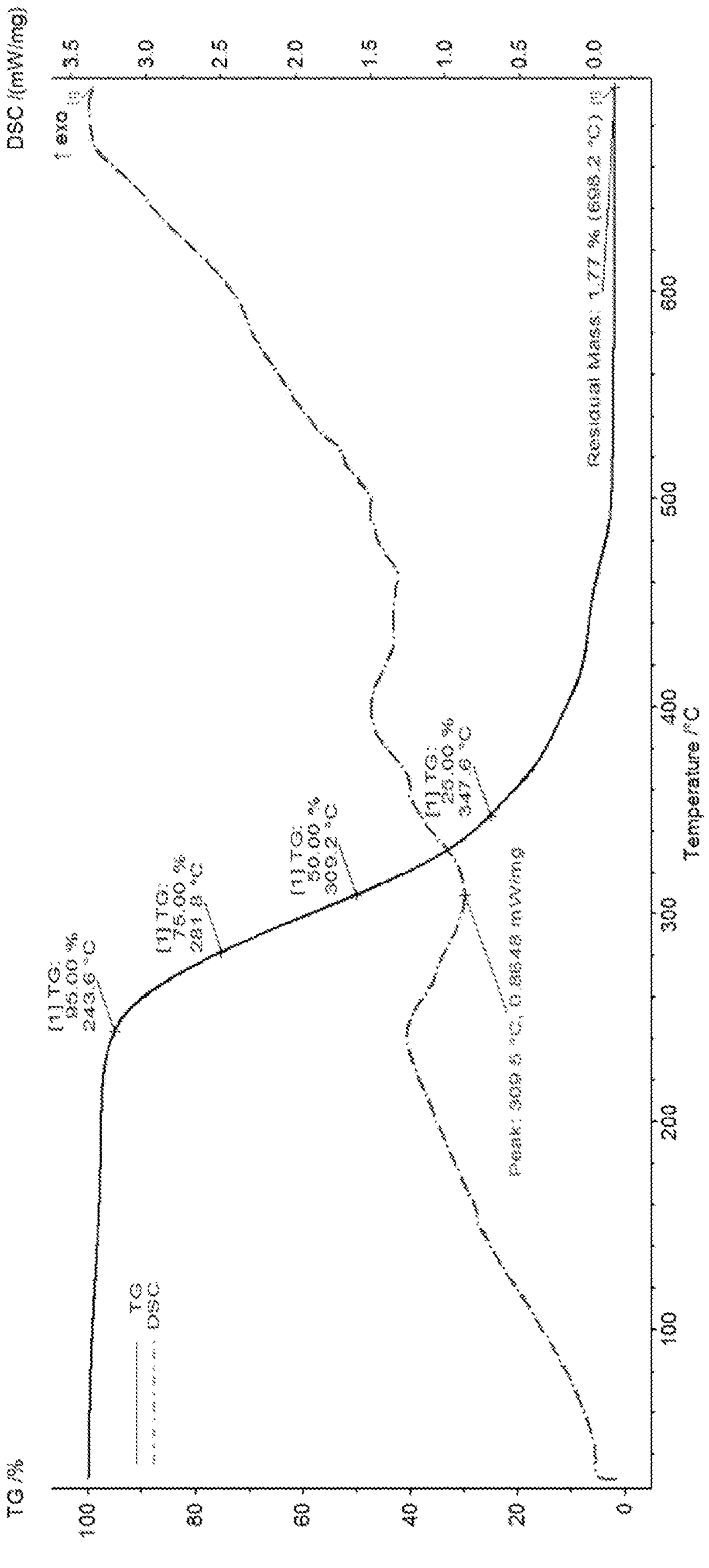
FIG. 15 shows simultaneous thermal analysis (STA) results of PLGA-GPHP in accordance with various embodiments disclosed herein. In the figure, thermogravimetric analysis (TGA) graph is represented by solid line (see y-axis on the left) and differential scanning calorimetry (DSC) is represented by dashed line (see y-axis on the right). PLGA refers to poly(lactic-co-glycolic acid) and GPHP refers to $(GPHyp)_3$.
Figure 16:
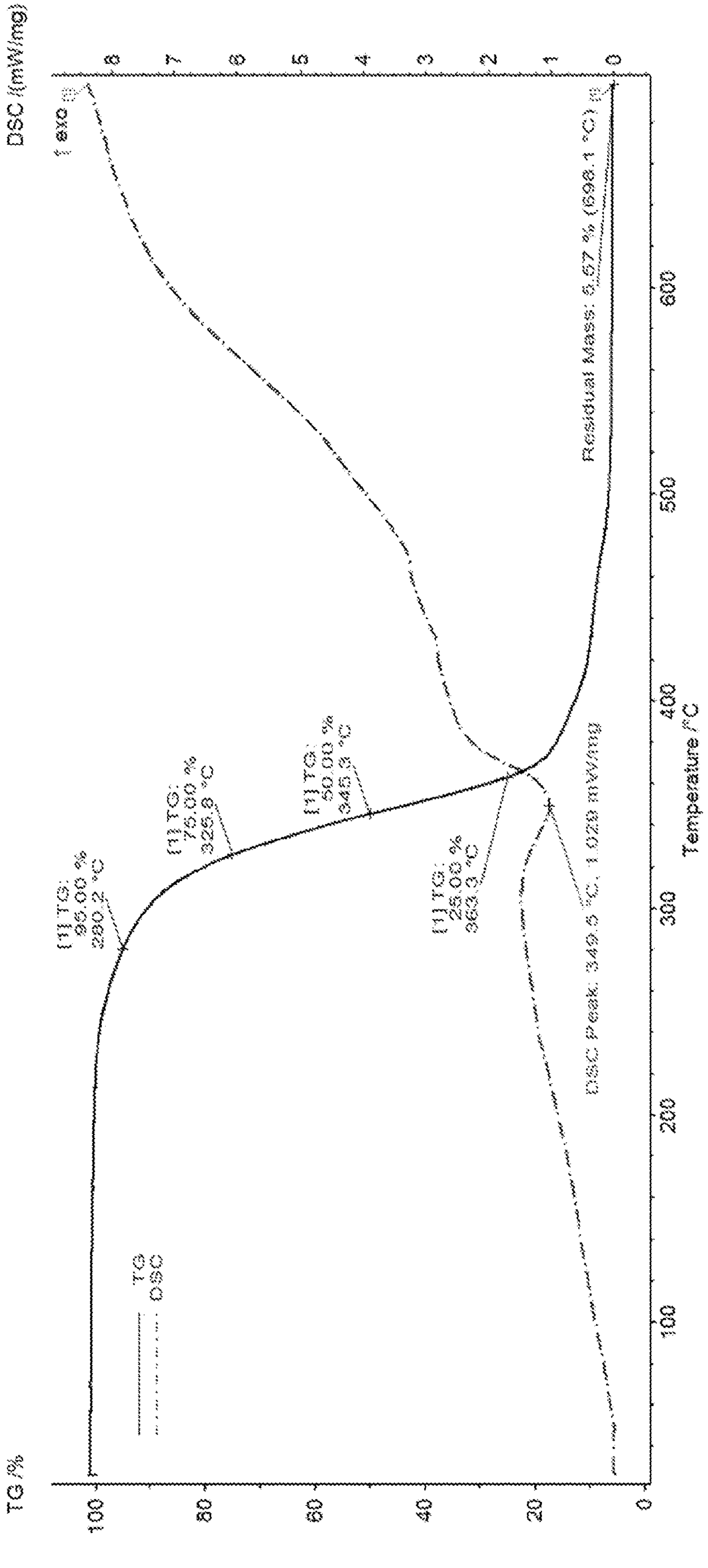
FIG. 16 shows simultaneous thermal analysis (STA) results of PLGA-RGD in accordance with various embodiments disclosed herein. In the figure, thermogravimetric analysis (TGA) graph is represented by solid line (see y-axis on the left) and differential scanning calorimetry (DSC) is represented by dashed line (see y-axis on the right). PLGA refers to poly(lactic-co-glycolic acid) and RGD refers to arginine-glycine-aspartic acid.
Figure 17:
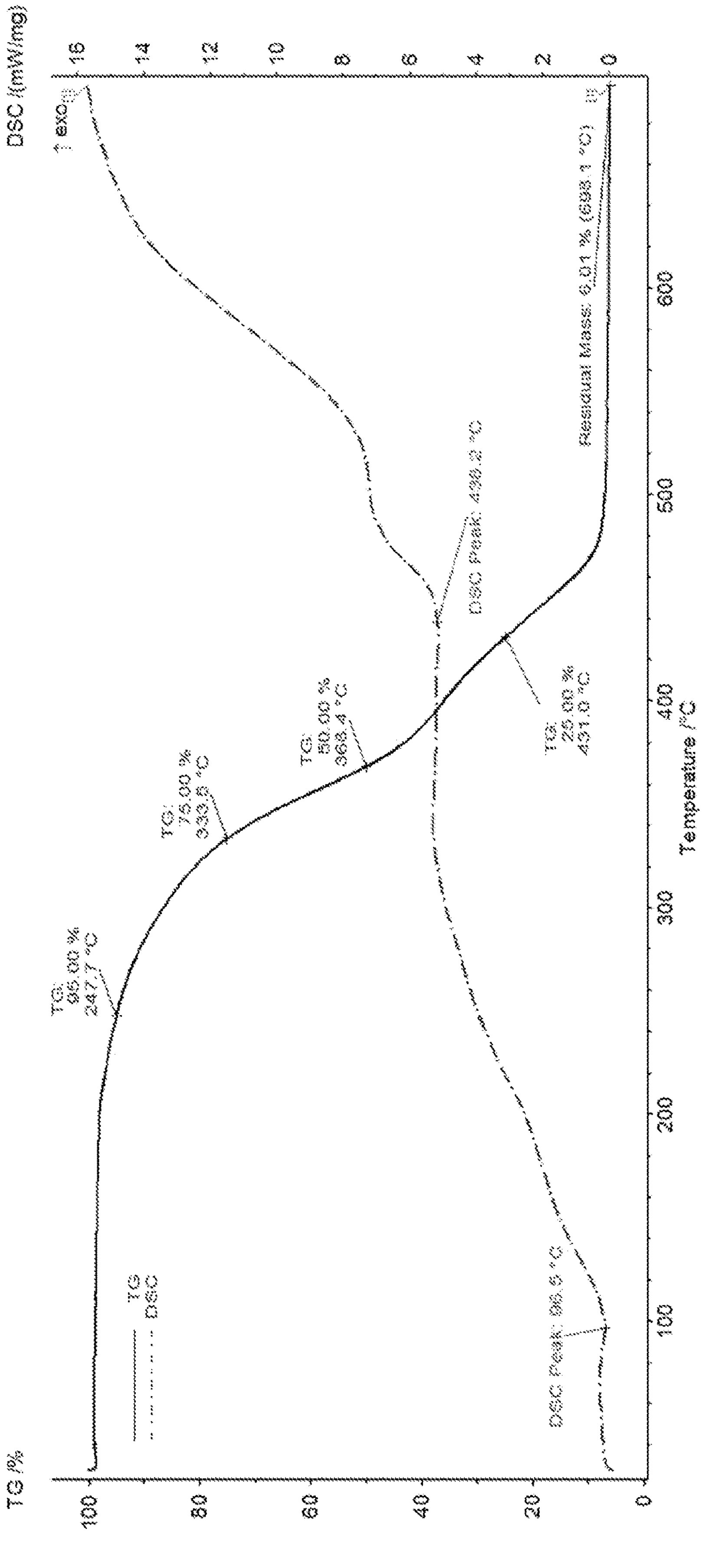
FIG. 17 shows simultaneous thermal analysis (STA) results of PLGA-HA in accordance with various embodiments disclosed herein. In the figure, thermogravimetric analysis (TGA) graph is represented by solid line (see y-axis on the left) and differential scanning calorimetry (DSC) is represented by dashed line (see y-axis on the right). PLGA refers to poly(lactic-co-glycolic acid) and HA refers to hyaluronic acid.
Figure 18:
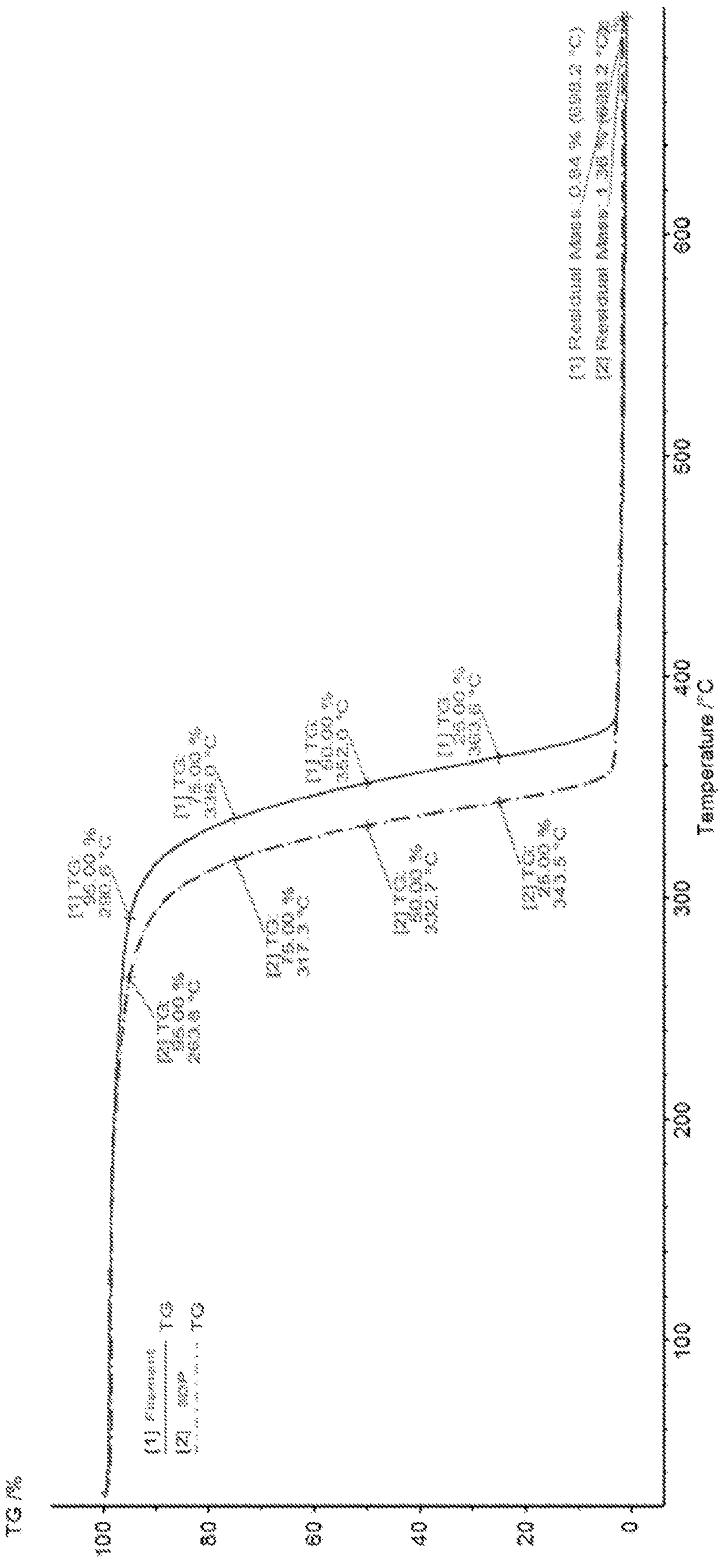
FIG. 18 shows thermogravimetric analysis (TGA) results of PLGA-HA samples of 3D printed sheet and its filament in accordance with various embodiments disclosed herein. In the figure, PLGA-HA 3DP sheet is represented by graph [2]; dashed line and its filament is represented by graph [1]; solid line. PLGA refers to poly(lactic-co-glycolic acid) and HA refers to hyaluronic acid.

As shown in FIG. 15, FIG. 16 and FIG. 17, the melting point and onset degradation of PLGA bioadditives were established by STA. Melting points of PLGA-GPHP, PLGA-RGD and PLGA-HA were not clearly identified and this highlighted the amorphous nature of the bioadditives' crystal structure. This is also similar to the pure PLGA used as the base polymer. Nevertheless, the onset degradation of these bioadditives ranged between 243 °C to 281 °C while pure PLGA degrades at 309 °C. Table 3 shows the parameters used for filament extrusion process. In addition, FIG. 18 shows the TGA thermographs comparing the degradation points at different weight percentages of PLGA-HA filament and 3DP samples. The difference of degradation points between two samples ranged between 5 to 10% only.

Example 7: Biocompatibility Test of PLGA-Based and PLA-Based Materials

Figure 19:
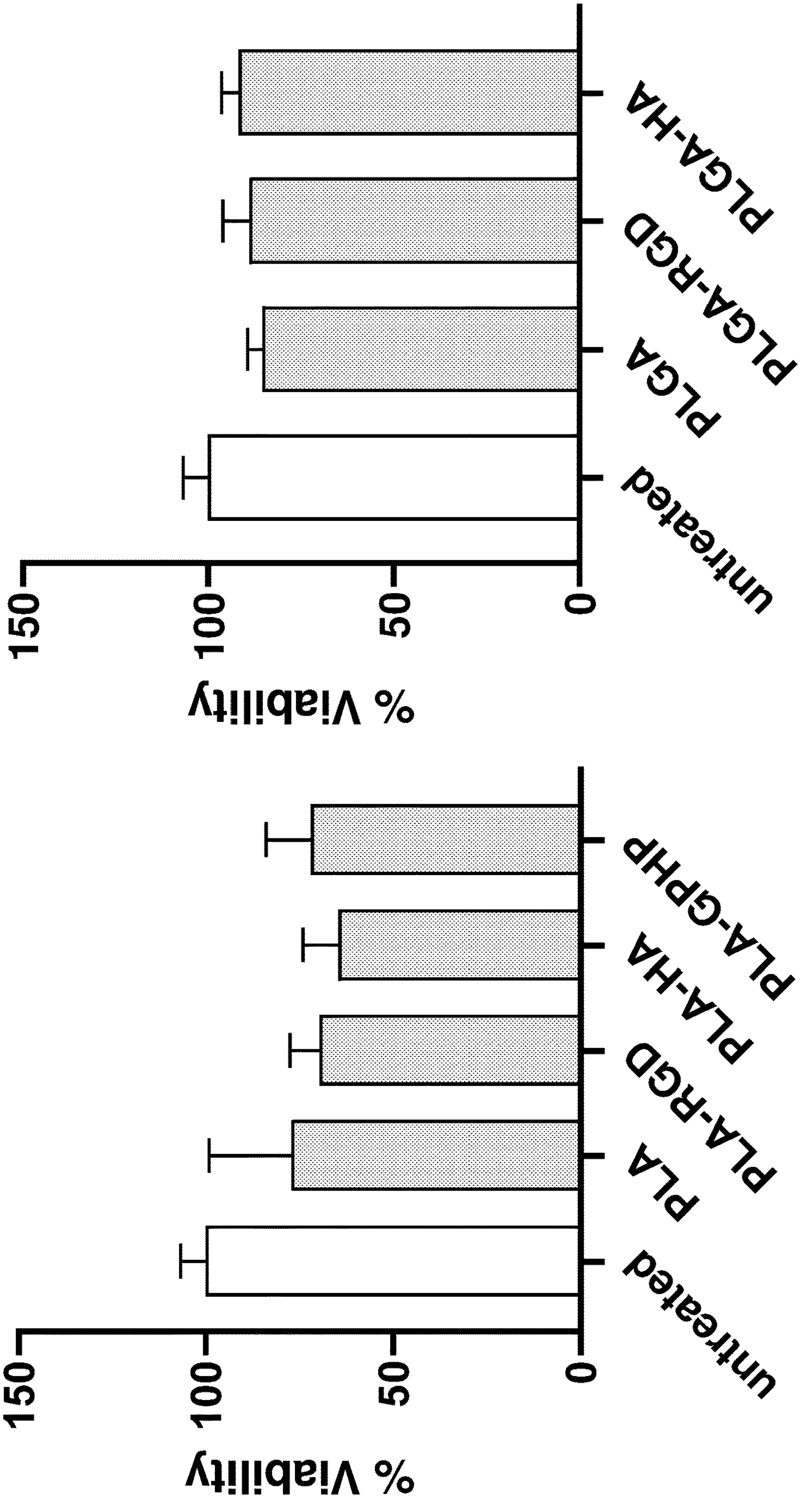
FIG. 19 is a graph showing biocompatibility test results (i.e. % cell viability count) of sheet samples, namely (1) untreated sample; (2) pure PLGA sheet; (3) PLGA-RGD; (4) PLGA-HA; (5) untreated sample; (6) pure PLA sheet; (7) PLA-RGD; (8) PLA-HA; and (9) PLA-GPHP in accordance with various embodiments disclosed herein. The untreated sample acts as a control.
Figure 20A:
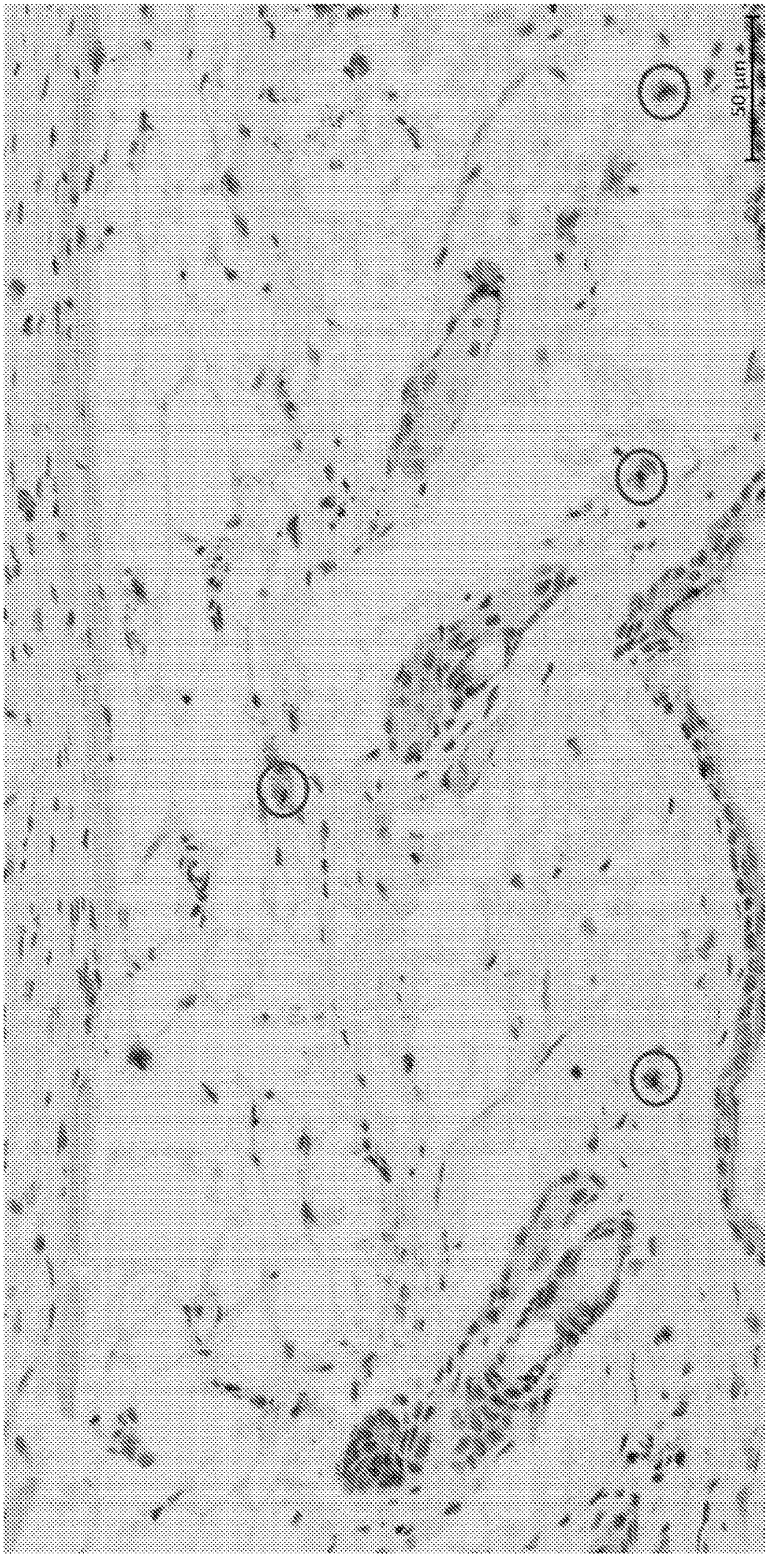
FIG. 20A shows an image obtained from immunohistochemistry (IHC) staining for $CD3^+$ cells, with cell nuclei (dark coloured spots) and CD3 (representatively circled) differentially labelled. Pathological assessment reports 2+ for negative control. Image shown is representative with at least 4 C57BL/6 mice per group. Scale bar=50 μm.
Figure 20B:
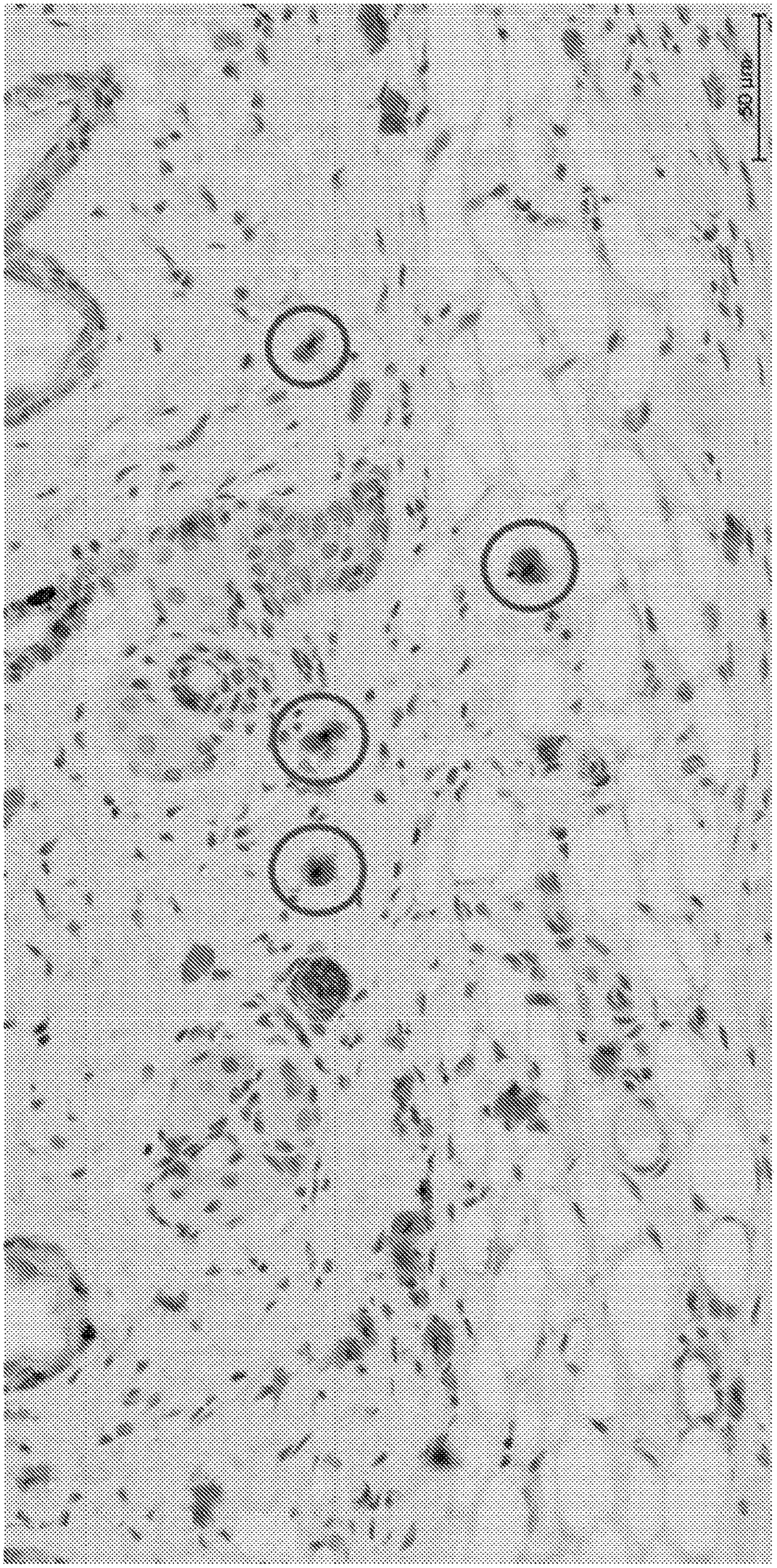
FIG. 20B shows an image obtained from immunohistochemistry (IHC) staining for $CD3^+$ cells, with cell nuclei (dark coloured spots) and CD3 (representatively circled) differentially labelled. Pathological assessment reports 3+ for PA12. Image shown is representative with at least 4 C57BL/6 mice per group. Scale bar=50 μm.
Figure 20C:
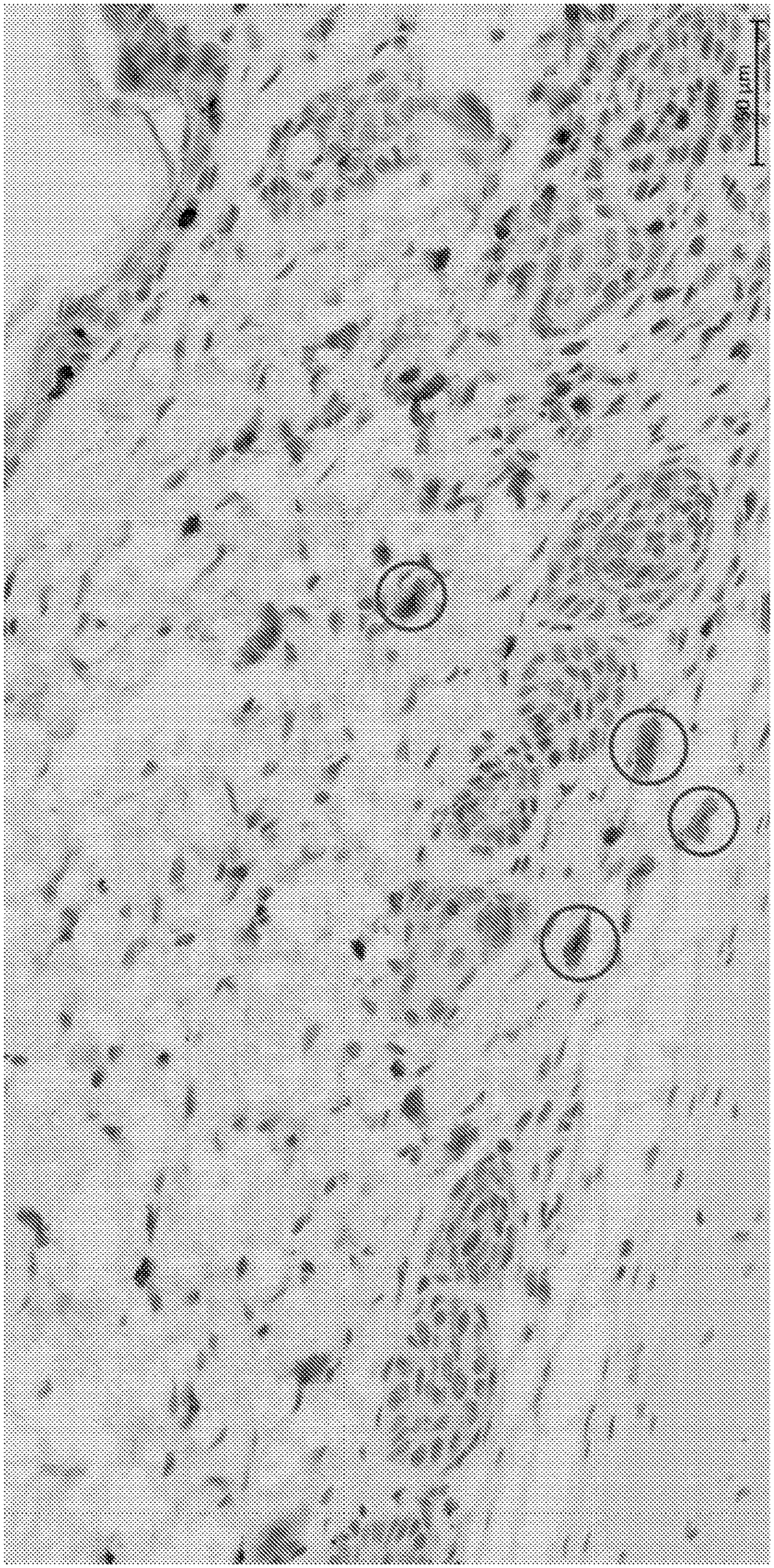
FIG. 20C shows an image obtained from immunohistochemistry (IHC) staining for $CD3^+$ cells, with cell nuclei (dark coloured spots) and CD3 (representatively circled) differentially labelled. Pathological assessment reports 3+ for PA12-(PA6-GPHP). Image shown is representative with at least 4 C57BL/6 mice per group. Scale bar=50 μm.
Figure 21A:
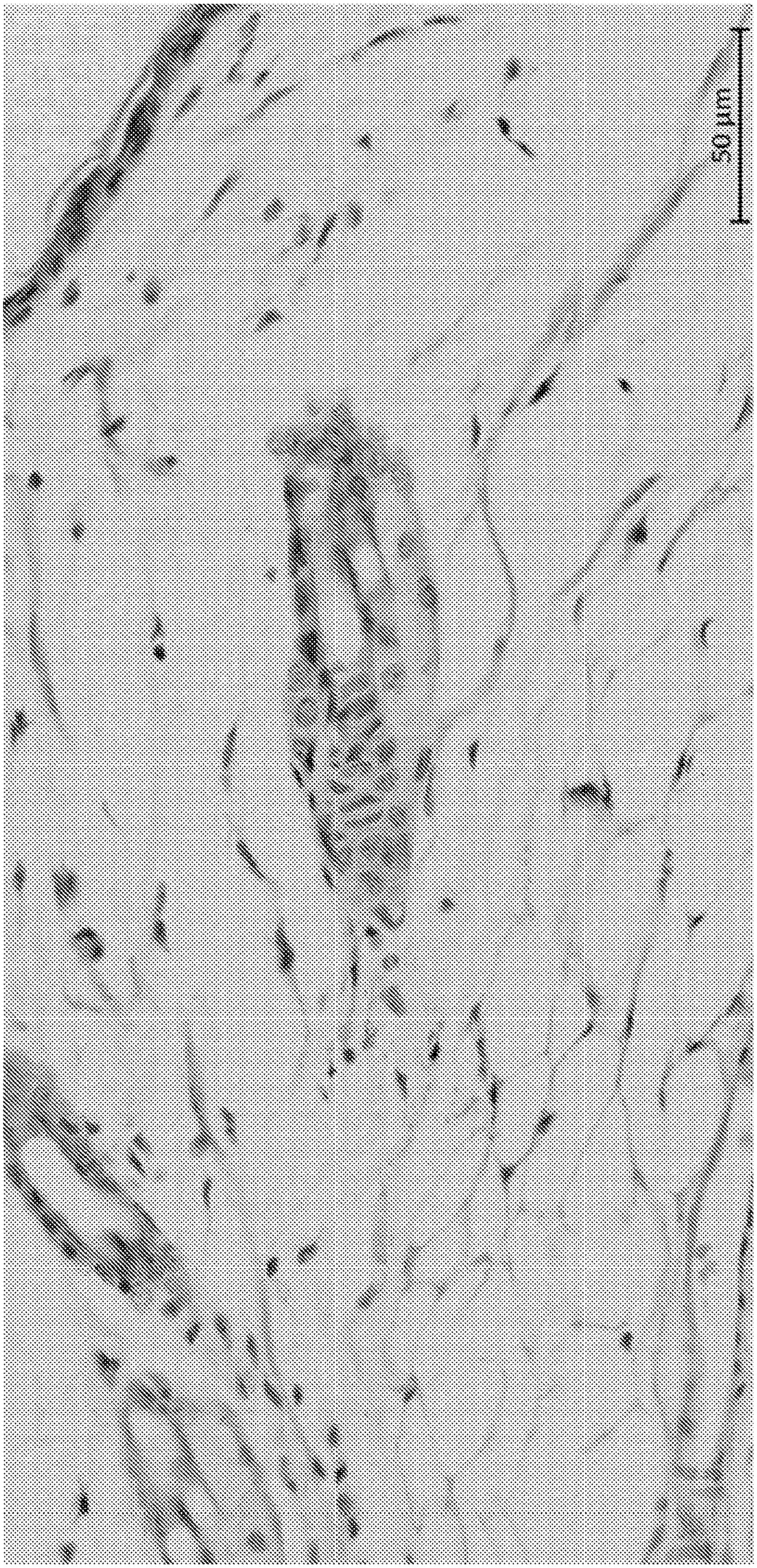
FIG. 21A shows an image obtained from Hematoxylin and Eosin (H&E) staining, with nuclear component (hematoxylin) and cytoplasmic components (eosin) differentially stained. Pathological assessment reports 2+ for negative control. Image shown is representative with at least 4 C57BL/6 mice per group. Scale bar=50 μm.
Figure 21B:
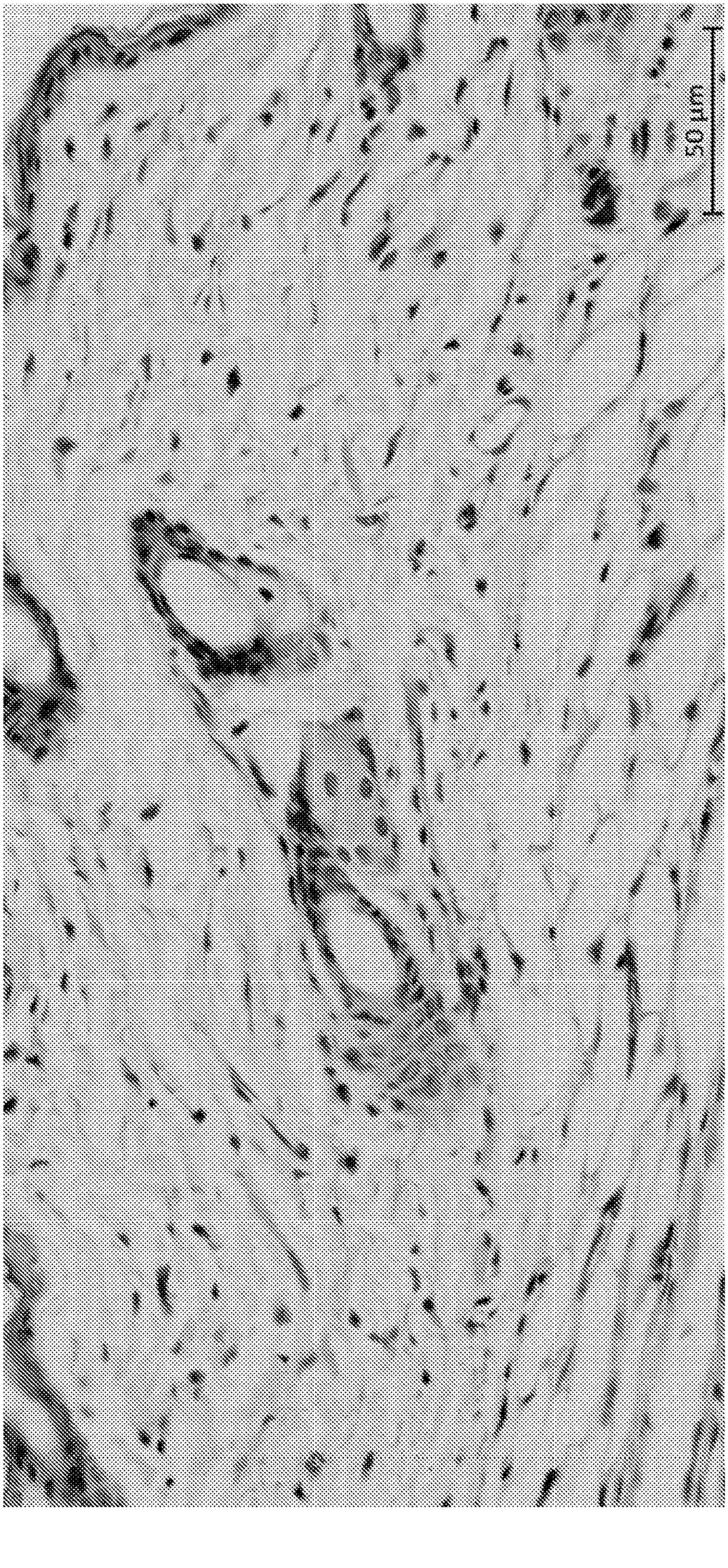
FIG. 21B shows an image obtained from Hematoxylin and Eosin (H&E) staining, with nuclear component (hematoxylin) and cytoplasmic components (eosin) differentially stained. Pathological assessment reports 3+ for PA12. Image shown is representative with at least 4 C57BL/6 mice per group. Scale bar=50 μm.
Figure 21C:
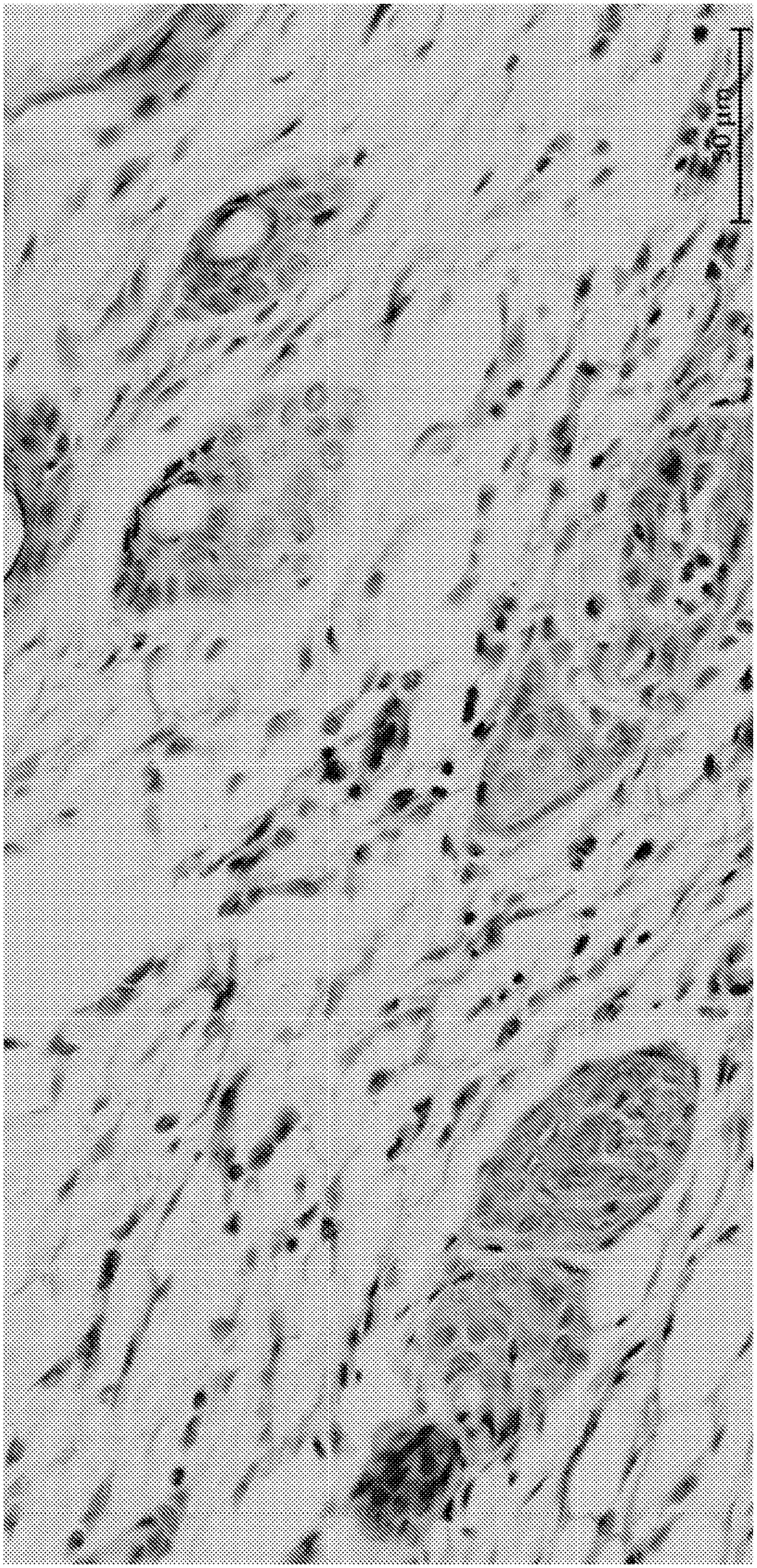
FIG. 21C shows an image obtained from Hematoxylin and Eosin (H&E) staining, with nuclear component (hematoxylin) and cytoplasmic components (eosin) differentially stained. Pathological assessment reports 3+ for PA12-(PA6-

Material biocompatibility was tested by cell viability assay method using chondrocytes (CHON-001) cell line on 3DP samples. FIG. 19 shows the cell viability percentage after 72 hours incubation period. For PLGA-based materials, it can be observed that PLGA-HA has the best performance as compared to the other PLGA materials. Alternately, PLA-based materials experienced lower cell viability. PLA-GPHP performed similar to PLA at an estimated of 75% cell viability while PLA-RGD and PLA-HA exhibited inferior performance.

Example 8: In Vivo Biocompatibility Analysis

In vivo biocompatibility analysis of 3D printed coupons was performed using murine models. 8 weeks old female $C_{57}$BL/6 wild type mice were purchased from InVivos Pte Ltd and randomly assigned to the material groups. All groups had at least 4 mice. Immunohistochemistry staining of murine skin tissues from study groups was performed using PA12-based (FIG. 20A, FIG. 20B, FIG. 20C and FIG. 21A, FIG. 21B, FIG. 21C), PCL-based (FIG. 22A, FIG. 22B, FIG. 22C, FIG. 22D and FIG. 23A, FIG. 23B, FIG. 23C, FIG. 23D), PLA-based (FIG. 24A, FIG. 24B, FIG. 24C, FIG. 24D, FIG. 24E and FIG. 25A, FIG. 25B, FIG. 25C, FIG. 25D, FIG. 25E) and PLGA-based (FIG. 26A, FIG. 26B, FIG. 26C, FIG. 26D and FIG. 27A, FIG. 27B, FIG. 27C, FIG. 27D) materials. Briefly, each mice was anaesthetized with ketamine/xylazine and a small incision was made on the upper dorsal back. Coupons were then inserted into the subcutaneous space under the skin. 4 weeks post implantation, all mice were sacrificed. Mouse skin surrounding the implant was harvested, fixed in formalin and embedded in paraffin for histological studies. Haematoxylin and Eosin (H&E) staining, as well as immunohistochemistry staining for CD3 (clone SP162) was performed on these skin sections. Appropriate controls were included and images were captured using Zeiss Axio Scan Z1 slide scanner. Analyses was carried out by a trained histopathologist, Dr Joe Yeong of Institute of Molecular Cell Biology, A*STAR. All animal handling procedures were approved by the Institutional Animal Care and Use Committee and conformed to the National Advisory Committee for Laboratory Animal Research Guidelines (IACUC #201550).

PA12 samples showed increased inflammatory response relative to sham (no implantation) for both pure PA12 samples and PA12-GPHyp samples. PA12-GPHyP represents bioactive PA12 that is PA-6 brush copolymer with $[GPHyp)_3]$ peptide, blended in PA12 base polymer. PCL samples showed no increase in inflammatory response after implantation, as compared to sham, for both pure PCL and bioactive PCL (PCL brush copolymers with RGD or $[(GPHyp)_3]$ peptides). Interesting findings were observed for PLA and PLGA samples in that both bioactive PLA and bioactive PLGA were observed to reduce inflammatory response in vivo. Pure PLA, PLA-HA (PLA brush copolymer with hyaluronic acid of MW 3,000-5,000) and PLA-GPHyp showed slight reduction in inflammatory response in vivo. However, PLA-RGD showed negligible inflammatory response in vivo, relative to sham. This is exciting as it showed the ability of PLA-RGD brush copolymers being able to reduce inflammatory response in vivo, making it a useful material for 3DP implants such as fixation devices ad biodegradable sutures. Likewise, 20% bioactive PLGA (PLGA-RGD brush copolymer) in base PLGA, was also observed to reduce inflammatory response in vivo. PLGA was observed to be intact despite repeated washing and attempts to detach material from tissues. Skin tissues were also observed to fill up the void left behind by degraded PLGA (FIG. 28). This makes bioactive PLGA a good material for applications such as 3DP skin scaffolds.

As can be seen, the results also advantageously show retention of bioactivity.

Example 9: Alkaline Phosphatase (ALP) Activity

Alkaline phosphatase (ALP) activity of C2C12 cells cultured on PCL coupons pre-incubated with or without BMP-2 after 3 days are measured and presented in FIG. 29.

Alkaline phosphatase (ALP) activity of C2C12 cells cultured on PLA coupons pre-incubated with or without BMP-2 after 3 days are measured and presented in FIG. 30.

Alkaline phosphatase (ALP) assay test was performed on both 3DP PCL and PLA sheets using C2C12 murine myoblast cells. Base polymers used were eSun 800C and Resomer L210S respectively. Bioactive copolymers used were PCL-RGD, PCL-GPHP, PLA-RGD and PLA-GPHP where RGD refers to arginine-glycine-aspartic acid and GPHP refers to $(GPHyp)_3$ peptide. In the absence of BMP-2 for PCL, it was observed that PCL-GPHP material had greater ALP activity as compared to the "no treatment" group, pure PCL and PCL-RGD materials. This strongly suggests that PCL-GPHP may have osteoinductive properties which can be attributed to the inclusion of $(GPHyp)_3$ peptide in its copolymer. However, the same trend could not be observed when the materials were pre-incubated with BMP-2 as pure PCL exhibited the best performance with a marginal advantage over PCL-GPHP in ALP activity. As for PLA without BMP-2, it can be observed that PLA-GPHP samples have slight increase in ALP activity over pure PLA sample and "no treatment" group. When the PLA samples are pre-incubated with BMP-2, ALP activity increased significantly as compared to "no treatment" group with PLA-GPHP sample exhibiting the best result. This finding suggests that PLA-GPHP may also have osteoinductive property which is induced by the $(GPHyp)_3$ peptide in its copolymer. GPHyp is a common motif present in fibrilla collagen, including collagen Iα2, the predominant protein in bone and GPHyp is known to enhance bone formation. Hence, the ability to observe ALP activities from 3DP sheets containing GPHyp-bearing bioadditive is indicative of the possibility of using bioactive polymer filaments if such materials are made available for orthopaedic implants such as 3DP bone grafts.

Example 10: Technical Features of Bioactive Polymer Filament

Advantageously, various embodiments of the bioactive polymer filament disclosed herein possess thermal stability, mechanical/physical competence/characteristics and biological competence/characteristics that makes its suitable for use as a feedstock in printing medical-related structures using FFF or FDM 3D printing technologies. FIG. 33. shows some of the key technical features of the bioactive polymer filament produced in accordance with various embodiments disclosed herein.

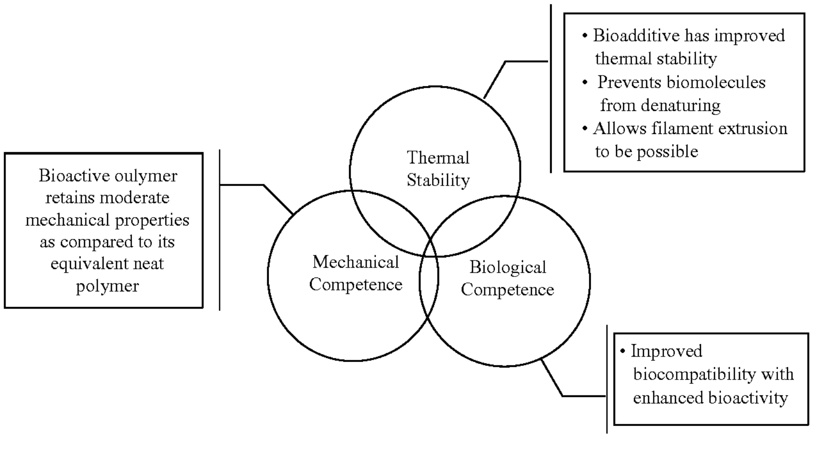

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

The invention claimed is:

1. A method of producing a bioactive polymer filament, the method comprising:

providing a base polymer powder and a bioactive copolymer;

mixing the base polymer powder with the bioactive copolymer to obtain a mixture; and extruding a bioactive polymer filament from the mixture at an extrusion temperature profile that is based on a predetermined melt/softening temperature and a predetermined onset degradation temperature of the bioactive polymer; and performing a post-extrusion thermal analysis on the extruded bioactive polymer filament to assess onset degradation of the bioactive polymer in the filament, wherein the bioactive copolymer is a bioactive synthetic copolymer with a poly (norbornene) backbone comprising one or more repeating units represented by general formula (I):

(I)

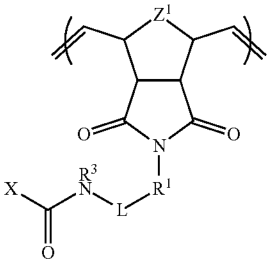

and one or more repeating units represented by general formula (II):

(II)

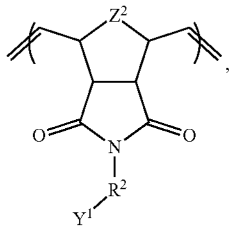

wherein:

$R^1$ is optionally substituted alkyl;

$R^2$ is selected from a single bond, optionally substituted alkyl, optionally substituted alkenyl, optionally substituted alkynyl, optionally substituted alkoxyalkyl, optionally substituted alkylcarbonyl or optionally substituted alkylcarbonylalkyl;

$R^3$ is selected from H, optionally substituted alkyl, optionally substituted alkenyl or optionally substituted alkynyl;

L is heteroalkylene;

X comprises a bioactive moiety selected from the group consisting of proteins, peptides, carbohydrates, collagen, hyaluronic acid, therapeutic/drug molecules and derivatives thereof;

$Y^1$ comprises a synthetic polymer or parts thereof; and $Z^1$ and $Z^2$ are each independently selected from $CR^aR^b$, O, $NR^c$, $SiR^aR^b$, $PR^a$ or S, wherein $R^a$, $R^b$ and $R^c$ are each independently selected from the group consisting of H, optionally substituted alkyl, optionally substituted alkenyl and optionally substituted alkynyl.

2. The method of claim 1, wherein the bioactive copolymer is acellular.

3. The method of claim 1, wherein the bioactive copolymer is obtained by ring-opening metathesis polymerisation (ROMP).

4. The method of claim 1, wherein $Y^1$ is represented by general formula (III):

(III)

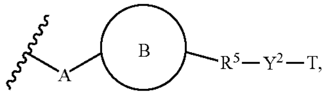

wherein:

A is selected from a single bond, oxy, carbonyl, oxycarbonyl, carboxyl, optionally substituted alkoxy, optionally substituted alkoxyalkyl, optionally substituted alkylcarbonyl, optionally substituted alkylcarbonylalkyl, optionally substituted carboxyalkyl, optionally substituted oxycarbonylalkyl, optionally substituted alkylcarboxylalkyl, optionally substituted alkoxycarbonylalkyl, N or $NR^c$ wherein $R^c$ is independently selected from H, optionally substituted alkyl, optionally substituted alkenyl or optionally substituted alkynyl;

B is optionally present as a ring selected from 1,2,3-triazole or succinimide;

$R^5$ is selected from a single bond, optionally substituted alkyl, optionally substituted alkenyl, optionally substituted alkynyl, optionally substituted alkoxyalkyl, optionally substituted alkylcarbonyl or optionally substituted alkylcarbonylalkyl;

$Y^2$ is selected from the group consisting of polypropylene (PP), polyesters, poly(lactic acid) (PLA), poly(lactic-co-glycolic acid) (PLGA), poly(caprolactone) (PCL), polystyrene (PS), polyacrylates, poly(meth)acrylates, polyamides (PA), polyurethane (PU), and parts thereof; and T is a terminal group selected from the group consisting of hydrogen, halogen, hydroxyl, amino, acyl, thiol, optionally substituted alkyl, optionally substituted alkenyl, optionally substituted alkynyl, optionally substituted alkoxy, optionally substituted alkoxyalkyl, optionally substituted alkylcarbonyl, optionally substituted alkylcarbonylalkyl, optionally substituted carboxyalkyl, optionally substituted oxycarbonylalkyl, optionally substituted alkylcarboxylalkyl and optionally substituted alkoxycarbonylalkyl.

5. The method of claim 4, wherein $Y^1$ is selected from the following general formulae (IIIa), (IIIb), (IIIc), (IIId), (IIIe), (IIIf), or (IIIg):

(IIIa)

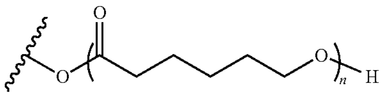

(IIIb)

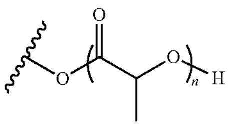

(IIIc)

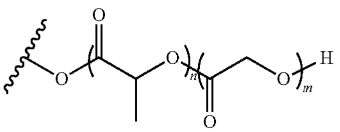

(IIId)

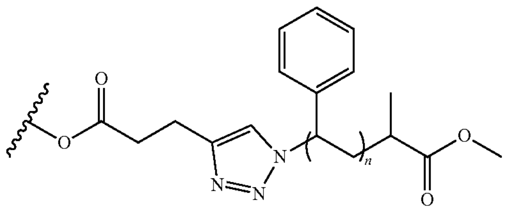

-continued (IIIe)

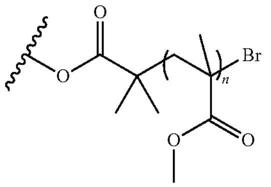

(IIIf)

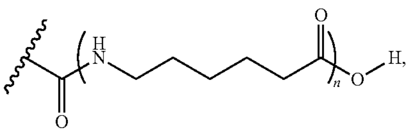

or (IIIg)

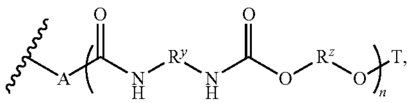

wherein:

$R^y$ is selected from an alkyl, aryl or biaryl;

$R^z$ is alkyl;

A is O or $NR^c$ wherein $R^c$ is independently selected from H, optionally substituted alkyl, optionally substituted alkenyl or optionally substituted alkynyl;

T is a terminal group selected from the group consisting of hydrogen and methyl;

n≥1; and m≥1.

6. The method of claim 1, wherein the base polymer powder is obtained from cryogenic milling of base polymer pellets.

7. The method of claim 1, wherein the base polymer powder has an average particle size of no more than 1 mm.

8. The method of claim 1, wherein the post-extrusion thermal analysis comprises application of thermogravimetric analysis (TGA) and differential scanning calorimetry (DSC).

9. The method of claim 1, wherein the extruding is performed using an extruder having one or more rotating screws.

10. The method of claim 1, wherein the extruded bioactive polymer filament has a filament diameter falling in the range of from 1.5 mm to 4.0 mm.

11. The method of claim 1, further comprising performing a pre-extrusion thermal analysis on the base polymer and/or bioactive copolymer to determine the melt temperature and the onset degradation temperature of the bioactive polymer.

12. The method of claim 1, wherein the base polymer and bioactive copolymer have been vacuum dried prior to mixing.

13. The method of claim 1, wherein the mixture of base polymer and bioactive copolymer comprises 60.0 wt % to 99.9 wt % of the base polymer and 0.1 wt % to 40.0 wt % of the bioactive copolymer.

14. The method of claim 1, wherein the base polymer is selected from the group consisting of polypropylene (PP), polyesters, poly(lactic acid) (PLA), poly(lactic-co-glycolic acid) (PLGA), poly(caprolactone) (PCL), polystyrene (PS), polyacrylates, poly(meth)acrylates, polyamides (PA), polyurethane (PU) and combinations thereof.

* * * * *